United States Patent
Krainc et al.

(10) Patent No.: US 10,167,270 B2
(45) Date of Patent: Jan. 1, 2019

(54) SUBSTITUTED QUINAZOLINE COMPOUNDS AND USES THEREOF FOR MODULATING GLUCOCEREBROSIDASE ACTIVITY

(71) Applicant: Northwestern University, Evanston, IL (US)

(72) Inventors: Dimitri Krainc, Chicago, IL (US); Richard B. Silverman, Winnetka, IL (US); Jianbin Zheng, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/199,207

(22) Filed: Jun. 30, 2016

(65) Prior Publication Data
US 2017/0001976 A1 Jan. 5, 2017

Related U.S. Application Data

(60) Provisional application No. 62/187,461, filed on Jul. 1, 2015.

(51) Int. Cl.
| | |
|---|---|
| *C07D 401/04* | (2006.01) |
| *A61K 38/47* | (2006.01) |
| *C07D 405/14* | (2006.01) |
| *C07D 401/14* | (2006.01) |
| *C07D 417/14* | (2006.01) |
| *C07D 413/14* | (2006.01) |
| *C07D 497/04* | (2006.01) |
| *C07D 487/08* | (2006.01) |
| *C07D 239/94* | (2006.01) |
| *C07D 409/04* | (2006.01) |
| *C07D 405/04* | (2006.01) |
| *C12N 9/24* | (2006.01) |

(52) U.S. Cl.
CPC ............ *C07D 401/04* (2013.01); *A61K 38/47* (2013.01); *C07D 239/94* (2013.01); *C07D 401/14* (2013.01); *C07D 405/04* (2013.01); *C07D 405/14* (2013.01); *C07D 409/04* (2013.01); *C07D 413/14* (2013.01); *C07D 417/14* (2013.01); *C07D 487/08* (2013.01); *C07D 497/04* (2013.01); *C12N 9/2402* (2013.01); *C12Y 302/01045* (2013.01)

(58) Field of Classification Search
CPC .. C07D 401/04; C07D 239/94; C07D 401/14; C07D 405/04; C07D 405/14; C07D 409/04; C07D 413/14; C07D 417/14; C07D 487/08; C07D 497/04; A61K 31/517; A61K 38/47
See application file for complete search history.

(56) References Cited

U.S. PATENT DOCUMENTS 2,940,844 A * 6/1960 Knusli ................ C07D 213/74
504/168

OTHER PUBLICATIONS

Lee et al. Journal of Medicinal Chemistry (1995), 38(18), 3547-57.*
Aguilar-Moncayo et al., "Bicyclic (galacto)nojirimycin analogues as glycosidase inhibitors: Effect of structural modifications in their pharmacological chaperone potential towards beta-glucocerebrosidase", Org. Biomol. Chem. 2011, 9:3698-3713.
Aharon-Peretz et al., "Mutations in the glucocerebrosidase gene and Parkinson's disease in Ashkenazi Jews", N. Engl. J. Med. 2004, 351:1972-1977.
Bennett et al., "Gaucher disease and its treatment options", Ann. Pharmacother. 2013, 47:1182-1193.
Berger et al., "Tool compounds robustly increase turnover of an artificial substrate by glucocerebrosidase in human brain lysates", PLoS One, 2015, 10:e0119141.
Butters et al., "Imino sugar inhibitors for treating the lysosomal glycosphingolipidoses", Glycobiology, 2005, 15:43R-52R.
Filippova et al., "Structural characterization of a hypothetical protein: a potential agent involved in trimethylamine metabolism in Catenulispora acidiphila", J. Struct. Funct. Genomics, 2014, 15:33-40.
Grabowski et al., "Phenotype, diagnosis, and treatment of Gaucher's disease", Lancet 2008, 372:1263-1271.
Grabowski et al., "Gaucher disease types 1 and 3: Phenotypic characterization of large populations from the ICGG Gaucher Registry", Am. J. Hematol, 2015, 90 Suppl 1, S12-18.
Hruska et al., "Gaucher disease: mutation and polymorphism spectrum in the glucocerebrosidase gene (GBA)", Hum. Mutat. 2008, 29:567-583.
Huang et al., "N4-phenyl modifications of N2-(2-hydroxyl)ethyl-6-(pyrrolidin-1-yl)-1,3,5-triazine-2,4-diamines enhance glucocerebrosidase inhibition by small molecules with potential as chemical chaperones for Gaucher disease", Bioorg. Med. Chem. Lett. 2007, 17:5783-5789.
Lin et al., "Genetics and genomics of Parkinson's disease", Genome Med. 2014, 6:48.
Lo et al., "Evaluation of fluorescence-based thermal shift assays for hit identification in drug discovery", Anal. Biochem. 2004, 332:153-159.
Marugan et al., "Non-iminosugar glucocerebrosidase small molecule chaperones", Medchemcomm. 2012, 3:56-60.

(Continued)

*Primary Examiner* — Kahsay Habte
(74) *Attorney, Agent, or Firm* — Andrus Intellectual Property Law, LLP

(57) ABSTRACT

Disclosed are new small molecules having a substituted quinazoline core structure and the uses thereof for modulating glucocerebrosidase activity. Also disclosed are pharmaceutical compositions comprising the small molecules or activated glucocerebrosidase conjugated to the small molecules, which compositions may be administered in methods of treating diseases or disorders associated with glucocerebrosidase activity, including neurological diseases and disorders such as Gaucher's disease and Parkinson's disease.

10 Claims, 6 Drawing Sheets

(56) References Cited

OTHER PUBLICATIONS

Marugan et al., "Evaluation of quinazoline analogues as glucocerebrosidase inhibitors with chaperone activity", J. Med. Chem. 2011, 54:1033-1058.

Mazzulli et al., "Gaucher disease glucocerebrosidase and alpha-synuclein form a bidirectional pathogenic loop in synucleinopathies", Cell 2011, 146:37-52.

Sardi et al., "Augmenting CNS glucocerebrosidase activity as a therapeutic strategy for parkinsonism and other Gaucher-related synucleinopathies", Proc. Natl. Acad. Sci. U.S.A.2 013, 110:3537-3542.

Sawkar et al., "Chemical chaperones and permissive temperatures alter localization of Gaucher disease associated glucocerebrosidase variants", ACS Chem. Biol. 2006, 1:235-251.

Sawkar et al., "Chemical chaperones increase the cellular activity of N370S beta-glucosidase: a therapeutic strategy for Gaucher disease", Proc. Natl. Acad. Sci. U.S.A. 2002, 99:15428-15433.

Schapira et al., "Slowing of neurodegeneration in Parkinson's disease and Huntington's disease: future therapeutic perspectives", Lancet 2014, 384:545-555.

Sidransky et al., "The link between the GBA gene and parkinsonism", Lancet Neurol. 2012, 11:986-998.

Sidransky et al., "Multicenter analysis of glucocerebrosidase mutations in Parkinson's disease", N. Engl. J. Med. 2009, 361:1651-1661.

Steet et al., "The iminosugar isofagomine increases the activity of N370S mutant acid beta-glucosidase in Gaucher fibroblasts by several mechanisms", Proc. Natl. Acad. Sci. U.S.A. 2006, 103:13813-13818.

Storz et al., "Convenient and Practical One-Pot Synthesis of 4-Chloropyrimidines via a Novel Chloroimidate Annulation", Org. Process Res. Dev. 2011, 15:918-924.

Sybertz et al., "Development of targeted therapies for Parkinson's disease and related synucleinopathies", J. Lipid Res. 2014, 55:1996-2003.

Tekoah et al., "Glycosylation and functionality of recombinant beta-glucocerebrosidase from various production systems", Biosci. Rep. 2013, 33:771-U272.

Trapero et al., "Potent aminocyclitol glucocerebrosidase inhibitors are subnanomolar pharmacological chaperones for treating gaucher disease", J. Med. Chem. 2012, 55:4479-4488.

Trapero et al., "Polyhydroxylated bicyclic isoureas and guanidines are potent glucocerebrosidase inhibitors and nanomolar enzyme activity enhancers in Gaucher cells", J. Am. Chem. Soc. 2011, 133:5474-5484.

Tropak et al., "Identification of pharmacological chaperones for Gaucher disease and characterization of their effects on beta-glucocerebrosidase by hydrogen/deuterium exchange mass spectrometry", Chembiochem 2008, 9:2650-2662.

Urban et al., "Optimization and validation of two miniaturized glucocerebrosidase enzyme assays for high throughput screening", Comb. Chem. High Throughput Screen. 2008, 11:817-824.

Wang et al., "Rational design and synthesis of highly potent pharmacological chaperones for treatment of N370S mutant Gaucher disease", J. Med. Chem. 2009, 52:3146-3149.

Zheng et al., "Three classes of glucocerebrosidase inhibitors identified by quantitative high-throughput screening are chaperone leads for Gaucher disease", Proc. Natl. Acad. Sci. U.S.A. 2007, 104:13192-13197.

International Search Report for PCT/US/2016/040467 dated Nov. 24, 2016.

Written Opinion for PCT/US/2016/040467 dated Nov. 24, 2016.

\* cited by examiner

SUBSTITUTED QUINAZOLINE COMPOUNDS AND USES THEREOF FOR MODULATING GLUCOCEREBROSIDASE ACTIVITY

CROSS-REFERENCE TO RELATED PATENT APPLICATIONS

The present application claims the benefit of priority under 35 U.S.C. § 119(e) to U.S. Provisional Patent Application No. 62/187,461, filed on Jul. 1, 2015, the content of which is incorporated herein by reference in its entirety.

BACKGROUND

The field of the invention relates to new small molecules and uses of the new small molecules for modulating glucocerebrosidase activity. The new small molecules have a substituted quinazoline core structure and may be administered to treat diseases and disorders associated with aberrant glucocerebrosidase activity including neurodegenerative diseases, such as Gaucher's disease and Parkinson's disease Glucocerebrosidase (EC 3.2.1.45), which also is called β-glucocerebrosidase, β-glucosidase, D-glucosyl-N-acyl-sphingosine glucohydrolase, or GCase, is an enzyme having glucosylceramidase activity. Glucocerebrosidase (GCase) is required to cleave the beta-glucosidic linkage of the chemical glucocerebroside, which is an intermediate in glycolipid metabolism. Glucocerebrosidase is localized in the lysosome and disabling mutations in the gene for glucocerebrosidase (GBA1) are associated with abnormal accumulation of lipids in lysosomes.

Genetic diseases caused by mutations in GBA1 include neurodegenerative diseases such as Gaucher's disease and Parkinson's disease. Gaucher's disease is a rare genetic disease caused by GBA1 gene mutations. Currently, the treatment for Type 1 Gaucher's disease is enzyme replacement therapy (ERT) administered every two weeks. ERT is very expensive and not effective for neuronopathic forms of Gaucher's disease. Mutations in GBA1 also are linked to Parkinson's disease (PD) and increase the risk of PD.

The so-called "pharmacological chaperone strategy" has been previously attempted in order to activate GCase as a treatment for diseases and disorders associated with deficient GCase activity. However, none of the compounds used in the pharmacological chaperone strategy were successful in activating GCase presumably because they targeted the active site of GCase.

Here, we disclose novel substituted quinazoline compounds which modulate glucocerebrosidase activity. Some of the novel compounds have potent inhibitory activity and binding affinity. As such, these compounds could be used as pharmacological chaperones. In addition, some of the compounds in the present study showed high activation activity in GCase activity assays and could be used as GCase activators. The novel substituted quinazoline compounds disclosed herein have better chemical and physical properties than previous reported non-active site GCase inhibitors. (See Marugan et al., J. Med. Chem. 2011; 54(4) 1033-58, the contents of which is incorporated herein by reference in its entirety). These better chemical and physical properties include polar surface area, solubility, increased number of rotatable bonds, and increased number of potential hydrogen bonding members.

SUMMARY

Disclosed are new small molecules having a quinazoline core structure and uses of the small molecules for modulating glucocerebrosidase activity. The new small molecules preferably modulate glucocerebrosidase activity by binding to glucocerebrosidase and inhibiting, or alternatively activating glucocerebrosidase. The new small molecules may be formulated as pharmaceutical compositions that comprise the small molecules or that comprise activated glucocerebrosidase conjugated to the small molecules, which compositions may be administered in methods of treating and/or preventing diseases or disorders associated with glucocerebrosidase activity, including neurological diseases and disorders such as Gaucher's disease and Parkinson's disease. The disclosed small molecules also may comprise fluorophores or may be conjugated to fluorophores to generate fluorescent probes. The fluorescent probes contemplated herein may exhibit fluorescence polarization and may be utilized in high throughput screening methods to identify novel modulators of glucocerebrosidase.

DETAILED DESCRIPTION

Figure 1:
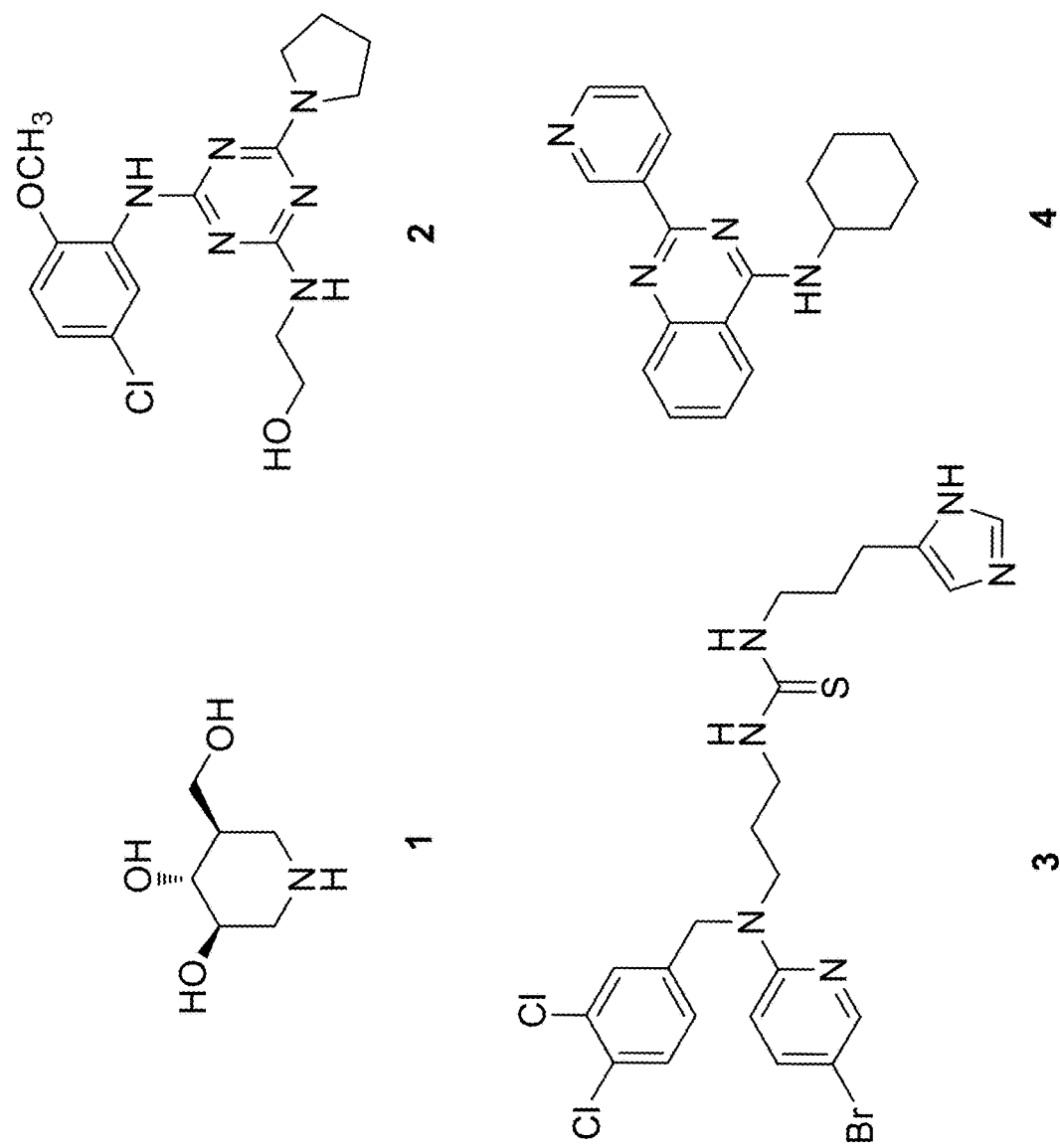
FIG. 1. Structures of GCase inhibitors.

The disclosed subject matter further may be described utilizing terms as defined below.

Unless otherwise specified or indicated by context, the terms "a", "an", and "the" mean "one or more." For example, "a modulator of glucocerebrosidase activity" should be interpreted to mean "one or more modulators of glucocerebrosidase activity."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The terms "subject," "patient," and "individual" may be used interchangeably herein. A subject may be a human subject. A subject may refer to a human subject having or at risk for acquiring a disease or disorder that is associated with aberrant glucocerebrosidase activity. As used herein, the term "aberrant" means higher or lower activity relative to a normal healthy subject. In specific embodiments, a subject exhibiting aberrant glucocerebrosidase have or be at risk for acquiring a neurological disease or disorder, including degenerative neurological diseases or disorders such as Gaucher's disease and Parkinson's disease associated with aberrant glucocerebrosidase activity.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

The term "alkyl" as contemplated herein includes a straight-chain or branched alkyl radical in all of its isomeric forms. Similarly, the term "alkoxy" refers to any alkyl radical which is attached via an oxygen atom (i.e., a radical represented as "alkyl-O—*". As used herein, an asterisk "*" is used to designate the point of attachment for any radical group or substituent group.

As used herein, the term "modulate" means decreasing or inhibiting activity and/or increasing or augmenting activity. For example, modulating glucocerebrosidase activity means decreasing or inhibiting glucocerebrosidase activity and/or increasing or augmenting glucocerebrosidase activity. The compounds disclosed herein may be administered to modulate glucocerebrosidase activity for example, as an inhibitor, a chaperone, or an activator.

The compounds disclosed herein may be referred to as "2-substituted, N-substituted quinazoline compounds" or "substituted quinazoline compounds." The compounds or salt or solvates thereof may be described as having a Formula I as follows:

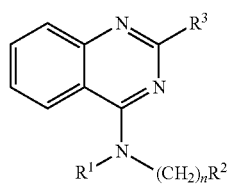

I wherein:
$R^1$ is hydrogen or C1-C6 alkyl;
n is 0, 1, 2, 3, or 4; and
$R^2$ is hydrogen, a C1-C10 alkyl group (straight chain or branched), a C3-C8 cycloalkyl group, a saturated or unsaturated homocycle or heterocycle group comprising one 5- or 6-membered ring or comprising two or three fused 5- or 6-membered rings, a phenoxy group, a C1-C6-branched or straight chain alkyl-phenoxy group, a 2,3-dihydro-1H-indenyl group, a 1,2,3,4-tetrahydro-naphthalenyl group, a C2-C10 alkenyl group (straight chain or branched), a C2-C10 alkynyl group, a polyethylene oxide group (e.g., PEG), a pyridinoxy group (e.g., 2-, 3-, or 4-pyridinoxy), an indoloxy group (e.g., 1H-indol-4-yl-oxy), a benzofuranoxy group (e.g., benzofuran-4-yl-oxy), or $R^2$ has a formula

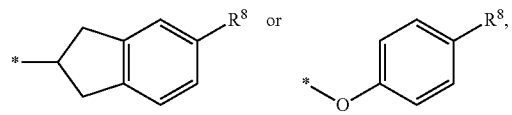

wherein $R^8$ is halo or $R^8$ has a formula selected from

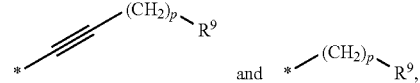

p is 1-10 and $R^9$ is amino or $R^9$ has a formula selected from

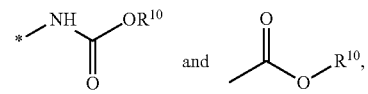

wherein $R^{10}$ is H, C1-C1-alkyl (straight chain or branched), or a succinimidyl group (e.g., N-succinimidyl);

$R^2$ optionally is substituted at one or more positions with a C1-C6 alkyl group, a C1-C6 alkoxy group, a halo group, a phenyl group, a benzyl group, an amino group, a hydroxyl group, a tert-butyloxycarbonyl (BOC) group, a sulfonylmethylphenyl group, a 2,3-dihydro-1,4-benzodioxine-2-carbaldehyde group, a 2,3-dihydromethyl-1,4-benzodioxin group, an imidazole group, a piperazine group, a 1-methylpiperazine group, a 4-piperazin-1-yl-benzaldehyde group, a 4-(4-methylpiperazin-1-yl)benzaldehyde group, or an azide group; or where n is 0, $R^1$ and $R^2$ together form a heterocycle comprising one, two, or three 5- or 6-membered rings (e.g., N-2,3,4,9-tetrahydro-pyrido[3,4-b]indole, tryptolinyl, or 2,3,4,5-tetrahydro-benzo[f][1,4]oxazepine);

optionally, at least one of $R^1$ and $R^2$ is not hydrogen; and
$R^3$ is pyridinyl (for example, 2-yl, 3-yl, or 4-yl), phenyl, thiophenyl (for example 2-yl or 3-yl), halo, furanyl (for example 2-yl or 3-yl), pyrimidinyl (for example 2-yl, 4-yl, or 5-yl), and $R^3$ optionally is substituted at one or more positions with C1-C6 alkyl, halo, amino, or $R^3$ has a formula,

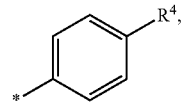

wherein R⁴ is amino, or R⁴ has a formula

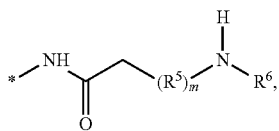

wherein R⁵ is —CH₂— or —O—CH₂—CH₂—, and m is 0-4,

R⁶ is H or R⁶ has a formula

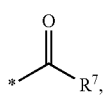

wherein R⁷ is H, —OH, C1-C6 alkyl (which may be straight chain or branched), or C1-C6 alkoxy (which may be straight chain or branched).

In some embodiments, R² is selected from the group consisting of a cyclohexylaminyl group, an N-alkyl cyclohexylaminyl group, an N,N-dialkyl cyclohexylaminyl group, a 7-azabicyclo[2.2.1]heptanyl group, a piperidinyl group, a tetrahydropyranyl group, a 1,4-dioxanyl group, a dihydrobenzo[1,4]dioxanyl group, a pyridinyl group, a pyrimidinyl group, a pyrazinyl group, a quinoxalinyl group, a 1,3-benzodioxolyl group, a (2h)tetrahydroisoquinolinyl group, an isoindolinyl group, an N-methylisoindolinyl group, a 1,3-benzothiazolyl group, a 1,3-benzodiazolyl group, a naphthalenyl group, a 1,3-benzoxazolyl group, a 1,4-benzodioxanyl group, 3,4-Dihydro-2H-1-benzopyranyl group, a 2,1,3-benzothiadiazolyl group, a 1,2,4-oxadiazolyl group, 3-isobutyl-1,2,4-oxadiazol-5-yl group, a thiazolyl group, a tetrahydrohydronaphthalenyl group, a 2,3-dihydro-1H-indenyl group, an indolyl group, a pyrrolidinyl group, an N-methylpyrrolidinyl group, a bicyclo[2.2.1]heptanyl group (i.e., norbornanyl), and a tricyclo[3.3.1.1(3,7)]decanyl group (i.e., adamantanyl), and alkyl-phenoxy group (e.g., ethan-2-yl-phenoxy, propan-2-yl-phenoxy, isopropyl-phenoxy), a 2,3-dihydro-1H-indenyl group, a 1,2,3,4-tetrahydro-naphthalenyl group, a C2-C10 alkenyl group (straight chain or branched), a C2-C10 alkynyl group, a polyethylene oxide group (e.g., PEG), a pyridinoxy group (e.g., 2-, 3-, or 4-pyridinoxy), an indoloxy group (e.g., 1H-indol-4-yl-oxy), or a benzofuranoxy group (e.g., benzofuran-4-yl-oxy). 3,4-Dihydro-2H-1-benzopyran In other embodiments, R is selected from the group consisting of

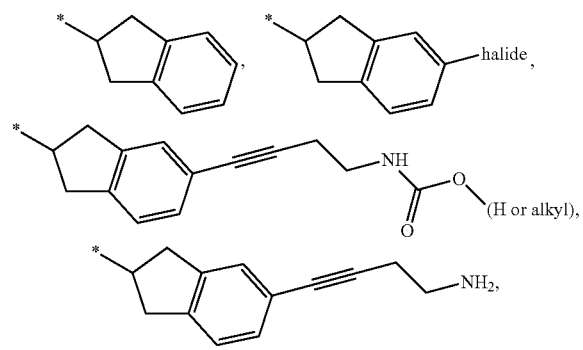

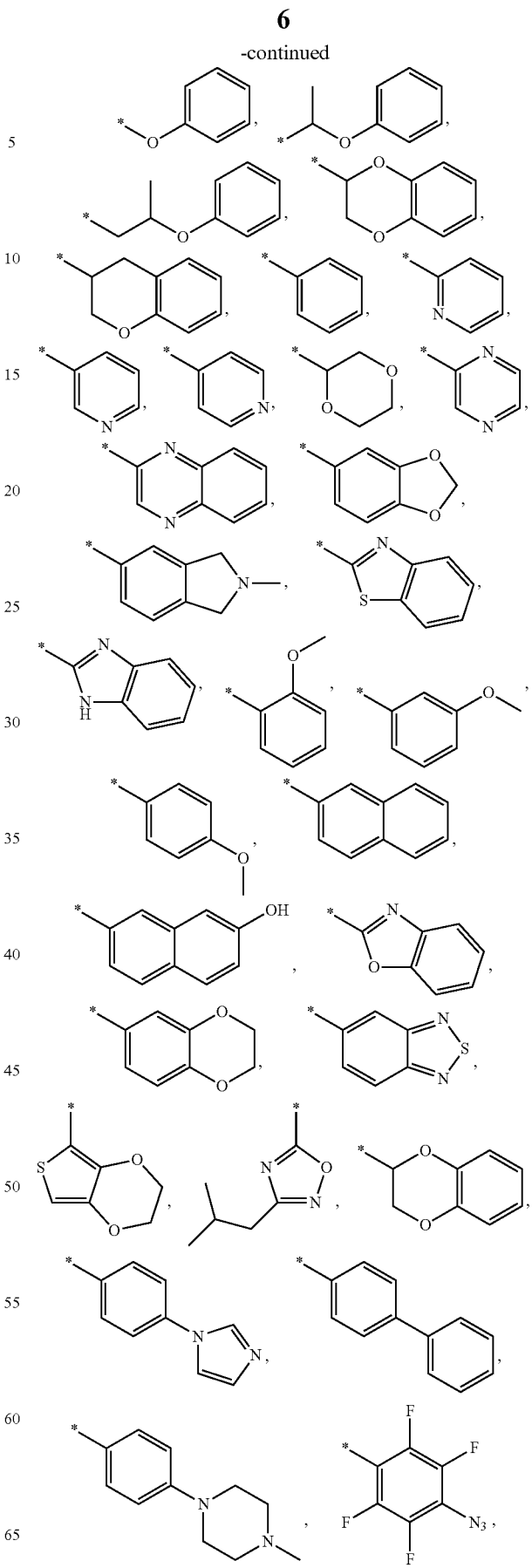

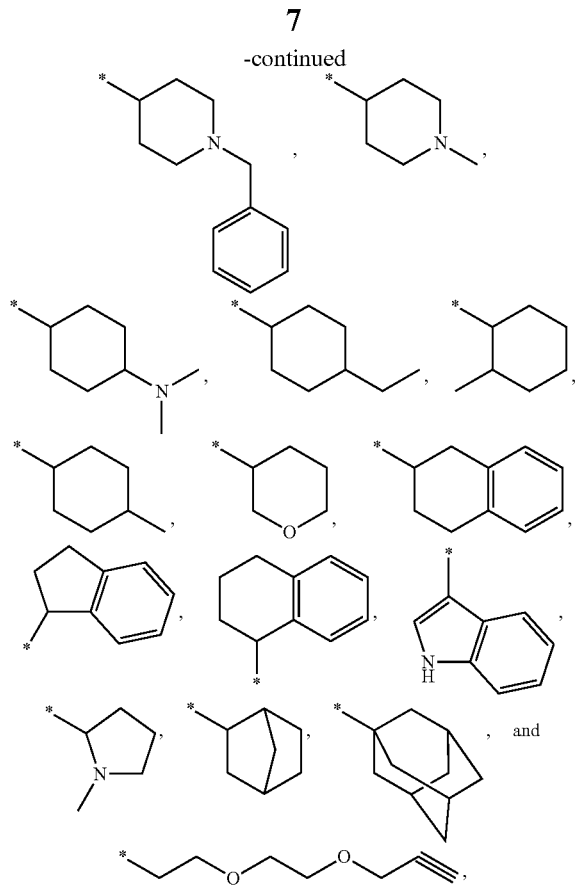

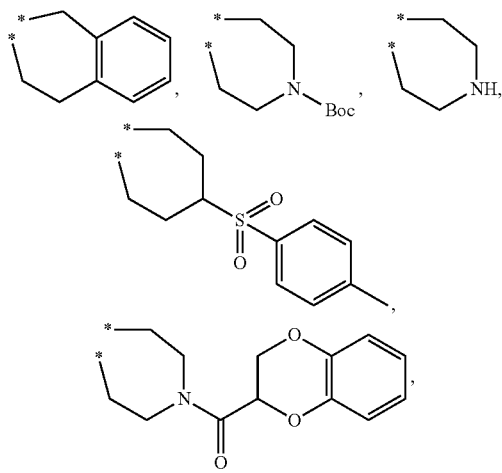

where the asterisk (*) designates the point of attachment of $R^2$ to the alkyl linker $(CH_2)_n$ or the point of attachment of $R^2$ to the pendant nitrogen of the quinazoline moiety where n is 0.

In some embodiments, $R^1$ and $R^2$ together may form a heterocycle with the pendant nitrogen atom of the quinazoline moiety (e.g., where n is 0 and $R^1$ and $R^2$ are directed bonded to the pendant 4-carbon nitrogen atom of the quinazoline moiety). The heterocycle thus formed may comprise one 5- or 6-membered ring or may comprise two or three fused 5- or 6-membered rings, for example, where $R^1$ and $R^2$ are selected from the group consisting of

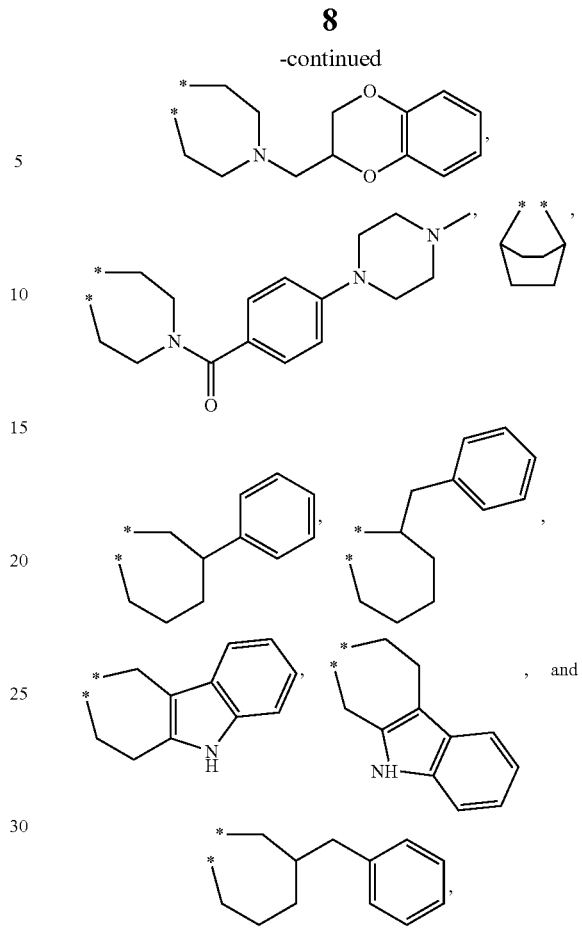

where the asterisk (*) designates the point of attachment of $R^1$ and $R^2$ to the pendant nitrogen atom of the quinazoline moiety.

In some embodiments, $R^3$ is selected from the group consisting of

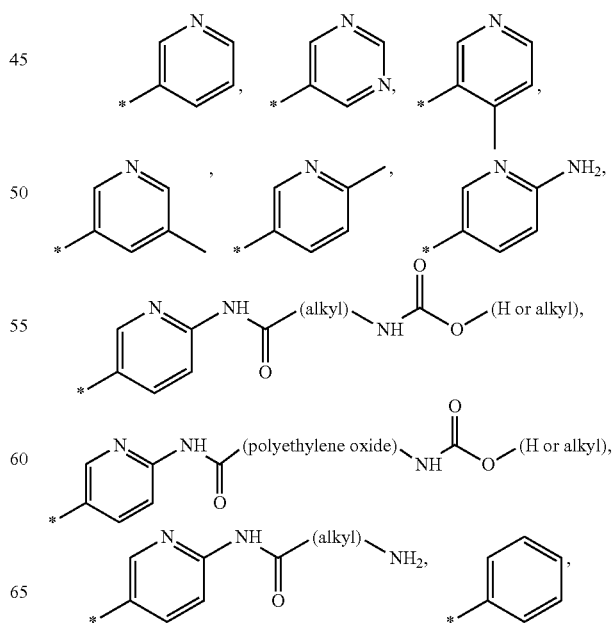

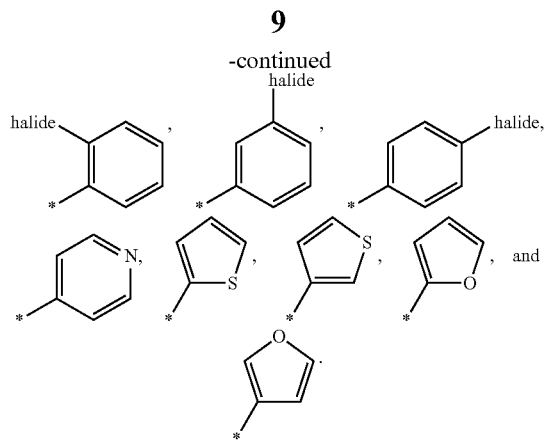

In some embodiments, the disclosed compounds may be conjugated to biotin (e.g., via the $R^3$ constituent optionally via a linker between biotin and the $R^3$ constituent). In other embodiments, the disclosed compounds may be conjugated to a solid support such as an agarose bead (e.g., via the $R^3$ constituent optionally via a linker between the solid support and the $R^3$ constituent).

In other embodiments, the disclosed compounds may comprise or may be conjugated to a fluorophore such as rhodamine or fluorescein. In some embodiments of the disclosed compounds, any of substituents $R^1$, $R^2$, and $R^3$ may comprise or may be conjugated to a fluorophore (e.g., via the $R^3$ constituent optionally via a linker between the fluorophore and the $R^3$ constituent), including fluorophores suitable for use in fluorescence polarization assays. As used herein, a "fluorophore" is a chemical group that can be excited (e.g., by light or a chemical reaction) to emit fluorescence. Some suitable fluorophores may be excited by light to emit phosphorescence. As used herein, a "dye" may include a fluorophore. The dithio compounds described herein may include fluorophore selected from but not limited to: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP;

PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodaminelsoThioCyanate; True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3. As used herein, a "fluorophore" may include a salt of the fluorophore.

The disclosed compounds may include two substituted quinazoline groups conjugated via a linker. Compounds that include two substituted quinazoline groups conjugated via a linker between the pendant 4-carbon nitrogens of the quinazoline groups may be illustrated as follows:

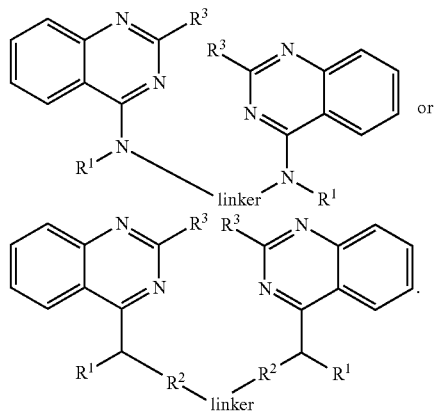

In some embodiments, the disclosed compounds having two substituted quinazoline groups conjugated via a linker may be described as having a Formula II as follows:

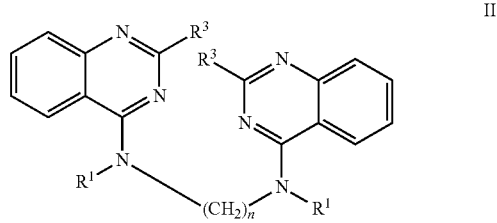

II wherein $R^1$ and $R^3$ are as defined for Formula I above, n=1-10, and the alkyl group $((CH_2)_n)$ serves as a linker between the two substituted quinazoline groups.

In some embodiments, the disclosed compounds having two substituted quinazoline groups conjugated via a linker may be described as having a Formula III as follows:

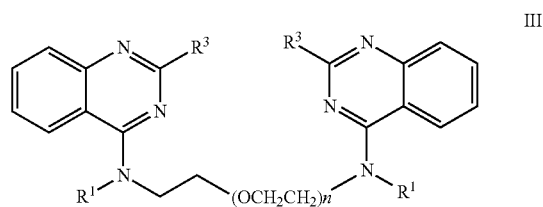

III wherein $R^1$ and $R^3$ are as defined for Formula I above, n=1-10, and the poly ethylene oxide group $((OCH_2CH_2)_n)$ serves as a linker between the two substituted quinazoline groups.

In some embodiments, the disclosed compounds having two substituted quinazoline groups conjugated via a linker may be described as having a Formula IV as follows:

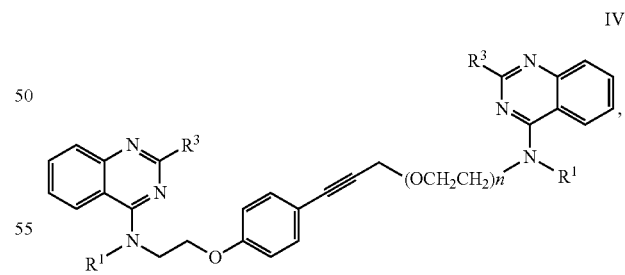

IV wherein $R^1$ and $R^3$ are as defined for Formula I above, n=1-10, and the compound has a phenoxy alkynyl poly ethylene oxide linker.

In some embodiments, the disclosed compounds having two substituted quinazoline groups conjugated via a linker may be described as having a Formula V as follows:

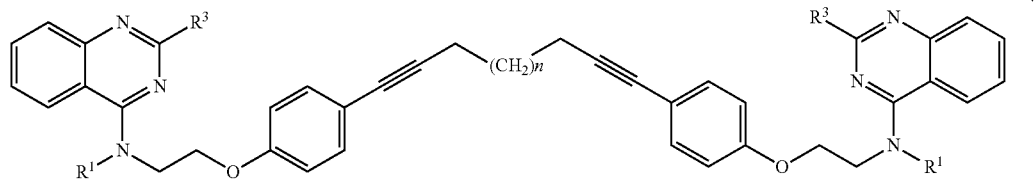
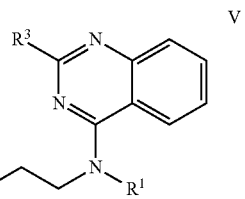

wherein $R^1$ and $R^3$ are as defined for Formula I above, n=0-8, and the compound has a diphenoxy alkynyl linker.

In some embodiments, the disclosed compounds having two substituted quinazoline groups conjugated via a linker may be described as having a Formula VI as follows:

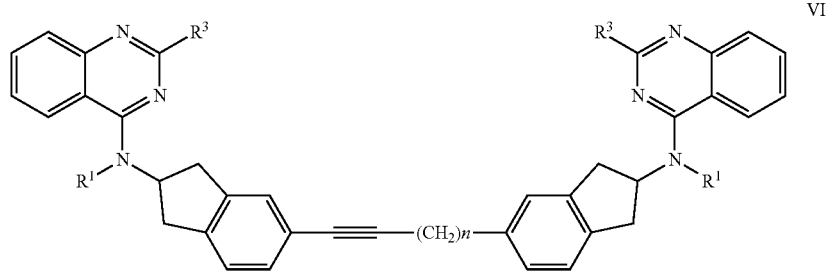

wherein $R^1$ and $R^3$ are as defined for Formula I above, n=1-10, and the compound has a di-2,3-dihydro-1H-indenyl alkynyl linker.

The compounds disclosed herein preferably modulate activity of glucocerebrosidase. Modulation may include inhibiting or decreasing glucocerebrosidase activity. Modulation also may include activating or increasing glucocerebrosidase activity. Glucocerebrosidase activity may be assessed utilizing methods known in the art and the methods disclosed herein, including the methods disclosed in the Examples provided herein. In some embodiments, the compounds decrease or increase glucocerebrosidase activity relative to a control (e.g., by at least about 10%, 20%, 30%, 40%, 50%, 60%, 70%, 80%, 90%, or more). In other embodiments, an $AC_{50}$ value or $IC_{50}$ value for the compound in regard to inhibition or activation of glucocerebrosidase may be determined and preferably the compound has an $AC_{50}$ or $IC_{50}$ value of less than about 10 µM, 5 µM, 1 µM, 0.5 µM 0.01 µM, 0.05 µM, or 0.001 µM.

The compounds disclosed herein (e.g., compounds of Formula I, II, III, IV, V, or VI) may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.) As used herein, formulae which do not specify the orientation at one or more chiral centers are meant to encompass all orientations and mixtures thereof.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that modulates glucocerebrosidase activity may be administered as a single compound or in combination with another compound that modulates glucocerebrosidase activity or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated glucocerebrosidase activity. For example, the pharmaceutical compositions may be utilized to treat patients having or at risk for acquiring a neurological disease or disorder, including degenerative neurological diseases or disorders such as Gaucher's disease and Parkinson's disease. Suitable patients include, for example mammals, such as humans and non-human primates (e.g., chimps) or other mammals (e g, dogs, cats, horses, rats, and mice). Suitable human patients may include, for example, those who have previously been determined to be at risk of having or developing a neurological disease or disorder, including degenerative neurological diseases or disorders such as Gaucher's disease and Parkinson's disease.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with superoxide dismutase mutations, including administering an effective amount of a compound that inhibits expression of the mutated form of superoxide dismutase.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The compounds disclosed in the present application may function as activators of glucocerebrosidase. For example, a compound disclosed herein may be reacted with glucocerebrosidase to prepare an activated glucocerebrosidase that is covalent attached to the compound. The activated glucocerebrosidase thusly formed may be prepared as a pharmaceutical composition to treat and/or prevent a disease or disorder that is associated with glucocerebrosidase activity as in enzyme replacement therapy, which is known in the art.

The following list of formulations is illustrative. These illustrative formulations may be suitable for preparing pharmaceutical compositions that include the disclosed compounds as "active ingredients." The following list of formulations is illustrative and should not be interpreted as limiting the present disclosure or claims in any way:

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

| | Weight % |
|---|---|
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules, each containing 80 mg medicament, are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| | |
|---|---|
| Active Ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8

An intravenous formulation containing 100 mg of medicament per 5 ml dose can be prepared as follows:

| | |
|---|---|
| Active Ingredient | 100 mg |
| Mannitol | 100 mg |
| 5N Sodium hydroxide | 200 ml |
| Purified water to total | 5 ml |

EXAMPLES

The followings Examples are illustrative only and are not intended to limit the scope of the claimed subject matter.

Example 1—Synthesis of Substituted Quinazoline Compounds

Compounds were prepared using Scheme 1 and Scheme 2 illustrated below:

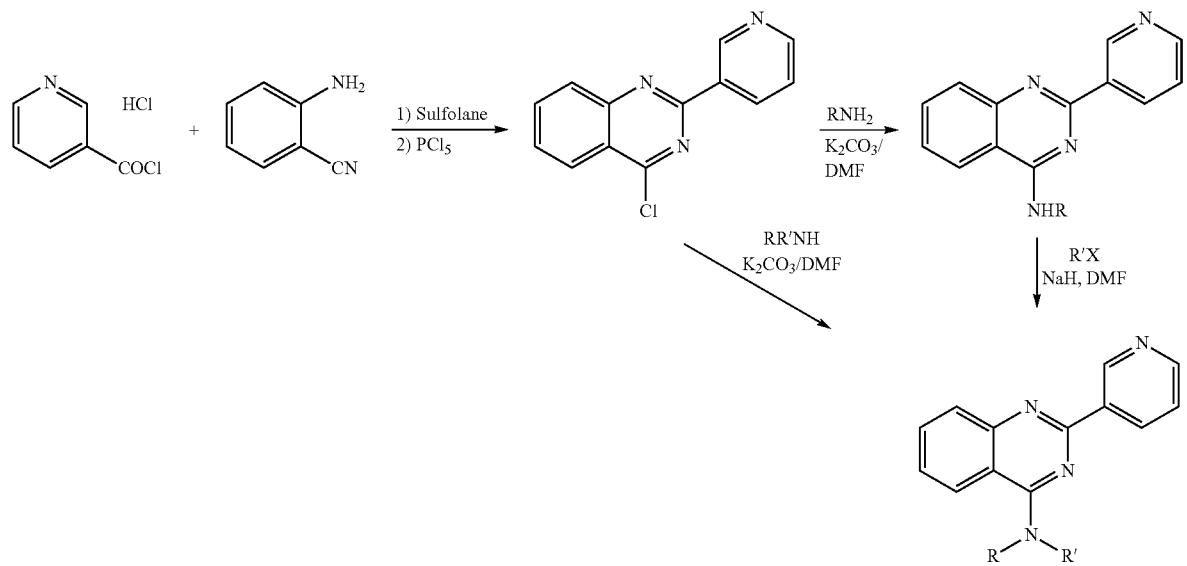

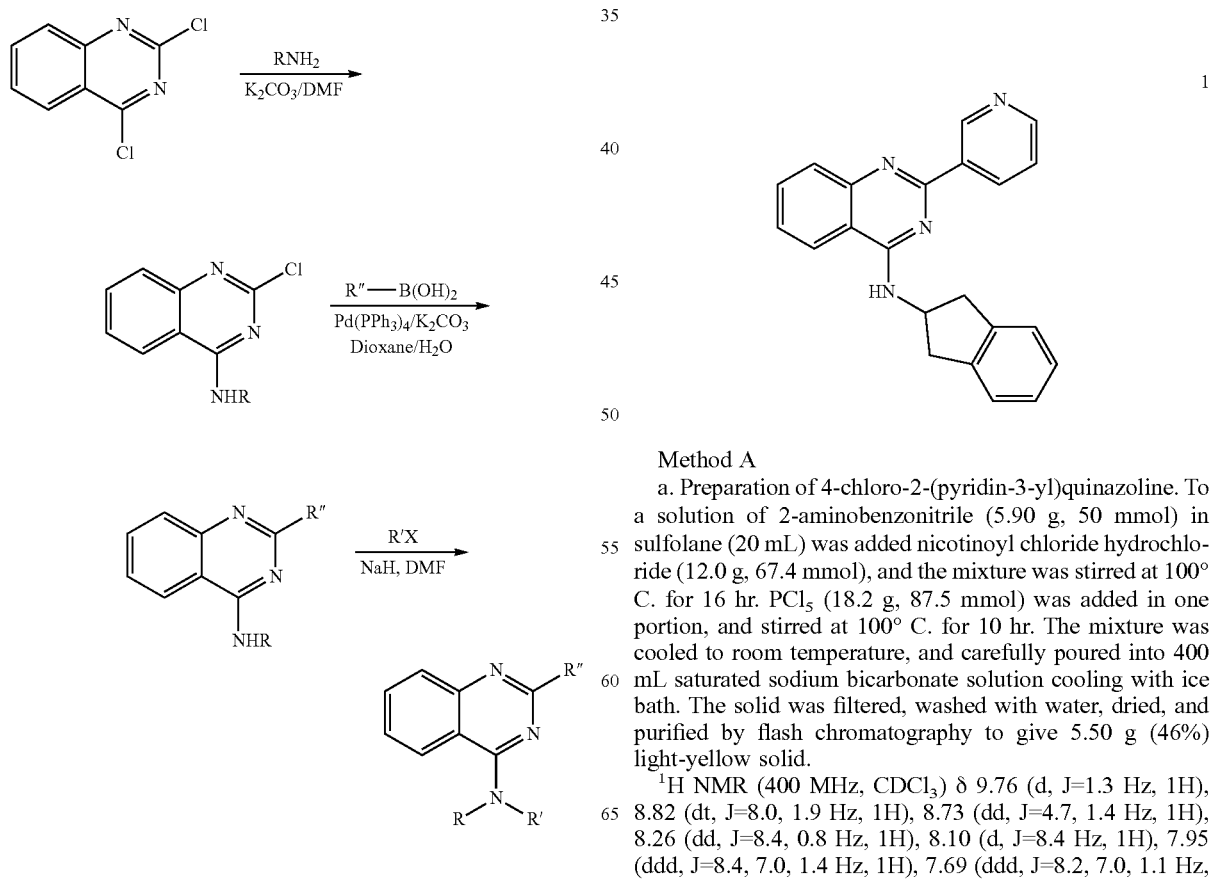

Preparation of (S)-2-(pyridin-3-yl)-N-(1,2,3,4-tetra-hydronaphthalen-2-yl)quinazolin-4-amine (1)

Method A a. Preparation of 4-chloro-2-(pyridin-3-yl)quinazoline. To a solution of 2-aminobenzonitrile (5.90 g, 50 mmol) in sulfolane (20 mL) was added nicotinoyl chloride hydrochloride (12.0 g, 67.4 mmol), and the mixture was stirred at 100° C. for 16 hr. $PCl_5$ (18.2 g, 87.5 mmol) was added in one portion, and stirred at 100° C. for 10 hr. The mixture was cooled to room temperature, and carefully poured into 400 mL saturated sodium bicarbonate solution cooling with ice bath. The solid was filtered, washed with water, dried, and purified by flash chromatography to give 5.50 g (46%) light-yellow solid.

$^1$H NMR (400 MHz, $CDCl_3$) δ 9.76 (d, J=1.3 Hz, 1H), 8.82 (dt, J=8.0, 1.9 Hz, 1H), 8.73 (dd, J=4.7, 1.4 Hz, 1H), 8.26 (dd, J=8.4, 0.8 Hz, 1H), 8.10 (d, J=8.4 Hz, 1H), 7.95 (ddd, J=8.4, 7.0, 1.4 Hz, 1H), 7.69 (ddd, J=8.2, 7.0, 1.1 Hz, 1H), 7.44 (dd, J=7.5, 4.8 Hz, 1H). $^{13}$C NMR: (100 MHz, CDCl$_3$) δ(ppm): 162.9, 158.3, 151.8, 151.7, 150.3, 136.1, 135.2, 132.4, 129.1, 128.9, 126.0, 123.5, 122.8.

b. Preparation of N-(2,3-dihydro-1H-inden-2-yl)-2-(pyridin-3-yl)quinazolin-4-amine (1). A mixture of 4-chloro-2-(pyridin-3-yl)quinazoline (120 mg, 0.5 mmol), 2,3-dihydro-1H-inden-2-amine (67 mg, 0.5 mmol), and potassium carbonate (69 mg, 0.5 mmol) in DMF (3 mL) was stirred at room temperature for 5 hr. Water (20 mL) was added, and the formed solid was filtered, washed with water, dried to give 150 mg (73%) off-white solid.

$^1$H NMR (500 MHz, CDCl$_3$) δ 9.78 (d, J=1.7 Hz, 1H), 8.84 (dd, J=7.9, 1.7 Hz, 1H), 8.69 (d, J=4.7 Hz, 1H), 7.93 (d, J=8.3 Hz, 1H), 7.77-7.70 (m, 1H), 7.68 (d, J=8.1 Hz, 1H), 7.47-7.37 (m, 2H), 7.32-7.27 (m, 2H), 7.25-7.20 (m, 2H), 6.04 (s, 1H), 5.37-5.29 (m, 1H), 3.60 (dd, J=16.2, 7.2 Hz, 2H), 3.08 (dd, J=16.2, 4.8 Hz, 2H). $^{13}$C NMR (125 MHz, CDCl$_3$) δ 159.4, 158.6, 150.7, 150.3, 141.1, 135.8, 134.4, 132.9, 128.9, 127.0, 126.0, 125.1, 123.3, 120.7, 113.9, 52.6, 40.3. ESI-MS m/z: 339 (M+H)$^+$.

Method B a. Preparation of 2-chloro-N-(2,3-dihydro-1H-inden-2-yl)quinazolin-4-amine. A mixture of 2,4-dichloroquinazoline (398 mg, 2.0 mmol), 2,3-dihydro-1H-inden-2-amine (266 mg, 2.0 mmol), and potassium carbonate (276 mg, 2.0 mmol) in DMF (5 mL) was stirred at room temperature for 5 hr. Water (20 mL) was added, and the formed solid was filtered, washed with water, dried to give 390 mg (66%) off-white solid.

$^1$H NMR (500 MHz, CDCl$_3$) δ 7.76 (d, J=8.2 Hz, 1H), 7.74-7.69 (m, 1H), 7.60 (d, J=8.2 Hz, 1H), 7.41 (t, J=7.4 Hz, 1H), 7.30-7.26 (m, 2H), 7.24-7.19 (m, 2H), 6.08 (d, J=6.7 Hz, 1H), 5.27-5.15 (m, 1H), 3.53 (dd, J=16.2, 7.0 Hz, 2H), 3.00 (dd, J=16.2, 4.0 Hz, 2H). $^{13}$C NMR (125 MHz, CDCl$_3$) δ 160.6, 157.8, 151.0, 140.7, 133.6, 128.0, 127.1, 126.2, 125.1, 120.8, 113.3, 52.6, 40.2.

b. Preparation of N-(2,3-dihydro-1H-inden-2-yl)-2-(pyridin-3-yl)quinazolin-4-amine (1). A mixture of 2-chloro-N-(2,3-dihydro-1H-inden-2-yl)quinazolin-4-amine (148 mg, 0.5 mmol), 3-pyridinylboronic acid (62 mg, 0.5 mmol), Pd(PPh$_3$)$_4$ (58 mg, 0.05 mmol), potassium carbonate (276 mg, 2.0 mmol) in Dioxane (10 mL) and water (1.5 mL) was heated at 85 r under argon atmosphere for 16 hr. Water (5 mL) was added, and the mixture was extracted with EtOAc (25 mL×3). The combined organic phase was washed with brine (15 mL), dried (Na$_2$SO$_4$), filtered, evaporated, and purified with flash chromatography to give 132 mg (78%) off white solid.

Preparation of (S)—N-methyl-2-(pyridin-3-yl)-N-(1,2,3,4-tetrahydronaphthalen-2-yl)quinazolin-4-amine (2)

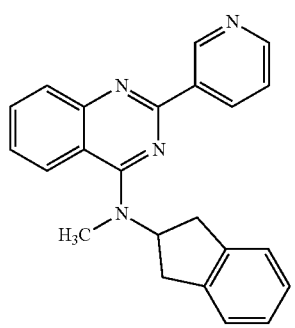

To a solution of (S)-2-(pyridin-3-yl)-N-(1,2,3,4-tetrahydronaphthalen-2-yl)quinazolin-4-amine (70 mg, 0.2 mmol) in DMF (3 mL) was added NaH (60%) (10 mg, 0.25 mmol) at room temperature, and stirred for 30 min. Methylene iodide (16 uL, 0.25 mmol) was added to the mixture, and stirred overnight. Water (20 mL) was added, and the formed solid was filtered, washed with water, dried to give 50 mg (69%) off-white solid.

Example 2—Glucocerebrosidase Activity Assay with Blue Substrate

The compounds in DMSO solution 0.5 μL/well were transferred to a black 96-well plate. The final titration was 24 nM to 50 μM, 12 concentrations, 2 times dilution. 33.5 μL of enzyme solution (7.5 nM final concentration) was transferred to the wells. After 5 min of incubation at room temperature, the enzyme reaction was initiated by the addition of 33 μL/well blue substrate. Final concentrations of the blue substrate (4MU-Glc) was 1.5 mM. The blue substrate reaction was terminated by the addition of 33 μL/well stop solution (1 M NaOH and 1 M glycine mixture, pH 10) after 30 min of incubation at 37° C. The fluorescence was then measured in the Biotek Synergy H1 multi-mode plate reader with Ex=365 nm and Em=440 nm.

Example 3—Fluorescence Polarization Assay

The fluorescent probe 3 (25 nL/well, 50 nM final concentration) was transferred to a 384-well black plate using a Labcyte Echo 550 Liquid Handler system. The 25 μL/well enzyme dilutions with GCase enzyme activity buffer were added to the plate, which was shaken at room temperature in dark for 20 min. The final titration was 5 nM to 10 μM, 10 concentrations, 2 times dilution. The fluorescence polarization was measured in Molecular Devices Analyst GT with Ex=535 nm and Em=580 nm, G Factor=1.05.

Example 4—Compound High Throughput Screening (HTS) by Fluorescence Polarization

The enzyme in GCase enzyme activity buffer (25 μL/well) was added to a 384-well black plate. The fluorescent probe 3 (25 nL/well, 50 nM final concentration) was transferred to a 384-well black plate using a Labcyte Echo 550 Liquid Handler system. Compounds in DMSO stock solution (50 nL) were transferred to the plate. The plate was shaken at room temperature in dark for 20 min. The final concentration was 19.5 nM to 10 μM, 10 concentrations, 2 times dilution. The fluorescence polarization was measured in a Molecular Devices Analyst GT with Ex=535 nm and Em=580 nm, G Factor=1.05.

Example 5—Preparation of the Compound-Activated Glucocerebrosidase

To the recombinant wild type enzyme (22 μM, 95 μL, 1 equiv) in 0.1 M phosphate buffer (pH 7.2) was added 2,5-dioxopyrrolidin-1-yl 3-(2-(2-(4-(4-(2,4-dimethylpyrrolo[1,2-a]pyrimidine-8-carboxamido)phenyl)-1H-1,2,3-triazol-1-yl)ethoxy)ethoxy)propanoate (4) in DMSO (0.89 mM, 5 μL, 2 equiv) in one portion, and was vortexed for 5 sec immediately. At indicated time points, the reaction solution (2 μL) was sampled and diluted (1:3125 dilution) into the assay buffer (50 mM citric acid, 176 mM K$_2$HPO$_4$, and 0.01% Tween-20 at pH 5.9). After 2 h the reaction solution was dialyzed three times with 0.1 M phosphate buffer (pH 7.2). The enzyme was adjusted to the same concentration and sampled for activity. The dilution solutions were assayed with three substrates, resorufin substrate, 4-MU substrate, and natural substrate using the methods described in the examples above without adding compounds.

Example 6—Synthesis and Testing of Additional Compounds

Additional compounds were prepared and tested according to the procedures provided in the examples above. Dose-response curves were prepared to determine $IC_{50}$ or $AC_{50}$ and compared to the known glucocerebrosidase activator NCGC00188758 (see Aflaki et al., Sci. Transl. Med. 6, 240ra273 (2014)). Results are shown in the following table.

Table of Substituted Quinazoline Compounds

| No. | Structures | MW | $IC_{50}$ or $AC_{50}$ (μM) | 1H NMR | 13C NMR | Mass |
|---|---|---|---|---|---|---|
| 1 | 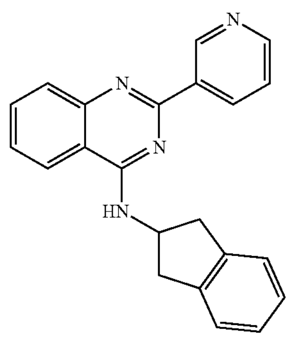 [SMILES: c1cncc(-c2nc(NC3Cc4ccccc4C3)c3ccccc3n2)c1] | 338 | 0.007 (inh) | $^1$H NMR (500 MHz, CDCl$_3$) δ 9.78 (d, J = 1.7 Hz, 1H), 8.84 (dd, J = 7.9, 1.7 Hz, 1H), 8.69 (d, J = 4.7 Hz, 1H), 7.93 (d, J = 8.3 Hz, 1H), 7.77-7.70 (m, 1H), 7.68 (d, J = 8.1 Hz, 1H), 7.47-7.37 (m, 2H), 7.32-7.27 (m, 2H), 7.25-7.20 (m, 2H), 6.04 (s, 1H), 5.37-5.29 (m, 1H), 3.60 (dd, J = 16.2, 7.2 Hz, 2H), 3.08 (dd, J = 16.2, 4.8 Hz, 2H). | $^{13}$C NMR (125 MHz, CDCl$_3$) δ 159.4, 158.6, 150.7, 150.3, 141.1, 135.8, 134.4, 132.9, 128.9, 127.0, 126.0, 125.1, 123.3, 120.7, 113.9, 52.6, 40.3, | ESI-MS m/z: 339 (M + H)$^+$ |
| 2 | 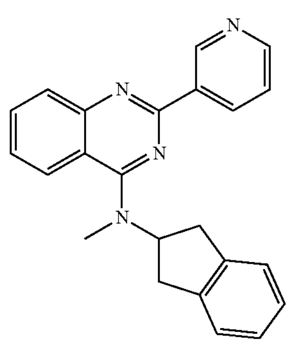 [SMILES: CN(c1nc(-c2cccnc2)nc2ccccc12)C1Cc2ccccc2C1] | 352 | 2.15 (inh) | $^1$H NMR (500 MHz, CDCl$_3$) δ 9.74 (d, J = 1.5 Hz, 1H), 8.77 (d, J = 8.0 Hz, 1H), 8.68 (dd, J = 4.7, 1.5 Hz, 1H), 8.04 (d, J = 7.9 Hz, 1H), 7.96 (d, J = 8.3 Hz, 1H), 7.78-7.69 (m, 1H), 7.45-7.41 (m, 1H), 7.39 (dd, J = 7.9, 4.8 Hz, 1H), 7.29 (dd, J = 5.2, 3.4 Hz, 2H), 7.25-7.20 (m, 2H), 5.66-5.58 (m, 1H), 3.47 (dd, J = 16.4, 8.6 Hz, 2H), 3.35-3.26 (m, 5H). | $^{13}$C NMR (125 MHz, CDCl$_3$) δ 164.7, 157.5, 153.1, 150.8, 150.4, 141.3, 135.7, 134.3, 132.5, 129.0, 126.9, 125.5, 124.8, 124.7, 123.3, 115.7, 60.2, 36.4, 35.6 | ESI-MS m/z: 353 (M + H)$^+$ |
| 3 | 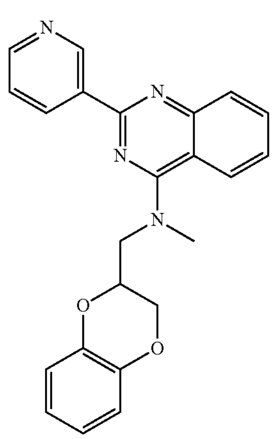 [SMILES: CN(CC1COc2ccccc2O1)c1nc(-c2cccnc2)nc2ccccc12] | 384 | 1.78 (act) | $^1$H NMR (500 MHz, CDCl$_3$) δ 9.67 (s, 1H), 8.74 (dt, J = 7.9, 1.7 Hz, 1H), 8.69 (d, J = 3.5 Hz, 1H), 8.14 (d, J = 8.5 Hz, 1H), 7.95 (d, J = 8.4 Hz, 1H), 7.78-7.68 (m, 1H), 7.45-7.37 (m, 2H), 6.91-6.81 (m, 4H), 4.88-4.75 (m, 1H), 4.38 (dd, J = 11.5, 2.3 Hz, 1H), 4.32 (dd, J = 14.3, 4.5 Hz, 1H), 4.17-4.14 (m, 1H), 4.13 (d, J = 6.4 Hz, 1H), 3.67 (s, 3H). | 163.1, 157.2, 153.2, 150.8, 150.1, 143.2, 142.7, 135.7, 134.2, 132.6, 129.0, 125.6, 124.9, 123.4, 121.9, 121.7, 117.5, 117.4, 115.1, 71.9, 66.1, 53.1, 43.2, | ESI-MS m/z: 385 (M + H)$^+$ |

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 4 | 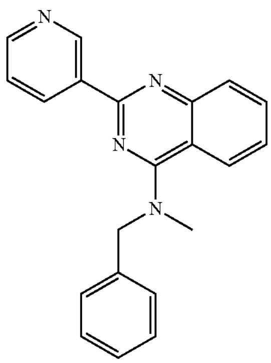 [SMILES: CN(Cc1ccccc1)c1nc(-c2cccnc2)nc2ccccc12] | 326 | NA | $^1$H NMR (500 MHz, CDCl$_3$) δ 9.73 (d, J = 1.8 Hz, 1H), 8.79 (dt, J = 7.9 Hz, 1.7 Hz, 1H), 7.96 (dd, J = 8.2, 4.4 Hz, 2H), 7.76-7.68 (m, 1H), 7.45-7.38 (m, 5H), 7.37-7.30 (m, 2H), 5.07 (s, 2H), 3.40 (s, 3H). | 163.9, 157.5, 152.9, 150.8, 150.3, 137.4, 135.8, 134.2, 132.5, 129.0, 128.9, 127.6, 127.3, 125.2, 125.0, 123.2, 115.0, 57.1, 39.7, | ESI-MS m/z: 327 (M + H)$^+$ |
| 5 | 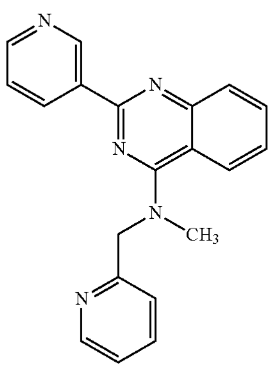 [SMILES: CN(Cc1ccccn1)c1nc(-c2cccnc2)nc2ccccc12] | 327 | 35.48 (act) | $^1$H NMR (400 MHz, CDCl$_3$) δ 9.66 (d, J = 1.6 Hz, 1H), 8.75 (dt, J = 7.9, 1.9 Hz, 1H), 8.71-8.62 (m, 2H), 8.05 (dd, J = 8.5, 0.8 Hz, 1H), 7.97 (d, J = 8.2 Hz, 1H), 7.80-7.64 (m, 2H), 7.45 (d, J = 7.8 Hz, 1H), 7.41-7.30 (m, 2H), 7.26-7.22 (m, 1H), 5.17 (s, 2H), 3.52 (s, 3H). | $^{13}$C NMR (100 MHz, CDCl$_3$) δ 163.5, 157.7, 157.4, 153.0, 150.7, 150.2, 149.8, 137.1, 135.7, 134.2, 132.5, 128.9, 125.2, 125.0, 123.2, 122.5, 121.5, 115.0, 58.9, 40.4 | ESI-MS m/z: 328 (M + H)$^+$ |
| 6 | 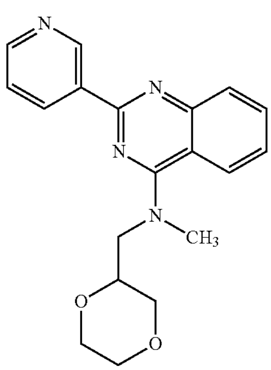 [SMILES: CN(CC1COCCO1)c1nc(-c2cccnc2)nc2ccccc12] | 336 | 11.22 (act) | $^1$H NMR (400 MHz, CDCl$_3$) δ 9.68 (s, 1H), 8.76 (d, J = 7.9 Hz, 1H), 8.68 (d, J = 3.5 Hz, 1H), 8.14 (d, J = 8.0 Hz, 1H), 7.96 (d, J = 8.4 Hz, 1H), 7.78-7.67 (m, 1H), 7.45-7.36 (m, 2H), 4.22-4.12 (m, 1H), 4.09 (dd, J = 14.2, 4.0 Hz, 1H), 3.91 (dd, J = 11.5, 2.5 Hz, 1H), 3.85-3.68 (m, 4H), 3.65 (dd, J = 11.2, 2.9 Hz, 1H), 3.60 (s, 3H), 3.43 (dd, J = 11.5, 10.1 Hz, 1H). | $^{13}$C NMR (100 MHz, CDCl$_3$) δ 163.2, 157.2, 153.1, 150.7, 150.1, 135.6, 134.2, 132.4, 128.8, 125.7, 124.7, 123.2, 115.1, 74.4, 69.4, 66.8, 66.5, 53.9, 42.6, | ESI-MS m/z: 337 (M + H)$^+$ |
| 7 | 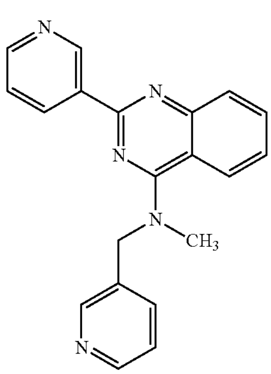 [SMILES: CN(Cc1cccnc1)c1nc(-c2cccnc2)nc2ccccc12] | 327 | 12.59 (act) | $^1$H NMR (400 MHz, CDCl$_3$) δ 9.70 (d, J = 1.6 Hz, 1H), 8.77 (d, J = 8.0 Hz, 1H), 8.70 (d, J = 1.5 Hz, 1H), 8.68 (dd, J = 4.8, 1.6 Hz, 1H), 8.59 (dd, J = 4.7, 1.0 Hz, 1H), 7.99 (dd, J = 8.7, 0.8 Hz, 2H), 7.81-7.71 (m, 2H), 7.44-7.36 (m, 2H), 7.32 (dd, J = 7.8, 4.9 Hz, 1H), 5.11 (s, 2H), 3.43 (s, 3H). | $^{13}$C NMR (100 MHz, CDCl$_3$) δ 163.9, 157.4, 153.0, 150.8, 150.1, 149.3, 149.2, 135.8, 135.3, 134.1, 133.1, 132.8, 129.1, 125.2, 125.1, 123.9, 123.3, 115.0, 54.3, 40.3, | ESI-MS m/z: 328 (M + H)$^+$ |

-continued

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 8 | 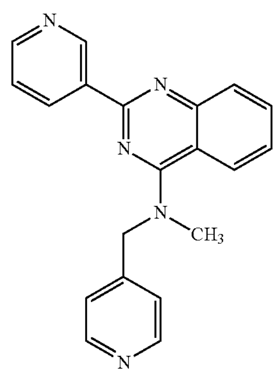 [SMILES: CN(Cc1ccncc1)c1nc(-c2cccnc2)nc2ccccc12] | 327 | 15.85 (act) | $^1$H NMR (400 MHz, CDCl$_3$) δ 9.66 (d, J = 1.2 Hz, 1H), 8.73 (dt, J = 7.9, 1.9 Hz, 1H), 8.67 (dd, J = 4.8, 1.6 Hz, 1H), 8.64-8.61 (m, 2H), 7.96 (dd, J = 17.9, 8.4 Hz, 2H), 7.80-7.70 (m, 1H), 7.44-7.31 (m, 4H), 5.06 (s, 2H), 3.45 (s, 3H). | $^{13}$C NMR (100 MHz, CDCl$_3$) δ 163.8, 157.4, 153.0, 150.9, 150.4, 150.2, 146.9, 135.7, 134.0, 132.8, 129.2, 125.3, 124.9, 123.3, 122.3, 115.0, 56.1, 40.4, | ESI-MS m/z: 328 (M + H)$^+$ |
| 9 | 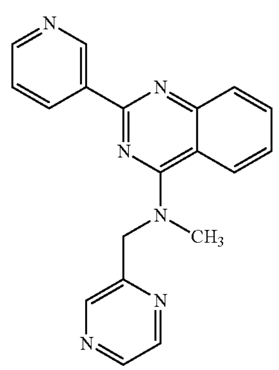 [SMILES: CN(Cc1cnccn1)c1nc(-c2cccnc2)nc2ccccc12] | 328 | 14.13 (act) | $^1$H NMR (400 MHz, CDCl$_3$) δ 9.60 (s, 1H), 8.74 (s, 1H), 8.71-8.62 (m, 2H), 8.58 (d, J = 1.5 Hz, 1H), 8.52 (s, 1H), 8.10 (d, J = 8.5 Hz, 1H), 7.98 (d, J = 8.4 Hz, 1H), 7.81-7.70 (m, 1H), 7.45-7.32 (m, 2H), 5.21 (s, 2H), 3.58 (s, 3H). | 163.4, 157.4, 153.5, 153.0, 150.8, 150.1, 144.3, 144.0, 143.7, 135.7, 134.0, 132.7, 129.1, 125.2, 123.2, 115.0, 56.4, 41.3, | ESI-MS m/z: 329 (M + H)$^+$ |
| 10 | 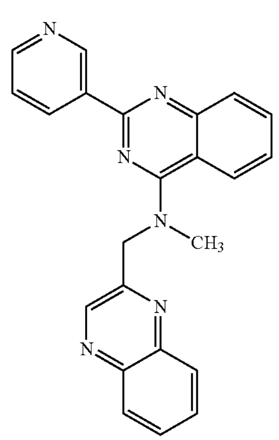 [SMILES: CN(Cc1cnc2ccccc2n1)c1nc(-c2cccnc2)nc2ccccc12] | 378 | 0.89 (act) | $^1$H NMR (500 MHz, CDCl$_3$) δ 9.65 (s, 1H), 9.02 (s, 1H), 8.70 (d, J = 7.7 Hz, 1H), 8.65 (d, J = 2.4 Hz, 1H), 8.14 (d, J = 8.4 Hz, 1H), 8.10 (d, J = 8.1 Hz, 2H), 7.99 (d, J = 8.3 Hz, 1H), 7.83-7.72 (m, 3H), 7.42 (t, J = 7.6 Hz, 1H), 7.35 (dd, J = 7.2, 5.0 Hz, 1H), 5.41 (s, 2H), 3.63 (s, 3H). | $^{13}$C NMR (100 MHz, CDCl3) δ 163.5, 157.4, 153.2, 153.1, 150.8, 150.1, 144.7, 142.1, 135.7, 134.0, 132.8, 130.4, 129.9, 129.4, 129.2, 129.1, 125.3, 125.2, 123.3, 115.0, 57.0, 41.4, | ESI-MS m/z: 379 (M + H)$^+$ |

-continued

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 11 | 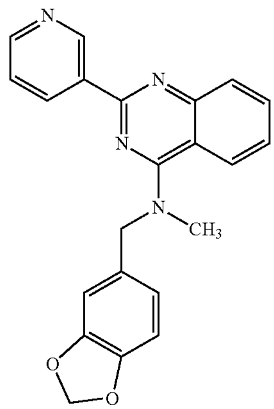 [SMILES: CN(Cc1ccc2c(c1)OCO2)c1nc(-c2cccnc2)nc2ccccc12] | 370 | 1.00 (act) | $^1$H NMR (400 MHz, CDCl$_3$) δ 9.74 (s, 1H), 8.81 (dt, J = 8.0, 1.9 Hz, 1H), 8.68 (d, J = 3.3 Hz, 1H), 7.97 (d, J = 8.8 Hz, 2H), 7.76-7.66 (m, 1H), 7.40 (dd, J = 7.8, 4.8 Hz, 1H), 7.37-7.32 (m, 1H), 6.89 (d, J = 9.4 Hz, 2H), 6.83 (d, J = 7.8 Hz, 1H), 5.97 (s, 2H), 4.98 (s, 2H), 3.37 (s, 3H). | $^{13}$C NMR (100 MHz, CDCl$_3$) δ 163.8, 157.5, 152.9, 150.8, 150.3, 148.4, 147.2, 135.8, 132.5, 131.2, 128.9, 125.2, 125.0, 123.3, 120.7, 115.1, 108.6, 107.8, 101.2, 56.7, 39.6, | ESI-MS m/z: 371 (M + H)$^+$ |
| 12 | 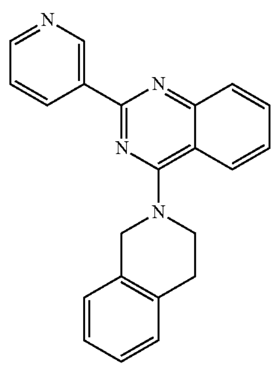 [SMILES: c1cncc(-c2nc(N3CCc4ccccc4C3)c3ccccc3n2)c1] | 338 | NA | $^1$H NMR (400 MHz, CDCl$_3$) δ 9.79 (s, 1H), 8.83 (d, J = 7.9 Hz, 1H), 8.71 (s, 1H), 7.99 (dd, J = 14.1, 8.4 Hz, 2H), 7.76 (t, J = 7.8 Hz, 1H), 7.53-7.37 (m, 2H), 7.23 (s, 4H), 5.07 (s, 2H), 4.15 (t, J = 5.7 Hz, 2H), 3.22 (t, J = 5.6 Hz, 2H). | $^{13}$C NMR (100 MHz, CDCl$_3$) δ 164.2, 157.6, 152.8, 150.8, 150.4, 135.8, 134.8, 133.9, 132.6, 129.0, 128.9, 126.9, 126.6, 126.5, 125.2, 125.0, 123.3, 115.6, 51.4, 48.2, 29.0, | ESI-MS m/z: 339 (M + H)$^+$ |
| 13 | 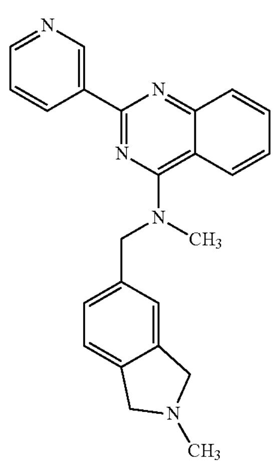 [SMILES: CN1Cc2ccc(CN(C)c3nc(-c4cccnc4)nc4ccccc34)cc2C1] | 381 | 44.67 (act) | $^1$H NMR (400 MHz, CDCl$_3$) δ 9.73 (d, J = 1.5 Hz, 1H), 8.79 (dt, J = 8.0, 1.9 Hz, 1H), 8.68 (dd, J = 4.8, 1.7 Hz, 1H), 7.99-7.91 (m, 2H), 7.77-7.68 (m, 1H), 7.39 (dd, J = 7.9, 4.8 Hz, 1H), 7.36-7.29 (m, 1H), 7.28-7.21 (m, 3H), 5.05 (s, 2H), 3.97 (d, J = 6.7 Hz, 4H), 3.38 (s, 3H), 2.64 (s, 3H). | $^{13}$C NMR (100 MHz, CDCl$_3$) δ 163.9, 157.6, 153.0, 150.8, 150.3, 136.2, 135.7, 134.3, 132.5, 128.9, 126.1, 125.2, 125.0, 123.2, 122.8, 121.1, 115.1, 60.9, 60.8, 57.1, 42.4, 39.6, | ESI-MS m/z: 382 (M + H)$^+$ |

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 14 | 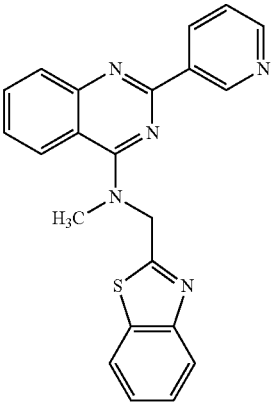 [SMILES: CN(Cc1nc2ccccc2s1)c1nc(-c2cccnc2)nc2ccccc12] | 383 | 1.12 (act) | $^1$H NMR (400 MHz, CDCl$_3$) δ 9.80 (s, 1H), 8.84 (d, J = 8.0 Hz, 1H), 8.69 (d, J = 3.6 Hz, 1H), 8.13 (d, J = 8.3 Hz, 1H), 8.02 (dd, J = 16.6, 8.2 Hz, 2H), 7.81 (d, J = 7.9 Hz, 1H), 7.78 (d, J = 8.1 Hz, 1H), 7.48 (d, J = 7.3 Hz, 1H), 7.46-7.34 (m, 3H), 5.44 (s, 2H), 3.58 (s, 3H). | $^{13}$C NMR (100 MHz, CDCl$_3$) δ 168.5, 163.2, 157.2, 153.1, 152.8, 150.9, 150.4, 135.9, 135.8, 133.8, 132.9, 129.1, 126.2, 125.4, 125.3, 125.3, 123.3, 123.0, 121.9, 115.0, 54.8, 40.8, | ESI-MS m/z: 384 (M + H)$^+$ |
| 15 | 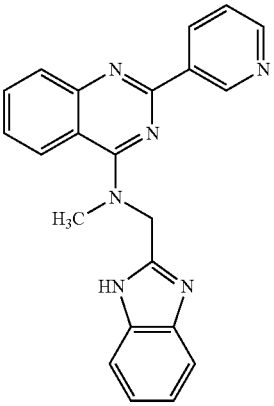 [SMILES: CN(Cc1nc2ccccc2[nH]1)c1nc(-c2cccnc2)nc2ccccc12] | 366 | 8.91 (act) | $^1$H NMR (400 MHz, CDCl$_3$) δ 9.61 (s, 1H), 8.66 (dt, J = 8.0, 1.9 Hz, 1H), 8.61-8.48 (m, 1H), 8.03 (d, J = 8.3 Hz, 1H), 7.92 (d, J = 8.3 Hz, 1H), 7.79-7.68 (m, 1H), 7.57 (brs, 2H), 7.46-7.33 (m, 1H), 7.26-7.20 (m, 3H), 5.27 (s, 2H), 3.47 (s, 3H). | $^{13}$C NMR (100 MHz, CDCl$_3$) δ 163.4, 156.9, 152.9, 151.1, 150.7, 149.5, 135.5, 133.7, 133.2, 128.9, 125.6, 125.5, 123.4, 122.8, 114.9, 50.5, 40.7, | ESI-MS m/z: 367 (M + H)$^+$ |
| 16 | 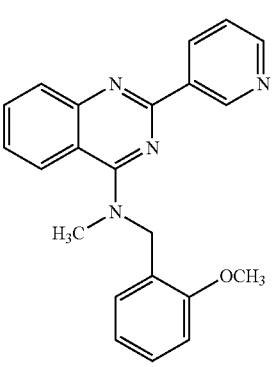 [SMILES: COc1ccccc1CN(C)c1nc(-c2cccnc2)nc2ccccc12] | 356 | 3.13 (act) | $^1$H NMR (500 MHz, CDCl$_3$) δ 9.73 (s, 1H), 8.79 (dt, J = 7.9, 1.8 Hz, 1H), 8.67 (d, J = 3.5 Hz, 1H), 7.94 (d, J = 8.2 Hz, 1H), 7.86 (d, J = 8.3 Hz, 1H), 7.74-7.63 (m, 1H), 7.43 (d, J = 7.4 Hz, 1H), 7.38 (dd, J = 7.9, 4.8 Hz, 1H), 7.35-7.30 (m, 1H), 7.30-7.23 (m, 1H), 7.00 (t, J = 7.4 Hz, 1H), 6.95 (d, J = 8.2 Hz, 1H), 5.00 (s, 2H), 3.82 (s, 3H), 3.38 (s, 3H). | $^{13}$C NMR (125 MHz, CDCl$_3$) δ 164.1, 157.5, 152.8, 150.7, 150.3, 135.7, 134.4, 132.3, 128.7, 128.6, 127.6, 125.2, 125.2, 124.8, 123.2, 120.8, 115.2, 110.3, 55.3, 53.3, 39.4, | ESI-MS m/z: 357 (M + H)$^+$ |

-continued

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 17 | 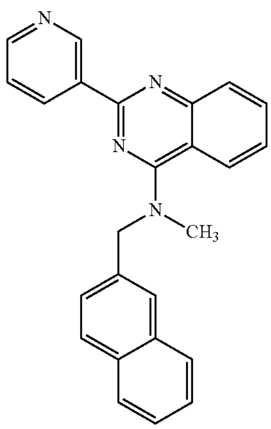 [SMILES: CN(Cc1ccc2ccccc2c1)c1nc(-c2cccnc2)nc2ccccc12] | 376 | 1.56 (act) | $^1$H NMR (500 MHz, CDCl$_3$) δ 9.77 (s, 1H), 8.83 (d, J = 7.8 Hz, 1H), 8.69 (d, J = 3.5 Hz, 1H), 7.99 (d, J = 8.6 Hz, 2H), 7.95-7.78 (m, 4H), 7.78-7.67 (m, 1H), 7.58-7.44 (m, 3H), 7.41 (dd, J = 7.7, 4.9 Hz, 1H), 7.37-7.28 (m, 1H), 5.23 (s, 2H), 3.45 (s, 3H). | $^{13}$C NMR (125 MHz, CDCl$_3$) δ 164.0, 157.5, 152.9, 150.8, 150.3, 135.8, 134.9, 134.3, 133.6, 133.0, 132.6, 129.0, 128.9, 127.9, 126.6, 126.1, 125.9, 125.3, 125.2, 125.1, 123.3, 115.1, 57.4, 39.7, | ESI-MS m/z: 377 (M + H)$^+$ |
| 18 | 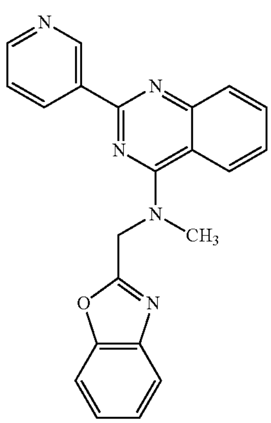 [SMILES: CN(Cc1nc2ccccc2o1)c1nc(-c2cccnc2)nc2ccccc12] | 367 | 11.22 (act) | $^1$H NMR (500 MHz, CDCl$_3$) δ 9.66 (d, J = 1.5 Hz, 1H), 8.73 (dt, J = 7.9, 1.8 Hz, 1H), 8.65 (dd, J = 4.8, 1.6 Hz, 1H), 8.21 (d, J = 7.9 Hz, 1H), 7.99 (d, J = 8.3 Hz, 1H), 7.82-7.75 (m, 1H), 7.75-7.70 (m, 1H), 7.59-7.51 (m, 1H), 7.50-7.44 (m, 1H), 7.38-7.30 (m, 3H), 5.25 (s, 2H), 3.71 (s, 3H). | $^{13}$C NMR (125 MHz, CDCl$_3$) δ 163.5, 163.1, 157.2, 153.0, 150.9, 150.7, 150.1, 141.1, 135.9, 134.0, 132.9, 129.1, 125.4, 125.3, 125.3, 124.7, 123.3, 120.2, 115.1, 110.8, 50.4, 41.7, | ESI-MS m/z: 368 (M + H)$^+$ |
| 19 | 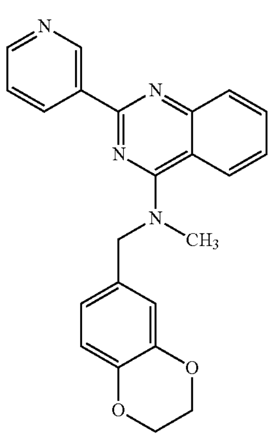 [SMILES: CN(Cc1ccc2c(c1)OCCO2)c1nc(-c2cccnc2)nc2ccccc12] | 384 | 3.98 (act) | $^1$H NMR (500 MHz, CDCl$_3$) δ 9.73 (s, 1H), 8.79 (d, J = 7.9 Hz, 1H), 8.67 (d, J = 4.6 Hz, 1H), 7.95 (t, J = 8.0 Hz, 2H), 7.74-7.66 (m, 1H), 7.39 (dd, J = 7.7, 4.9 Hz, 1H), 7.36-7.30 (m, 1H), 6.94 (s, 1H), 6.89 (s, 2H), 4.95 (s, 2H), 4.27 (s, 4H), 3.37 (s, 3H). | $^{13}$C NMR (125 MHz, CDCl$_3$) δ 163.8, 157.5, 153.0, 150.8, 150.3, 144.0, 143.1, 135.7, 134.3, 132.5, 130.6, 128.9, 125.2, 124.9, 123.2, 120.3, 117.7, 116.1, 115.1, 64.5, 64.4, 56.5, 39.5, | ESI-MS m/z: 385 (M + H)$^+$ |

| No. | Structures | MW | IC$_{50}$ or AC$_{50}$ (μM) | 1H NMR | 13C NMR | Mass |
|---|---|---|---|---|---|---|
| 20 | 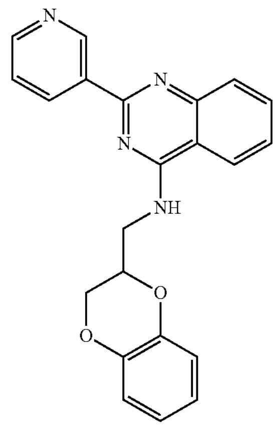 [SMILES: c1cncc(-c2nc(NCC3COc4ccccc4O3)c3ccccc3n2)c1] | 370 | 7.94 (inh) | $^1$H NMR (500 MHz, CDCl$_3$) δ 9.73 (d, J = 1.5 Hz, 1H), 8.79 (dt, J = 7.9, 1.9 Hz, 1H), 8.70 (dd, J = 4.7, 1.6 Hz, 1H), 7.99-7.90 (m, 1H), 7.82-7.75 (m, 2H), 7.54-7.47 (m, 1H), 7.42 (dd, J = 7.9, 4.8 Hz, 1H), 6.98-6.92 (m, 1H), 6.92-6.82 (m, 3H), 6.23 (t, J = 5.1 Hz, 1H), 4.66-4.60 (m, 1H), 4.43 (dd, J = 11.5, 2.3 Hz, 1H), 4.24 (ddd, J = 14.3, 6.1, 4.3 Hz, 1H), 4.16-4.08 (m, 2H). | $^{13}$C NMR (125 MHz, CDCl$_3$) δ 159.9, 158.5, 150.9, 150.5, 150.2, 143.2, 142.8, 135.7, 134.3, 133.1, 129.1, 126.3, 123.3, 121.8, 120.8, 117.4, 117.4, 113.9, 71.9, 66.0, 41.5, | ESI-MS m/z: 371 (M + H)$^+$ |
| 21 | 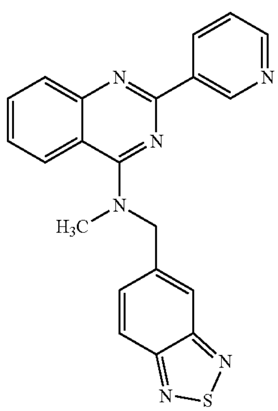 [SMILES: CN(Cc1ccc2nsnc2c1)c1nc(-c2cccnc2)nc2ccccc12] | 384 | 3.55 (act) | $^1$H NMR (500 MHz, CDCl$_3$) δ 9.70 (d, J = 1.6 Hz, 1H), 8.77 (dt, J = 7.9, 1.8 Hz, 1H), 8.67 (dd, J = 4.8, 1.6 Hz, 1H), 8.07-8.02 (m, 2H), 8.00 (t, J = 8.1 Hz, 2H), 7.79-7.70 (m, 1H), 7.64 (dd, J = 9.1, 1.4 Hz, 1H), 7.43-7.32 (m, 2H), 5.24 (s, 2H), 3.49 (s, 3H). | $^{13}$C NMR (125 MHz, CDCl$_3$) δ 163.9, 157.5, 155.2, 154.6, 153.1, 150.9, 150.3, 139.7, 135.7, 134.1, 132.8, 129.5, 129.2, 125.2, 125.0, 123.3, 122.2, 119.2, 115.1, 56.8, 40.3, | ESI-MS m/z: 385 (M + H)$^+$ |
| 22 | 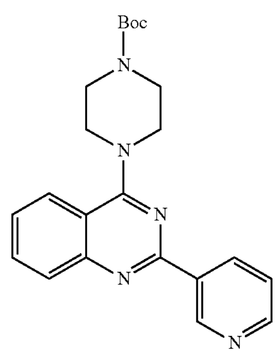 [SMILES: CC(C)(C)OC(=O)N1CCN(c2nc(-c3cccnc3)nc3ccccc23)CC1] | 391 | 10.00 (act) | $^1$H NMR (500 MHz, CDCl$_3$) δ 9.72 (s, 1H), 8.82-8.75 (m, 1H), 8.69 (dd, J = 4.7, 1.6 Hz, 1H), 7.98 (d, J = 8.4 Hz, 1H), 7.90 (d, J = 8.3 Hz, 1H), 7.83-7.73 (m, 1H), 7.50-7.43 (m, 1H), 7.43-7.36 (m, 1H), 3.84 (d, J = 4.6 Hz, 4H), 3.75-3.65 (m, 4H), 1.50 (d, J = 1.6 Hz, 9H). | $^{13}$C NMR (125 MHz, CDCl$_3$) δ 165.0, 157.6, 154.9, 152.8, 151.0, 150.3, 135.7, 134.0, 132.9, 129.2, 125.7, 124.8, 123.3, 115.6, 80.3, 49.9, 43.9, 28.5 | ESI-MS m/z: 392 (M + H)$^+$ |
| 23 | 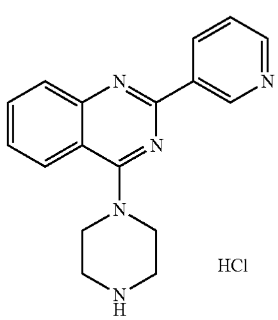 [SMILES: c1cncc(-c2nc(N3CCNCC3)c3ccccc3n2)c1 ; Cl] | 327 | 35.48 (inh) | $^1$H NMR (500 MHz, D$_2$O) δ 9.61 (d, J = 1.5 Hz, 1H), 9.31 (d, J = 8.3 Hz, 1H), 9.01 (d, J = 5.6 Hz, 1H), 8.26 (dd, J = 8.1, 5.9 Hz, 1H), 8.16 (d, J = 8.4 Hz, 1H), 8.06-7.99 (m, 1H), 7.96 (d, J = 8.2 Hz, 1H), 7.75 (t, J = 7.4 Hz, 1H), 4.57-4.48 (m, 4H), 3.57-3.48 (m, 4H). | $^{13}$C NMR (125 MHz, D$_2$O) δ 163.5, 151.2, 145.6, 144.6, 142.6, 142.1, 136.8, 131.6, 128.6, 127.7, 126.6, 120.4, 112.0, 45.9, 42.8 | ESI-MS m/z: 292 (M + H)$^+$ |

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 24 | 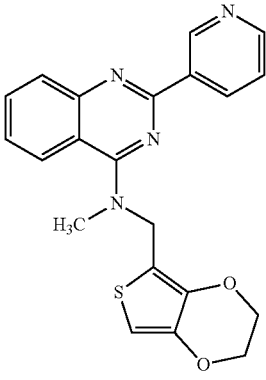 [SMILES: CN(Cc1scc2c1OCCO2)c1nc(-c2cccnc2)nc2ccccc12] | 390 | 2.00 (act) | $^1$H NMR (500 MHz, CDCl$_3$) δ 9.82 (d, J = 1.7 Hz, 1H), 8.87 (dt, J = 7.9, 1.7 Hz, 1H), 8.69 (dd, J = 4.7, 1.5 Hz, 1H), 8.09 (d, J = 8.4 Hz, 1H), 7.94 (d, J = 8.4 Hz, 1H), 7.78-7.65 (m, 1H), 7.45-7.32 (m, 2H), 6.23 (s, 1H), 5.05 (s, 2H), 4.25 (d, J = 4.7 Hz, 2H), 4.23-4.18 (m, 2H), 3.45 (s, 3H). | $^{13}$C NMR (125 MHz, CDCl$_3$) δ 163.5, 157.4, 153.0, 150.8, 150.6, 141.1, 140.2, 135.9, 134.1, 132.5, 128.9, 125.6, 124.7, 123.2, 115.1, 113.2, 99.1, 64.9, 64.8, 47.0, 39.9 | ESI-MS m/z: 391 (M + H)$^+$ |
| 25 | 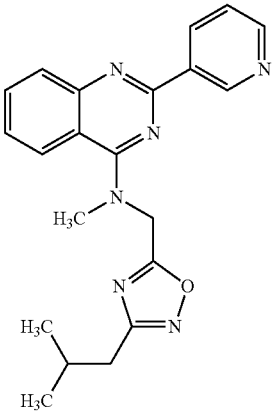 [SMILES: CC(C)Cc1noc(CN(C)c2nc(-c3cccnc3)nc3ccccc23)n1] | 374 | 35.48 (act) | $^1$H NMR (500 MHz, CDCl$_3$) δ 9.60 (d, J = 1.5 Hz, 1H), 8.66 (dd, J = 4.8, 1.7 Hz, 1H), 8.63 (dt, J = 7.9, 1.9 Hz, 1H), 8.14 (dd, J = 8.4, 0.7 Hz, 1H), 7.98 (dd, J = 8.4, 0.7 Hz, 1H), 7.77 (ddd, J = 8.3, 7.0, 1.3 Hz, 1H), 7.47 (ddd, J = 8.3, 7.0, 1.2 Hz, 1H), 7.36 (ddd, J = 7.9, 4.8, 0.7 Hz, 1H), 5.11 (s, 2H), 3.70 (s, 3H), 2.59 (d, J = 7.1 Hz, 2H), 2.16-2.05 (m, 1H), 0.90 (d, J = 6.7 Hz, 6H). | $^{13}$C NMR (125 MHz, CDCl$_3$) δ 176.2, 170.1, 163.2, 157.2, 153.0, 150.9, 150.2, 135.6, 133.7, 132.9, 129.2, 125.4, 125.2, 123.2, 115.0, 48.8, 42.2, 34.7, 27.1, 22.3, | ESI-MS m/z: 375 (M + H)$^+$ |
| 26 | 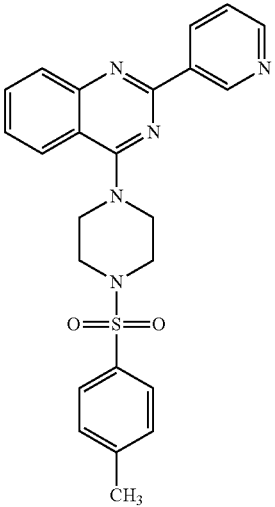 [SMILES: Cc1ccc(S(=O)(=O)N2CCN(c3nc(-c4cccnc4)nc4ccccc34)CC2)cc1] | 445 | 1.00 (act) | $^1$H NMR (500 MHz, CDCl$_3$) δ 9.66 (s, 1H), 8.75 (d, J = 7.9 Hz, 1H), 8.69 (d, J = 4.2 Hz, 1H), 7.96 (d, J = 8.4 Hz, 1H), 7.78 (d, J = 8.3 Hz, 1H), 7.77-7.72 (m, 1H), 7.68 (d, J = 7.9 Hz, 2H), 7.50-7.37 (m, 2H), 7.33 (d, J = 8.0 Hz, 2H), 3.94 (brs, 4H), 3.25 (brs, 4H), 2.41 (s, 3H). | $^{13}$C NMR (125 MHz, CDCl$_3$) δ 164.6, 157.4, 152.7, 150.9, 150.0, 144.1, 135.8, 133.9, 133.1, 132.5, 130.0, 129.3, 127.9, 125.9, 124.6, 123.4, 115.4, 49.2, 45.8, 21.6, | ESI-MS m/z: 446 (M + H)$^+$ |

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 27 | 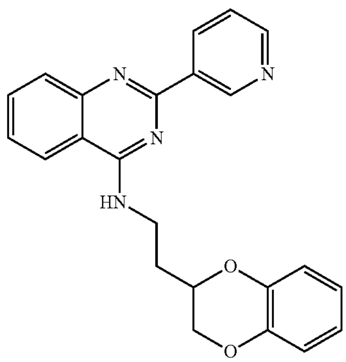 [SMILES: c1cncc(-c2nc(NCCC3COc4ccccc4O3)c3ccccc3n2)c1] | 384 | 0.60 (act) | $^1$H NMR (500 MHz, CDCl$_3$) δ 9.76 (d, J = 2.1 Hz, 1H), 8.81 (dt, J = 7.9, 1.9 Hz, 1H), 8.69 (dd, J = 4.8, 1.7 Hz, 1H), 7.93 (d, J = 8.3 Hz, 1H), 7.79-7.72 (m, 2H), 7.56-7.44 (m, 1H), 7.40 (dd, J = 7.9, 4.8 Hz, 1H), 6.99-6.81 (m, 4H), 6.36 (t, J = 5.0 Hz, 1H), 4.45-4.37 (m, 1H), 4.28 (dd, J = 11.3, 2.2 Hz, 1H), 4.18-4.09 (m, 1H), 4.09-3.98 (m, 2H), 2.28-2.19 (m, 1H), 2.15-2.05 (m, 1H). | $^{13}$C NMR (125 MHz, CDCl$_3$) δ 159.7, 158.7, 150.9, 150.4, 150.3, 143.3, 142.9, 135.7, 134.4, 132.9, 129.1, 126.1, 123.2, 121.8, 121.8, 120.6, 117.4, 117.3, 114.0, 72.4, 67.9, 38.4, 30.1, | ESI-MS m/z: 385 (M + H)$^+$ |
| 28 | 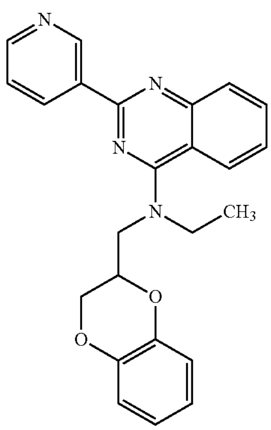 [SMILES: CCN(CC1COc2ccccc2O1)c1nc(-c2cccnc2)nc2ccccc12] | 398 | 2.82 (act) | $^1$H NMR (500 MHz, CDCl$_3$) δ 9.68 (d, J = 1.4 Hz, 1H), 8.75 (dt, J = 7.9, 1.8 Hz, 1H), 8.69 (dd, J = 4.7, 1.6 Hz, 1H), 7.98 (dd, J = 13.2, 8.4 Hz, 2H), 7.80-7.68 (m, 1H), 7.50-7.35 (m, 2H), 6.93-6.75 (m, 4H), 4.86-4.73 (m, 1H), 4.36 (dd, J = 11.4, 2.3 Hz, 1H), 4.23-4.11 (m, 2H), 4.06-3.81 (m, 3H), 1.50 (t, J = 7.1 Hz, 3H). | $^{13}$C NMR (125 MHz, CDCl$_3$) δ 163.4, 157.2, 152.9, 150.9, 150.1, 143.2, 142.8, 135.6, 134.2, 132.7, 129.2, 125.3, 124.7, 123.4, 121.9, 121.6, 117.5, 117.3, 115.5, 71.5, 66.2, 50.3, 49.2, 14.2, | ESI-MS m/z: 399 (M + H)$^+$ |
| 29 | 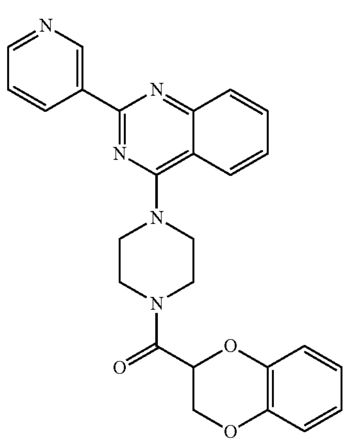 [SMILES: O=C(C1COc2ccccc2O1)N1CCN(c2nc(-c3cccnc3)nc3ccccc23)CC1] | 453 | 2.24 (inh) | $^1$H NMR (500 MHz, CDCl$_3$) δ 9.72 (d, J = 1.5 Hz, 1H), 8.78 (dt, J = 7.9, 1.9 Hz, 1H), 8.69 (dd, J = 4.8, 1.7 Hz, 1H), 8.00 (d, J = 8.3 Hz, 1H), 7.91 (d, J = 7.8 Hz, 1H), 7.82-7.74 (m, 1H), 7.53-7.45 (m, 1H), 7.40 (dd, J = 7.9, 4.8 Hz, 1H), 6.97-6.81 (m, 4H), 4.89 (dd, J = 8.0, 2.5 Hz, 1H), 4.52 (dd, J = 11.9, 2.5 Hz, 1H), 4.37 (dd, J = 11.9, 8.0 Hz, 1H), 4.13-3.70 (m, 8H). | $^{13}$C NMR (125 MHz, CDCl$_3$) δ 165.4, 164.9, 157.7, 152.8, 151.1, 150.3, 143.4, 142.5, 135.7, 133.9, 133.1, 129.4, 126.0, 124.6, 123.3, 122.5, 121.7, 117.6, 117.4, 115.6, 70.9, 65.2, 50.0, 49.7, 45.6, 42.0, | ESI-MS m/z: 454 (M + H)$^+$ |

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 30 | 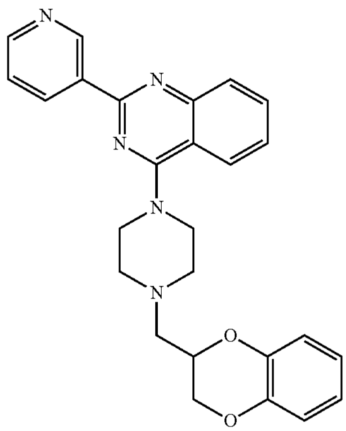 [SMILES: c1cncc(-c2nc(N3CCN(CC4COc5ccccc5O4)CC3)c3ccccc3n2)c1] | 439 | 3.13 (act) | $^1$H NMR (500 MHz, CDCl$_3$) δ 9.73 (d, J = 1.3 Hz, 1H), 8.79 (dt, J = 8.0, 1.7 Hz, 1H), 8.69 (dd, J = 4.7, 1.4 Hz, 1H), 7.97 (d, J = 8.3 Hz, 1H), 7.90 (d, J = 8.2 Hz, 1H), 7.77-7.71 (m, 1H), 7.48-7.36 (m, 2H), 6.97-6.73 (m, 4H), 4.45-4.31 (m, 2H), 4.18 (s, 1H), 4.06 (dd, J = 11.2, 7.1 Hz, 1H), 3.91 (t, J = 4.6 Hz, 4H), 2.91-2.60 (m, 5H). | 164.8, 157.7, 152.8, 150.9, 150.3, 143.3, 143.1, 135.7, 134.1, 132.7, 129.1, 125.4, 115.0, 123.3, 121.7, 121.5, 117.5, 117.2, 115.6, 71.4, 66.9, 58.6, 53.9, 49.8, 49.5, | ESI-MS m/z: 440 (M + H)$^+$ |
| 31 | 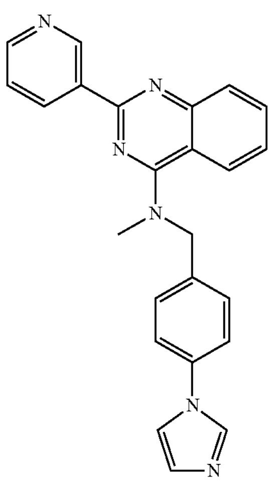 [SMILES: CN(Cc1ccc(-n2ccnc2)cc1)c1nc(-c2cccnc2)nc2ccccc12] | 392 | 19.95 (act) | $^1$H NMR (500 MHz, CDCl$_3$) δ 9.70 (s, 1H), 8.78 (d, J = 7.9 Hz, 1H), 8.71-8.62 (m, 1H), 7.98 (dd, J = 8.1, 4.7 Hz, 2H), 7.87 (s, 1H), 7.73 (t, J = 8.0 Hz, 1H), 7.54 (d, J = 8.2 Hz, 2H), 7.45-7.34 (m, 4H), 7.29 (s, 1H), 7.21 (s, 1H), 5.12 (s, 2H), 3.44 (s, 3H). | $^{13}$C NMR (125 MHz, CDCl$_3$) δ 163.8, 157.5, 153.1, 150.9, 150.3, 137.1, 136.8, 135.7, 135.7, 134.2, 132.7, 130.6, 129.1, 128.9, 125.1, 125.0, 123.3, 122.0, 118.3, 115.1, 56.3, 40.0, | ESI-MS m/z: 393 (M + H)$^+$ |
| 32 | 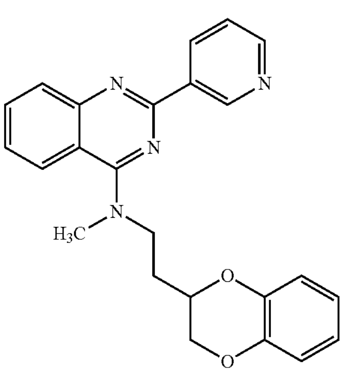 [SMILES: CN(CCC1COc2ccccc2O1)c1nc(-c2cccnc2)nc2ccccc12] | 398 | 3.16 (act) | $^1$H NMR (500 MHz, CDCl$_3$) δ 9.73 (d, J = 1.4 Hz, 1H), 8.79 (dt, J = 7.9, 1.8 Hz, 1H), 8.68 (dd, J = 4.7, 1.5 Hz, 1H), 8.06 (d, J = 8.2 Hz, 1H), 7.94 (d, J = 8.3 Hz, 1H), 7.77-7.69 (m, 1H), 7.44-7.34 (m, 2H), 6.93-6.77 (m, 4H), 4.36-4.18 (m, 3H), 4.08-3.93 (m, 2H), 3.52 (s, 3H), 2.34-2.22 (m, 1H), 2.22-2.10 (m, 1H). | $^{13}$C NMR (125 MHz, CDCl$_3$) δ 163.2, 157.4, 153.1, 150.8, 150.2, 143.3, 143.1, 135.7, 134.3, 132.4, 129.0, 125.5, 124.8, 123.3, 121.7, 121.6, 117.4, 117.3, 115.3, 71.1, 68.0, 49.3, 41.1, 28.7, | ESI-MS m/z: 399 (M + H)$^+$ |

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 33 | 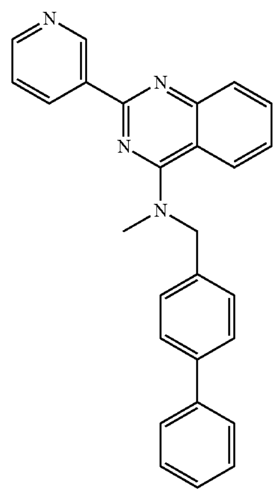 [SMILES: CN(Cc1ccc(-c2ccccc2)cc1)c1nc(-c2cccnc2)nc2ccccc12] | 402 | NA | $^1$H NMR (500 MHz, CDCl$_3$) δ 9.76 (s, 1H), 8.80 (d, J = 7.9 Hz, 1H), 8.69 (d, J = 3.5 Hz, 1H), 7.99 (dd, J = 11.9, 8.7 Hz, 2H), 7.73 (t, J = 7.5 Hz, 1H), 7.68-7.55 (m, 5H), 7.50 (d, J = 8.0 Hz, 2H), 7.45 (t, J = 7.6 Hz, 2H), 7.42-7.32 (m, 3H), 5.12 (s, 2H), 3.43 (s, 3H). | $^{13}$C NMR (125 MHz, CDCl$_3$) δ 164.0, 157.6, 153.0, 150.8, 150.4, 140.7, 140.6, 136.5, 135.7, 134.3, 132.5, 129.0, 128.9, 127.8, 127.7, 127.5, 127.1, 125.2, 125.0, 123.2, 115.1, 56.8, 39.7, | |
| 34 | 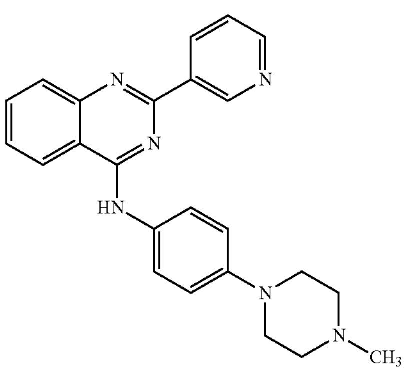 [SMILES: CN1CCN(c2ccc(Nc3nc(-c4cccnc4)nc4ccccc34)cc2)CC1] | 396 | NA | $^1$H NMR (500 MHz, CDCl$_3$) δ 9.71 (d, J = 1.5 Hz, 1H), 8.77 (dt, J = 7.9, 1.8 Hz, 1H), 8.67 (dd, J = 4.7, 1.5 Hz, 1H), 7.97 (d, J = 8.2 Hz, 1H), 7.88 (d, J = 8.2 Hz, 1H), 7.80 (t, J = 7.5 Hz, 1H), 7.71 (d, J = 8.8 Hz, 2H), 7.52 (t, J = 7.5 Hz, 1H), 7.49 (s, 1H), 7.40 (dd, J = 7.8, 4.8 Hz, 1H), 7.03 (d, J = 8.9 Hz, 2H), 3.32-3.15 (m, 4H), 2.68-2.53 (m, 4H), 2.37 (s, 3H). | $^{13}$C NMR (125 MHz, CDCl$_3$) δ 158.7, 157.7, 150.9, 150.4, 148.5, 135.8, 134.3, 133.0, 130.5, 129.3, 126.4, 123.3, 123.1, 120.4, 116.5, 114.1, 55.2, 49.5, 46.3, | ESI-MS m/z: 397 (M + H)$^+$ |
| 35 | 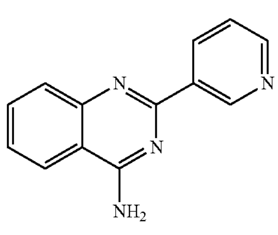 [SMILES: Nc1nc(-c2cccnc2)nc2ccccc12] | 222 | Weak (act) | $^1$H NMR (500 MHz, d6-DMSO) δ 9.59 (d, J = 1.5 Hz, 1H), 8.71 (dt, J = 7.9, 1.8 Hz, 1H), 8.68 (dd, J = 4.7, 1.5 Hz, 1H), 8.29 (d, J = 8.2 Hz, 1H), 7.98 (brs, 2H), 7.83-7.73 (m, 2H), 7.57-7.45 (m, 2H). | $^{13}$C NMR (125 MHz, CDCl$_3$) δ 162.6, 158.6, 151.0, 150.6, 149.6, 135.4, 134.3, 133.6, 128.1, 126.0, 124.1, 123.8, 113.9, | ESI-MS m/z: 223 (M + H)$^+$ |

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 36 | 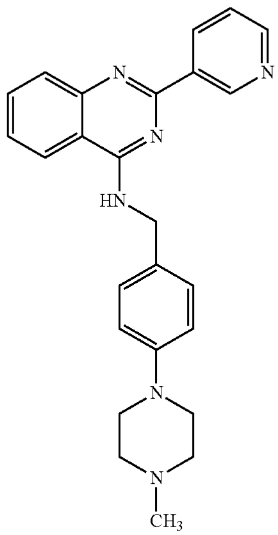 [SMILES: CN1CCN(c2ccc(CNc3nc(-c4cccnc4)nc4ccccc34)cc2)CC1] | 410 | 39.81 (act) | $^1$H NMR (500 MHz, CDCl$_3$) δ 9.77 (d, J = 1.5 Hz, 1H), 8.82 (dt, J = 7.9, 1.8 Hz, 1H), 8.68 (dd, J = 4.8, 1.5 Hz, 1H), 7.92 (d, J = 8.3 Hz, 1H), 7.78-7.71 (m, 1H), 7.69 (d, J = 8.1 Hz, 1H), 7.47-7.38 (m, 2H), 7.35 (d, J = 8.6 Hz, 2H), 6.92 (d, J = 8.6 Hz, 2H), 6.03 (s, 1H), 4.89 (d, J = 5.2 Hz, 2H), 3.27-3.11 (m, 4H), 2.64-2.47 (m, 4H), 2.34 (s, 3H). | $^{13}$C NMR (125 MHz, CDCl$_3$) δ 159.5, 158.8, 151.0, 150.8, 150.5, 150.4, 135.8, 134.5, 132.8, 129.3, 129.1, 129.0, 125.9, 123.2, 120.7, 116.2, 113.9, 55.1, 49.1, 46.2, 45.1, | ESI-MS m/z: 411 (M + H)$^+$ |
| 37 | 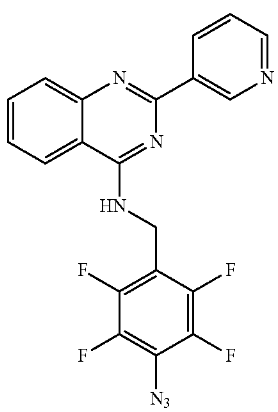 [SMILES: [N-]=[N+]=Nc1c(F)c(F)c(CNc2nc(-c3cccnc3)nc3ccccc23)c(F)c1F] | 425 | Weak (act) | $^1$H NMR (500 MHz, CDCl$_3$) δ 9.76 (d, J = 1.6 Hz, 1H), 8.82 (dt, J = 7.9, 1.9 Hz, 1H), 8.71 (dd, J = 4.8, 1.7 Hz, 1H), 7.95 (d, J = 8.3 Hz, 1H), 7.82-7.76 (m, 1H), 7.74 (d, J = 8.2 Hz, 1H), 7.54-7.46 (m, 1H), 7.43 (dd, J = 7.9, 4.8 Hz, 1H), 6.23 (t, J = 5.8 Hz, 1H), 5.13 (d, J = 6.0 Hz, 2H). | $^{13}$C NMR (125 MHz, CDCl$_3$) δ 159.1, 158.6, 151.0, 150.5, 150.3, 135.7, 134.2, 133.2, 129.2, 126.4, 123.3, 120.5, 113.8, 33.4, | ESI-MS m/z: 426 (M + H)$^+$ |
| 38 | 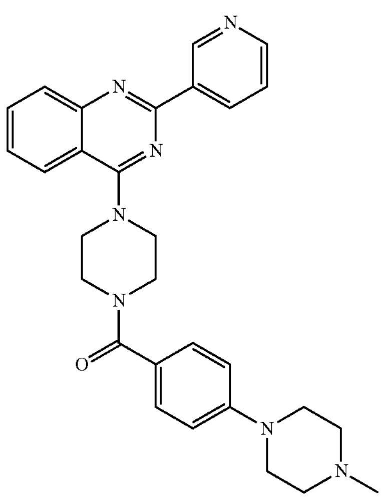 [SMILES: CN1CCN(c2ccc(C(=O)N3CCN(c4nc(-c5cccnc5)nc5ccccc45)CC3)cc2)CC1] | 493 | Weak (act) | $^1$H NMR (500 MHz, CDCl$_3$) δ 9.70 (d, J = 1.6 Hz, 1H), 8.77 (dt, J = 7.9, 1.8 Hz, 1H), 8.68 (dd, J = 4.7, 1.6 Hz, 1H), 7.99 (d, J = 8.3 Hz, 1H), 7.91 (d, J = 8.1 Hz, 1H), 7.81-7.72 (m, 1H), 7.51-7.44 (m, 1H), 7.44-7.35 (m, 3H), 6.91 (d, J = 8.8 Hz, 2H), 3.89 (s, 8H), 3.35-3.22 (m, 4H), 2.61-2.51 (m, 4H), 2.35 (s, 3H). | $^{13}$C NMR (125 MHz, CDCl$_3$) δ 171.1, 165.0, 157.6, 152.7, 152.5, 151.0, 150.2, 135.7, 133.9, 133.0, 129.3, 129.2, 125.8, 125.0, 124.7, 123.3, 115.6, 114.7, 54.9, 50.0, 48.2, 46.2, 46.0, | ESI-MS m/z: 494 (M + H)$^+$ |

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 39 | (cyclopentyl-NH-quinazoline-2-(3-pyridyl)) | 290 | 0.79 (inh) | $^1$H NMR (500 MHz, CDCl$_3$) δ 9.76 (d, J = 1.5 Hz, 1H), 8.81 (dt, J = 7.9, 1.9 Hz, 1H), 8.68 (dd, J = 4.8, 1.7 Hz, 1H), 7.91 (d, J = 8.2 Hz, 1H), 7.76-7.71 (m, 1H), 7.70 (d, J = 8.2 Hz, 1H), 7.46-7.42 (m, 1H), 7.40 (dd, J = 7.9, 4.8 Hz, 1H), 5.73 (d, J = 6.1 Hz, 1H), 4.80-4.72 (m, 1H), 2.34-2.25 (m, 2H), 1.86-1.71 (m, 4H), 1.67-1.59 (m, 2H). | $^{13}$C NMR (125 MHz, CDCl$_3$) δ 159.4, 158.8, 150.7, 150.4, 150.3, 135.7, 134.6, 132.7, 129.0, 125.8, 123.2, 120.6, 113.9, 53.2, 33.4, 24.1, | ESI-MS m/z: 291 (M + H)$^+$ |
| 40 | (cyclohexyl-NH-quinazoline-2-(3-pyridyl)) | 304 | 0.177 (inh) | $^1$H NMR (500 MHz, CDCl$_3$) δ 9.74 (s, 1H), 8.84 (d, J = 6.6 Hz, 1H), 8.70 (s, 1H), 7.95 (d, J = 7.1 Hz, 1H), 7.74 (t, J = 7.7 Hz, 2H), 7.49-7.35 (m, 2H), 5.77 (s, 1H), 4.48-4.32 (m, 1H), 2.28-2.20 (m, 2H), 1.93-1.79 (m, 2H), 1.79-1.67 (m, 1H), 1.61-1.46 (m, 2H), 1.46-1.23 (m, 3H). | $^{13}$C NMR (125 MHz, CDCl$_3$) δ 158.9, 158.8, 150.7, 150.5, 150.3, 135.7, 134.6, 132.7, 129.0, 125.8, 123.2, 120.5, 113.9, 50.1, 33.0, 25.9, 25.1, | ESI-MS m/z: 305 (M + H)$^+$ |
| 41 | (1-isopropylpiperidin-4-yl-NH-quinazoline-2-(3-pyridyl)) | 347 | 35.48 (inh) | $^1$H NMR (500 MHz, CDCl$_3$) δ 9.73 (d, J = 1.2 Hz, 1H), 8.79 (dt, J = 7.8, 1.5 Hz, 1H), 8.68 (dd, J = 4.6, 1.2 Hz, 1H), 7.91 (d, J = 8.3 Hz, 1H), 7.77-7.73 (m, 1H), 7.71 (d, J = 8.2 Hz, 1H), 7.49-7.43 (m, 1H), 7.41 (dd, J = 7.8, 4.8 Hz, 1H), 5.68 (d, J = 7.1 Hz, 1H), 4.49-4.35 (m, 1H), 2.99 (d, J = 11.1 Hz, 2H), 2.90-2.79 (m, 1H), 2.47 (t, J = 11.6 Hz, 2H), 2.28 (d, J = 11.5 Hz, 2H), 1.80-1.66 (m, 2H), 1.13 (d, J = 6.4 Hz, 6H). | $^{13}$C NMR (125 MHz, CDCl$_3$) δ 159.0, 158.7, 150.8, 150.5, 150.4, 135.7, 134.5, 132.8, 129.0, 125.9, 123.3, 120.6, 113.9, 54.9, 48.7, 47.8, 32.3, 18.4, | ESI-MS m/z: 348 (M + H)$^+$ |
| 42 | (cyclopropyl-NH-quinazoline-2-(3-pyridyl)) | 262 | 39.81 (inh) | $^1$H NMR (500 MHz, CDCl$_3$) δ 9.81 (s, 1H), 8.89 (d, J = 7.9 Hz, 1H), 8.70 (d, J = 3.7 Hz, 1H), 7.96 (d, J = 8.3 Hz, 1H), 7.77-7.73 (m, 1H), 7.71 (d, J = 8.2 Hz, 1H), 7.47-7.36 (m, 2H), 6.14 (s, 1H), 3.17 (td, J = 6.9, 3.1 Hz, 1H), 1.07-0.95 (m, 2H), 0.79-0.67 (m, 2H). | $^{13}$C NMR (125 MHz, CDCl$_3$) δ 160.9, 158.9, 150.8, 150.5, 150.4, 135.8, 134.5, 132.8, 129.0, 126.0, 123.2, 120.6, 113.9, 24.5, 7.5, | ESI-MS m/z: 263 (M + H)$^+$ |
| 43 | (cyclobutyl-NH-quinazoline-2-(3-pyridyl)) | 276 | 4.47 (inh) | $^1$H NMR (500 MHz, CDCl$_3$) δ 9.75 (s, 1H), 8.87-8.79 (m, 1H), 8.69 (d, J = 4.2 Hz, 1H), 7.93 (dd, J = 8.0, 4.1 Hz, 1H), 7.74 (t, J = 8.2 Hz, 2H), 7.47-7.43 (m, 1H), 7.43-7.39 (m, 1H), 6.03 (s, 1H), 4.96-4.97 (m, 1H), 2.66-2.54 (m, 2H), 2.16-2.03 (m, 2H), 1.96-1.85 (m, 2H). | $^{13}$C NMR (125 MHz, CDCl$_3$) δ 158.8, 150.7, 150.5, 150.4, 135.7, 134.5, 132.8, 129.0, 125.9, 123.2, 120.6, 113.7, 46.8, 31.4, 15.6, | ESI-MS m/z: 277 (M + H)$^+$ |

-continued

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 44 | 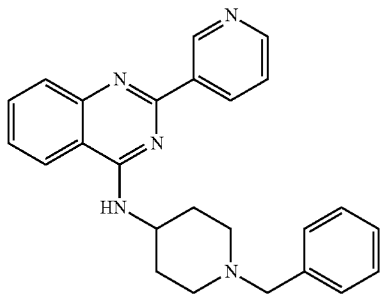 [SMILES: c1ccc(CN2CCC(Nc3nc(-c4cccnc4)nc4ccccc34)CC2)cc1] | 395 | 31.62 (inh) | $^1$H NMR (500 MHz, CDCl$_3$) δ 9.72 (d, J = 1.6 Hz, 1H), 8.78 (dt, J = 7.9, 1.9 Hz, 1H), 8.69 (dd, J = 4.8, 1.6 Hz, 1H), 7.91 (d, J = 8.2 Hz, 1H), 7.77-7.72 (m, 1H), 7.71 (d, J = 8.1 Hz, 1H), 7.50-7.43 (m, 1H), 7.41 (dd, J = 7.8, 5.0 Hz, 1H), 7.39-7.27 (m, 5H), 5.66 (d, J = 7.1 Hz, 1H), 4.49-4.37 (m, 1H), 3.62 (s, 2H), 2.98 (d, J = 10.6 Hz, 2H), 2.38-2.29 (m, 2H), 2.24 (d, J = 11.4 Hz, 2H), 1.81-1.69 (m, 2H). | $^{13}$C NMR (125 MHz, CDCl$_3$) δ 159.0, 158.7, 150.8, 150.5, 150.3, 135.6, 134.5, 132.8, 129.4, 129.0, 128.4, 127.4, 125.9, 123.2, 120.6, 113.9, 63.2, 52.5, 48.4, 32.0, | ESI-MS m/z: 396 (M + H)$^+$ |
| 45 | 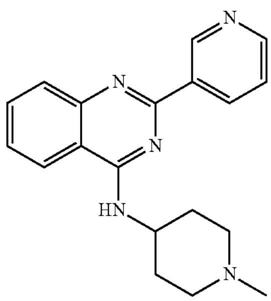 [SMILES: CN1CCC(Nc2nc(-c3cccnc3)nc3ccccc23)CC1] | 319 | Weak (inh) | $^1$H NMR (500 MHz, CDCl$_3$) δ 9.72 (s, 1H), 8.78 (d, J = 7.5 Hz, 1H), 8.68 (d, J = 3.4 Hz, 1H), 7.90 (d, J = 8.1 Hz, 1H), 7.73 (t, J = 7.4 Hz, 1H), 7.49-7.34 (m, 3H), 5.73 (d, J = 6.1 Hz, 1H), 4.48-4.30 (m, 1H), 2.91 (d, J = 9.1 Hz, 2H), 2.36 (s, 3H), 2.32-2.17 (m, 4H), 1.72 (m, 2H). | $^{13}$C NMR (125 MHz, CDCl$_3$) δ 159.0, 158.7, 150.8, 150.4, 150.3, 135.6, 134.5, 132.8, 129.0, 125.9, 123.2, 120.7, 113.9, 54.7, 48.0, 46.3, 32.1, | ESI-MS m/z: 320 (M + H)$^+$ |
| 46 | 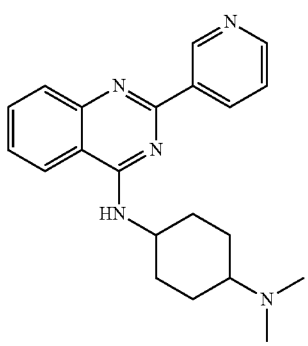 [SMILES: CN(C)C1CCC(Nc2nc(-c3cccnc3)nc3ccccc23)CC1] | 347 | NA | $^1$H NMR (500 MHz, CDCl$_3$) δ 9.70 (s, 1H), 8.76 (d, J = 7.8 Hz, 1H), 8.65 (d, J = 3.6 Hz, 1H), 7.87 (d, J = 8.2 Hz, 1H), 7.78 (d, J = 8.1 Hz, 1H), 7.75-7.66 (m, 1H), 7.42 (t, J = 7.5 Hz, 1H), 7.37 (dd, J = 7.5, 4.9 Hz, 1H), 6.02 (d, J = 6.7 Hz, 1H), 4.64 (s, 1H), 2.38 (s, 6H), 2.30 (s, 1H), 2.05 (s, 2H), 1.83 (s, 6H). | $^{13}$C NMR (125 MHz, CDCl$_3$) δ 159.0, 158.6, 150.6, 150.3, 150.2, 135.7, 134.6, 132.7, 128.8, 125.9, 123.2, 120.8, 114.0, 62.2, 46.0, 42.5, 27.9, 25.6, | ESI-MS m/z: 348 (M + H)$^+$ |
| 47 | 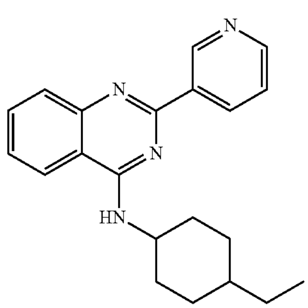 [SMILES: CCC1CCC(Nc2nc(-c3cccnc3)nc3ccccc23)CC1] | 332 | 0.126 (inh) | 3:2 isomers mixture | | ESI-MS m/z: 333 (M + H)$^+$ |

-continued

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 48 | 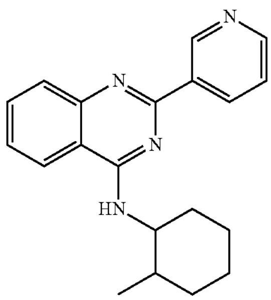 [SMILES: CC1CCCCC1Nc1nc(-c2cccnc2)nc2ccccc12] | 318 | 0.089 (inh) | 2:1 isomer mixture | | ESI-MS m/z: 319 (M + H)$^+$ |
| 49 | 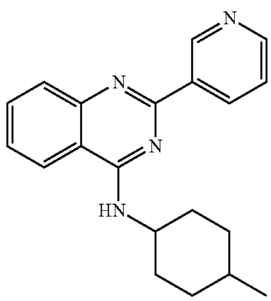 [SMILES: CC1CCC(Nc2nc(-c3cccnc3)nc3ccccc23)CC1] | 318 | 0.056 (inh) | Cis:Trans = 3:2 isomer mixture | | ESI-MS m/z: 319 (M + H)$^+$ |
| 50 | 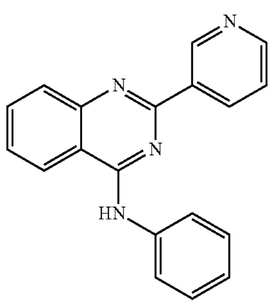 [SMILES: c1ccc(Nc2nc(-c3cccnc3)nc3ccccc23)cc1] | 298 | Weak (act) | $^1$H NMR (500 MHz, CDCl$_3$) δ 9.73 (d, J = 1.8 Hz, 1H), 8.82 (dt, J = 7.9, 1.9 Hz, 1H), 8.70 (dd, J = 4.8, 1.6 Hz, 1H), 8.01 (d, J = 8.3 Hz, 1H), 7.95 (d, J = 8.1 Hz, 1H), 7.86 (d, J = 7.6 Hz, 2H), 7.84-7.80 (m, 1H), 7.69 (brs, 1H), 7.61-7.52 (m, 1H), 7.50-7.45 (m, 2H), 7.43 (dd, J = 7.9, 4.8 Hz, 1H), 7.21 (t, J = 7.4 Hz, 1H). | $^{13}$C NMR (125 MHz, CDCl$_3$) δ 158.4, 157.6, 150.8, 150.7, 150.2, 138.4, 136.1, 134.2, 133.3, 129.3, 129.2, 126.8, 124.6, 123.4, 121.6, 120.5, 114.1 | ESI-MS m/z: 299 (M + H)$^+$ |
| 51 | 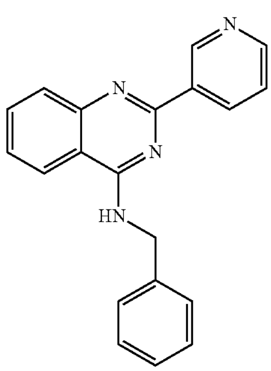 [SMILES: c1ccc(CNc2nc(-c3cccnc3)nc3ccccc23)cc1] | 312 | 7.08 (inh) | $^1$H NMR (500 MHz, CDCl$_3$) δ 9.56 (s, 1H), 8.61 (d, J = 7.9 Hz, 1H), 8.47 (d, J = 3.6 Hz, 1H), 7.74 (d, J = 8.3 Hz, 1H), 7.61 (d, J = 8.2 Hz, 1H), 7.58-7.44 (m, 1H), 7.28-7.18 (m, 4H), 7.18-7.13 (m, 2H), 7.13-7.07 (m, 1H), 6.39 (s, 1H), 4.78 (d, J = 5.4 Hz, 2H). | $^{13}$C NMR (125 MHz, CDCl$_3$) δ 159.6, 158.7, 150.6, 150.4, 150.2, 138.5, 135.8, 134.5, 132.8, 128.8, 128.0, 127.7, 126.0, 123.2, 120.9, 113.9, 45.4, | ESI-MS m/z: 313 (M + H)$^+$ |

-continued

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 52 | 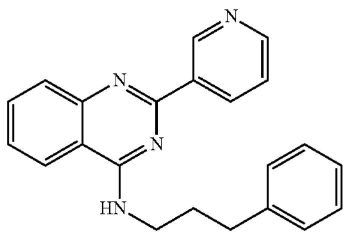 [SMILES: c1ccc(CCCNc2nc(-c3cccnc3)nc3ccccc23)cc1] | 340 | 1.78 (inh) | $^1$H NMR (500 MHz, CDCl$_3$) δ 9.74 (s, 1H), 8.76 (dt, J = 7.9, 1.8 Hz, 1H), 8.68 (d, J = 3.6 Hz, 1H), 7.90 (d, J = 8.3 Hz, 1H), 7.78-7.66 (m, 1H), 7.53 (d, J = 7.8 Hz, 1H), 7.45-7.34 (m, 2H), 7.33-7.27 (m, 2H), 7.25-7.19 (m, 3H), 5.94 (s, 1H), 3.89-3.75 (m, 2H), 2.81 (t, J = 7.4 Hz, 2H), 2.13 (p, J = 7.2 Hz, 2H). | $^{13}$C NMR (125 MHz, CDCl$_3$) δ 159.7, 158.7, 150.7, 150.3, 150.2, 141.6, 135.8, 134.5, 132.7, 128.8, 128.7, 128.5, 126.2, 125.8, 123.2, 120.6, 113.9, 41.2, 33.7, 30.7, | ESI-MS m/z: 341 (M + H)$^+$ |
| 53 | 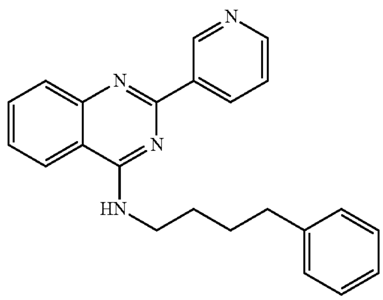 [SMILES: c1ccc(CCCCNc2nc(-c3cccnc3)nc3ccccc23)cc1] | 354 | 1.58 (inh) | $^1$H NMR (500 MHz, CDCl$_3$) δ 9.75 (s, 1H), 8.81 (d, J = 7.9 Hz, 1H), 8.69 (d, J = 3.7 Hz, 1H), 7.93 (d, J = 8.3 Hz, 1H), 7.77-7.71 (m, 1H), 7.70 (d, J = 8.1 Hz, 1H), 7.51-7.35 (m, 2H), 7.28 (d, J = 7.7 Hz, 2H), 7.23-7.10 (m, 3H), 5.90 (s, 1H), 3.89-3.70 (m, 2H), 2.72 (t, J = 6.7 Hz, 2H), 1.90-1.75 (m, 4H). | $^{13}$C NMR (125 MHz, CDCl$_3$) δ 159.7, 158.7, 150.8, 150.3, 150.1, 142.1, 135.8, 134.4, 132.8, 128.8, 128.5, 128.5, 126.0, 125.9, 123.3, 120.6, 113.9, 41.4, 35.7, 29.0, 28.9, | ESI-MS m/z: 355 (M + H)$^+$ |
| 54 | 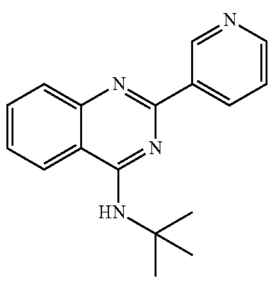 [SMILES: CC(C)(C)Nc1nc(-c2cccnc2)nc2ccccc12] | 278 | Weak (act) | $^1$H NMR (500 MHz, CDCl$_3$) δ 9.74 (s, 1H), 8.82 (d, J = 7.7 Hz, 1H), 8.69 (d, J = 2.9 Hz, 1H), 7.92 (d, J = 8.1 Hz, 1H), 7.73 (t, J = 7.4 Hz, 1H), 7.67 (d, J = 8.2 Hz, 1H), 7.48-7.40 (m, 2H), 5.70 (s, 1H), 1.69 (s, 9H). | $^{13}$C NMR (125 MHz, CDCl$_3$) δ 159.1, 158.2, 150.7, 150.3, 150.0, 135.8, 134.6, 132.6, 129.0, 125.9, 123.3, 120.5, 114.3, 52.9, 29.0, | ESI-MS m/z: 279 (M + H)$^+$ |
| 55 | 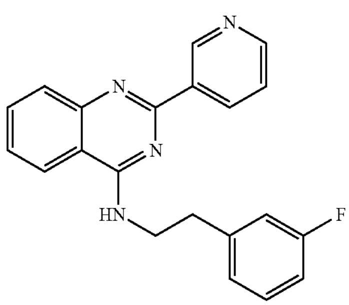 [SMILES: Fc1cccc(CCNc2nc(-c3cccnc3)nc3ccccc23)c1] | 344 | 0.141 (inh) | $^1$H NMR (500 MHz, CDCl$_3$) δ 9.76 (s, 1H), 8.88 (d, J = 8.0 Hz, 1H), 8.71 (d, J = 3.8 Hz, 1H), 8.00 (d, J = 8.3 Hz, 1H), 7.78-7.72 (m, 1H), 7.71 (d, J = 8.1 Hz, 1H), 7.48-7.40 (m, 2H), 7.33-7.26 (m, 1H), 7.06 (d, J = 7.5 Hz, 1H), 6.99 (d, J = 9.7 Hz, 1H), 6.97-6.92 (m, 1H), 6.35 (brs, 1H), 4.07 (d, J = 6.0 Hz, 2H), 3.12 (t, J = 7.0 Hz, 2H). | $^{13}$C NMR (125 MHz, CDCl$_3$) δ 164.1, 162.2, 159.7, 158.3, 150.9, 150.1, 149.2, 141.6, 141.5, 136.1, 133.8, 133.2, 130.4, 130.3, 128.2, 126.3, 124.6, 123.4, 120.9, 115.9, 115.7, 113.8, 113.8, 113.6, 42.5, 35.2, | ESI-MS m/z: 345 (M + H)$^+$ |
| 56 | 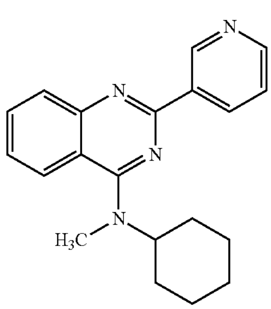 [SMILES: CN(c1nc(-c2cccnc2)nc2ccccc12)C1CCCCC1] | 318 | 5.01 (act) | $^1$H NMR (500 MHz, CDCl$_3$) δ 9.72 (s, 1H), 8.79 (d, J = 7.8 Hz, 1H), 8.67 (d, J = 3.8 Hz, 1H), 7.94 (d, J = 8.3 Hz, 2H), 7.70 (t, J = 7.6 Hz, 1H), 7.47-7.29 (m, 2H), 4.52 (t, J = 11.8 Hz, 1H), 3.28 (s, 3H), 2.01 (d, J = 11.5 Hz, 2H), 1.92 (d, J = 13.2 Hz, 2H), 1.81-1.58 (m, 3H), 1.58-1.34 (m, 2H), 1.29-1.10 (m, 1H). | $^{13}$C NMR (125 MHz, CDCl$_3$) δ 163.8, 157.3, 153.0, 150.7, 150.3, 135.7, 134.4, 132.2, 128.7, 125.5, 124.4, 123.2, 115.4, 59.9, 34.3, 30.1, 26.0, 25.8, | ESI-MS m/z: 319 (M + H)$^+$ |

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 57 | 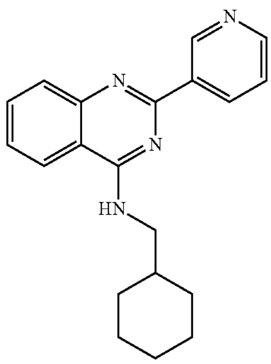 [SMILES: c1cncc(-c2nc(NCC3CCCCC3)c3ccccc3n2)c1] | 318 | 0.354 (inh) | $^1$H NMR (500 MHz, CDCl$_3$) δ 9.75 (s, 1H), 8.81 (d, J = 7.8 Hz, 1H), 8.68 (d, J = 3.8 Hz, 1H), 7.91 (d, J = 8.2 Hz, 1H), 7.79-7.65 (m, 2H), 7.50-7.34 (m, 2H), 5.98 (s, 1H), 3.65 (t, J = 6.1 Hz, 2H), 1.87 (d, J = 12.6 Hz, 2H), 1.82-1.61 (m, 4H), 1.32-1.18 (m, 3H), 1.14-1.04 (m, 1H). | $^{13}$C NMR (125 MHz, CDCl$_3$) δ 159.9, 158.8, 150.7, 150.3, 135.7, 134.6, 132.7, 128.9, 125.8, 123.2, 120.5, 114.0, 47.6, 38.0, 31.3, 26.5, 26.0, | ESI-MS m/z: 319 (M + H)$^+$ |
| 58 | 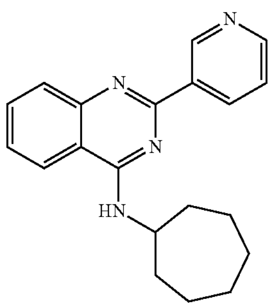 [SMILES: c1cncc(-c2nc(NC3CCCCCC3)c3ccccc3n2)c1] | 318 | 0.063 (inh) | $^1$H NMR (500 MHz, CDCl$_3$) δ 9.75 (s, 1H), 8.82 (d, J = 7.9 Hz, 1H), 8.68 (s, 1H), 7.93 (d, J = 8.3 Hz, 1H), 7.78-7.65 (m, 2H), 7.50-7.37 (m, 2H), 5.76 (d, J = 5.6 Hz, 1H), 4.64-4.46 (m, 1H), 2.25-2.12 (m, 2H), 1.83-1.52 (m, 10H). | $^{13}$C NMR (125 MHz, CDCl$_3$) δ 158.7, 158.6, 150.7, 150.3, 150.2, 135.8, 134.5, 132.7, 128.8, 125.9, 123.3, 120.6, 113.9, 52.3, 34.9, 28.3, 24.6, | ESI-MS m/z: 319 (M + H)$^+$ |
| 59 | 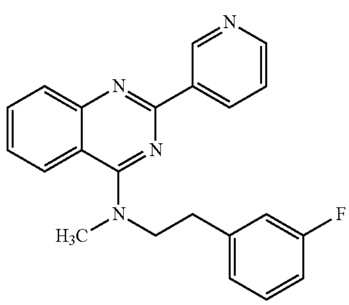 [SMILES: CN(CCc1cccc(F)c1)c1nc(-c2cccnc2)nc2ccccc12] | 358 | 4.47 (act) | $^1$H NMR (500 MHz, CDCl$_3$) δ 9.73 (s, 1H), 8.90 (brs, 1H), 8.72 (d, J = 4.0 Hz, 1H), 8.06 (brs, 1H), 7.99 (d, J = 8.4 Hz, 1H), 7.75 (t, J = 7.5 Hz, 1H), 7.46 (dd, J = 7.8, 4.9 Hz, 1H), 7.44-7.39 (m, 1H), 7.30-7.27 (m, 1H), 7.05 (d, J = 7.6 Hz, 1H), 6.98 (d, J = 9.7 Hz, 1H), 6.93 (td, J = 8.5, 2.3 Hz, 1H), 4.19-4.04 (m, 2H), 3.46 (s, 3H), 3.23-3.10 (m, 2H). | $^{13}$C NMR (125 MHz, CDCl$_3$) δ 164.1, 163.1, 162.1, 150.7, 150.0, 136.3, 132.8, 130.3, 130.3, 125.4, 125.0, 124.6, 123.5, 115.9, 115.7, 113.7, 113.6, 54.8, 41.2, 33.4, | ESI-MS m/z: 359 (M + H)$^+$ |
| 60 | 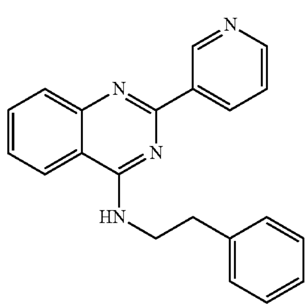 [SMILES: c1ccc(CCNc2nc(-c3cccnc3)nc3ccccc23)cc1] | 326 | 0.112 (inh) | $^1$H NMR (500 MHz, CDCl$_3$) δ 9.79 (s, 1H), 8.85 (d, J = 7.1 Hz, 1H), 8.70 (s, 1H), 7.94 (d, J = 8.4 Hz, 1H), 7.78-7.69 (m, 1H), 7.60 (d, J = 8.0 Hz, 1H), 7.46-7.39 (m, 2H), 7.38-7.31 (m, 2H), 7.30-7.25 (m, 3H), 5.98 (s, 1H), 4.11-3.99 (m, 2H), 3.11 (t, J = 6.9 Hz, 2H). | $^{13}$C NMR (125 MHz, CDCl$_3$) δ 159.6, 158.7, 150.8, 150.3, 150.2, 139.0, 135.8, 134.4, 132.9, 129.0, 128.9, 126.8, 126.0, 123.3, 120.5, 113.9, 42.6, 35.4, | ESI-MS m/z: 327 (M + H)$^+$ |

-continued

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 61 | 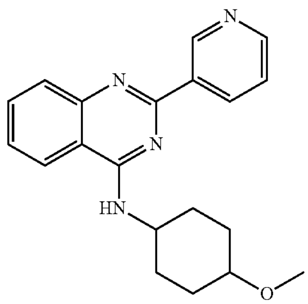 [SMILES: COC1CCC(Nc2nc(-c3cccnc3)nc3ccccc23)CC1] | 334 | 0.251 (inh) | $^1$H NMR (500 MHz, CDCl$_3$) δ 9.73 (s, 1H), 8.81 (d, J = 7.7 Hz, 1H), 8.70 (d, J = 3.4 Hz, 1H), 7.95 (d, J = 8.2 Hz, 1H), 7.81-7.57 (m, 2H), 7.52-7.32 (m, 2H), 5.69 (d, J = 0.8 Hz, 1H), 4.52-4.27 (m, 1H), 3.40 (s, 3H), 3.31-3.13 (m, 1H), 2.35 (d, J = 12.5 Hz, 2H), 2.18 (d, J = 11.3 Hz, 2H), 1.61-1.22 (m, 4H). | $^{13}$C NMR (125 MHz, CDCl$_3$) δ 159.1, 158.7, 150.8, 150.3, 135.8, 134.3, 132.8, 128.9, 125.9, 123.3, 120.6, 113.8, 78.4, 56.0, 49.7, 30.6, 30.4, | ESI-MS m/z: 335 (M + H)$^+$ |
| 62 | 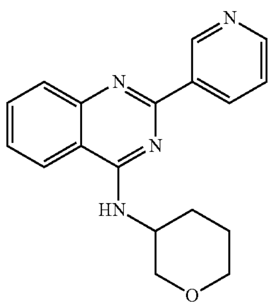 [SMILES: c1cncc(-c2nc(NC3CCCOC3)c3ccccc3n2)c1] | 306 | 0.891 (inh) | $^1$H NMR (500 MHz, CDCl$_3$) δ 9.72 (s, 1H), 8.80 (dt, J = 7.9, 1.9 Hz, 1H), 8.68 (d, J = 3.7 Hz, 1H), 7.93 (d, J = 8.3 Hz, 1H), 7.80 (d, J = 8.2 Hz, 1H), 7.78-7.73 (m, 1H), 7.50-7.44 (m, 1H), 7.41 (dd, J = 7.8, 4.8 Hz, 1H), 6.18 (d, J = 7.1 Hz, 1H), 4.68-4.59 (m, 1H), 4.01 (dd, J = 11.5, 2.7 Hz, 1H), 3.89-3.80 (m, 1H), 3.80-3.66 (m, 2H), 2.08-2.00 (m, 3H), 1.95-1.83 (m, 1H), 1.73-1.61 (m, 1H). | $^{13}$C NMR (125 MHz, CDCl$_3$) δ 159.0, 158.6, 150.7, 150.3, 150.2, 135.9, 134.4, 133.0, 128.9, 126.1, 123.3, 120.7, 113.9, 71.5, 68.6, 46.5, 27.8, 23.0, | ESI-MS m/z: 307 (M + H)$^+$ |
| 63 | 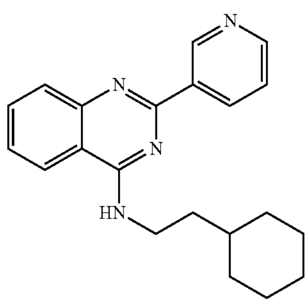 [SMILES: c1cncc(-c2nc(NCCC3CCCCC3)c3ccccc3n2)c1] | 332 | 0.282 (inh) | $^1$H NMR (500 MHz, CDCl$_3$) δ 9.76 (s, 1H), 8.86-8.78 (m, 1H), 8.69 (d, J = 4.1 Hz, 1H), 7.92 (dd, J = 7.9, 5.4 Hz, 1H), 7.79-7.67 (m, 2H), 7.48-7.37 (m, 2H), 5.84 (s, 1H), 3.86-3.75 (m, 2H), 1.83 (d, J = 12.3 Hz, 2H), 1.76-1.60 (m, 5H), 1.50-1.38 (m, 1H), 1.33-1.12 (m, 3H), 1.08-0.96 (m, 2H). | $^{13}$C NMR (125 MHz, CDCl$_3$) δ 159.7, 158.8, 150.7, 150.4, 150.3, 135.8, 135.7, 134.5, 132.8, 132.7, 128.9, 128.9, 125.9, 123.2, 120.6, 114.0, 39.4, 37.0, 35.7, 33.4, 26.6, 26.3, | ESI-MS m/z: 333 (M + H)$^+$ |
| 64 | 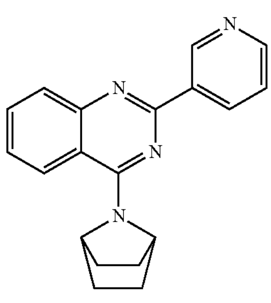 [SMILES: c1cncc(-c2nc(N3C4CCC3CC4)c3ccccc3n2)c1] | 302 | 2.24 (act) | $^1$H NMR (500 MHz, CDCl$_3$) δ 9.75 (s, 1H), 8.83 (d, J = 7.9 Hz, 1H), 8.69 (d, J = 3.6 Hz, 1H), 8.06 (d, J = 8.1 Hz, 1H), 7.96 (d, J = 8.3 Hz, 1H), 7.81-7.70 (m, 1H), 7.51-7.44 (m, 1H), 7.41 (dd, J = 7.9, 4.8 Hz, 1H), 4.90 (s, 2H), 2.07-1.92 (m, 4H), 1.59 (d, J = 7.1 Hz, 4H). | $^{13}$C NMR (125 MHz, CDCl$_3$) δ 162.5, 158.0, 151.7, 150.8, 150.3, 135.8, 134.2, 132.8, 128.6, 125.6, 125.0, 123.3, 116.5, 60.1, 29.3, | ESI-MS m/z: 303 (M + H)$^+$ |

-continued

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 65 | 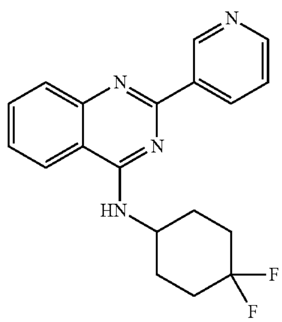 [SMILES: FC1(F)CCC(Nc2nc(-c3cccnc3)nc3ccccc23)CC1] | 340 | 0.316 (inh) | $^1$H NMR (500 MHz, CDCl$_3$) δ 9.72 (s, 1H), 8.80 (d, J = 7.8 Hz, 1H), 8.70 (d, J = 2.6 Hz, 1H), 7.95 (d, J = 8.3 Hz, 1H), 7.80-7.75 (m, 1H), 7.73 (d, J = 8.1 Hz, 1H), 7.47 (t, J = 7.5 Hz, 1H), 7.43 (dd, J = 7.7, 4.8 Hz, 1H), 5.70 (d, J = 6.2 Hz, 1H), 4.60-4.45 (m, 1H), 2.32 (d, J = 12.6 Hz, 2H), 2.28-2.12 (m, 2H), 2.12-1.93 (m, 2H), 1.85-1.70 (m, 2H). | $^{13}$C NMR (125 MHz, CDCl$_3$) δ 159.1, 158.5, 150.8, 150.3, 150.1, 135.8, 134.3, 133.1, 129.0, 126.2, 123.6 (q, J$_{C-F}$ = 241 Hz), 123.4, 120.5, 113.8, 48.1, 32.5 (t, J$_{C-F}$ = 24.7 Hz), 28.6 (d, J$_{C-F}$ = 9.2 Hz) | ESI-MS m/z: 341 (M + H)$^+$ |
| 66 | 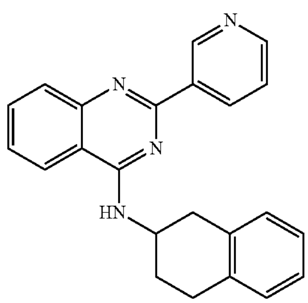 [SMILES: c1cncc(-c2nc(NC3CCc4ccccc4C3)c3ccccc3n2)c1] | 352 | 0.006 (inh) | $^1$H NMR (500 MHz, CDCl$_3$) δ 9.75 (s, 1H), 8.82 (d, J = 7.9 Hz, 1H), 8.68 (d, J = 3.7 Hz, 1H), 7.95 (d, J = 8.3 Hz, 1H), 7.75 (t, J = 7.7 Hz, 1H), 7.70 (d, J = 8.1 Hz, 1H), 7.47-7.42 (m, 1H), 7.41 (dd, J = 7.9, 4.8 Hz, 1H), 7.24-7.11 (m, 4H), 5.87 (d, J = 5.2 Hz, 1H), 5.00-4.87 (m, 1H), 3.43 (dd, J = 16.2, 5.0 Hz, 1H), 3.12-2.88 (m, 3H), 2.40-2.30 (m, 1H), 2.13-2.01 (m, 1H). | $^{13}$C NMR (125 MHz, CDCl$_3$) δ 159.2, 158.7, 150.8, 150.2, 135.8, 135.7, 134.3, 134.1, 132.9, 129.7, 129.1, 128.9, 126.4, 126.2, 126.0, 123.3, 120.7, 113.9, 47.1, 35.8, 28.5, 27.5, | ESI-MS m/z: 353 (M + H)$^+$ |
| 67 | 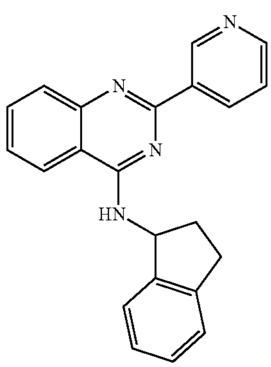 [SMILES: c1cncc(-c2nc(NC3CCc4ccccc43)c3ccccc3n2)c1] | 338 | 0.891 (inh) | $^1$H NMR (500 MHz, CDCl$_3$) δ 9.78 (d, J = 1.5 Hz, 1H), 8.84 (dt, J = 7.9, 1.9 Hz, 1H), 8.67 (dd, J = 4.8, 1.6 Hz, 1H), 7.95 (d, J = 8.4 Hz, 1H), 7.80-7.73 (m, 1H), 7.70 (d, J = 8.0 Hz, 1H), 7.50-7.37 (m, 3H), 7.35 (d, J = 7.5 Hz, 1H), 7.33-7.28 (m, 1H), 7.26-7.20 (m, 2H), 6.17 (q, J = 7.4 Hz, 1H), 6.02 (d, J = 7.5 Hz, 1H), 3.12 (ddd, J = 15.8, 8.7, 4.0 Hz, 1H), 3.04 (dt, J = 16.0, 8.0 Hz, 1H), 2.92-2.83 (m, 1H), 2.16-2.01 (m, 1H). | $^{13}$C NMR (125 MHz, CDCl$_3$) δ 159.5, 158.8, 150.8, 150.5, 150.3, 143.9, 143.4, 135.8, 134.5, 132.9, 129.0, 128.4, 127.0, 126.0, 125.2, 124.3, 123.3, 120.7, 113.8, 56.5, 34.1, 30.5, | ESI-MS m/z: 339 (M + H)$^+$ |
| 68 | 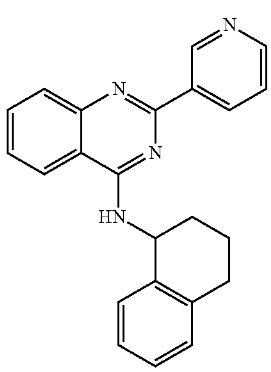 [SMILES: c1cncc(-c2nc(NC3CCCc4ccccc43)c3ccccc3n2)c1] | 352 | 1.12 (inh) | $^1$H NMR (500 MHz, CDCl$_3$) δ 9.78 (d, J = 0.9 Hz, 1H), 8.89 (d, J = 7.8 Hz, 1H), 8.69 (d, J = 3.5 Hz, 1H), 8.00 (d, J = 7.8 Hz, 1H), 7.83-7.73 (m, 1H), 7.68 (d, J = 8.0 Hz, 1H), 7.51-7.41 (m, 2H), 7.39 (d, J = 7.6 Hz, 1H), 7.25-7.22 (m, 1H), 7.22-7.15 (m, 2H), 6.02 (s, 1H), 5.94-5.86 (m, 1H), 3.00-2.80 (m, 2H), 2.34-2.23 (m, 1H), 2.20-2.12 (m, 1H), 2.00-1.93 (m, 2H). | $^{13}$C NMR (125 MHz, CDCl$_3$) δ 159.0, 158.7, 150.6, 150.2, 138.1, 136.8, 136.1, 133.0, 129.5, 129.1, 128.8, 127.7, 126.6, 126.1, 123.4, 120.7, 113.8, 49.2, 29.6, 29.5, 20.2, | ESI-MS m/z: 353 (M + H)$^+$ |

-continued

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 69 | 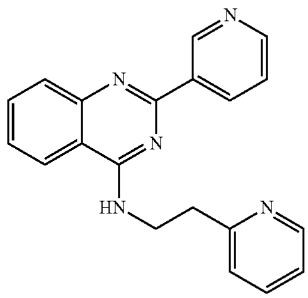 [SMILES: c1ccc(CCNc2nc(-c3cccnc3)nc3ccccc23)nc1] | 327 | 1.12 (inh) | $^1$H NMR (500 MHz, CDCl$_3$) δ 9.75 (d, J = 1.2 Hz, 1H), 8.82 (dt, J = 7.9, 1.9 Hz, 1H), 8.70-8.66 (m, 1H), 8.51 (s, 1H), 8.47 (d, J = 4.1 Hz, 1H), 7.93 (d, J = 8.2 Hz, 1H), 7.77-7.72 (m, 1H), 7.68 (d, J = 8.1 Hz, 1H), 7.59 (d, J = 7.8 Hz, 1H), 7.46-7.38 (m, 2H), 7.24 (dd, J = 7.7, 4.9 Hz, 1H), 6.28 (t, J = 5.3 Hz, 1H), 4.10-3.96 (m, 2H), 3.13 (t, J = 7.0 Hz, 2H). | $^{13}$C NMR (125 MHz, CDCl$_3$) δ 159.7, 158.6, 150.7, 150.2, 150.1, 148.1, 136.6, 135.8, 134.7, 134.4, 133.0, 128.9, 126.2, 123.8, 123.4, 120.7, 113.9, 42.4, 32.6, | ESI-MS m/z: 328 (M + H)$^+$ |
| 70 | 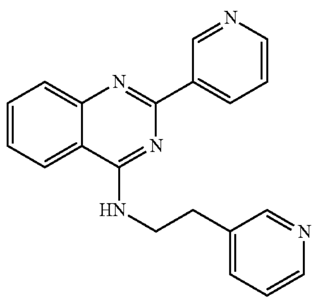 [SMILES: c1cncc(CCNc2nc(-c3cccnc3)nc3ccccc23)c1] | 327 | 5.01 (inh) | $^1$H NMR (500 MHz, CDCl$_3$) δ 9.77 (d, J = 1.4 Hz, 1H), 8.83 (dt, J = 7.9, 1.9 Hz, 1H), 8.68 (dd, J = 4.8, 1.7 Hz, 1H), 7.91 (d, J = 8.0 Hz, 1H), 7.73 (ddd, J = 8.3, 7.0, 1.3 Hz, 1H), 7.57 (d, J = 7.8 Hz, 1H), 7.46-7.37 (m, 2H), 7.07 (d, J = 8.3 Hz, 2H), 6.72-6.62 (m, 2H), 5.96-5.87 (m, 1H), 4.03-3.94 (m, 2H), 2.98 (t, J = 6.9 Hz, 2H). | $^{13}$C NMR (125 MHz, CDCl$_3$) δ 159.6, 158.8, 150.7, 150.3, 145.1, 135.8, 134.5, 132.8, 129.8, 128.9, 128.8, 125.9, 123.3, 120.6, 115.6, 114.0, 42.8, 34.5, | ESI-MS m/z: 328 (M + H)$^+$ |
| 71 | 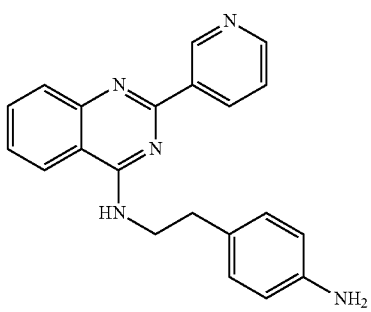 [SMILES: Nc1ccc(CCNc2nc(-c3cccnc3)nc3ccccc23)cc1] | 341 | 2.00 (act) | $^1$H NMR (500 MHz, CDCl$_3$) δ 9.74 (d, J = 1.5 Hz, 1H), 8.80 (dt, J = 7.9, 1.9 Hz, 1H), 8.66 (dd, J = 4.8, 1.7 Hz, 1H), 8.61 (d, J = 4.8 Hz, 1H), 7.88 (d, J = 8.3 Hz, 1H), 7.76 (d, J = 7.9 Hz, 1H), 7.73-7.67 (m, 1H), 7.63 (td, J = 7.7, 1.8 Hz, 1H), 7.47-7.41 (m, 1H), 7.38 (dd, J = 7.9, 4.8 Hz, 1H), 7.22 (d, J = 7.8 Hz, 1H), 7.18 (dd, J = 7.4, 5.0 Hz, 1H), 4.26-4.03 (m, 2H), 3.30-3.09 (m, 2H). | $^{13}$C NMR (125 MHz, CDCl$_3$) δ 160.2, 159.7, 158.8, 150.7, 150.3, 150.2, 149.2, 137.1, 135.8, 134.6, 132.7, 128.7, 125.9, 123.8, 123.2, 121.9, 121.1, 114.3, 40.7, 36.2, | ESI-MS m/z: 342 (M + H)$^+$ |
| 72 | 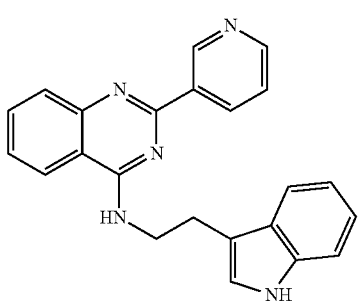 [SMILES: c1cncc(-c2nc(NCCc3c[nH]c4ccccc34)c3ccccc3n2)c1] | 365 | 1.28 (act) | $^1$H NMR (500 MHz, CDCl$_3$) δ 9.80 (d, J = 1.4 Hz, 1H), 8.83 (dt, J = 7.9, 1.9 Hz, 1H), 8.69 (dd, J = 4.7, 1.3 Hz, 1H), 8.26 (s, 1H), 7.91 (d, J = 8.3 Hz, 1H), 7.74-7.70 (m, 1H), 7.69 (d, J = 7.9 Hz, 1H), 7.50 (d, J = 8.1 Hz, 1H), 7.44-7.39 (m, 2H), 7.37 (t, J = 7.5 Hz, 1H), 7.24 (t, J = 7.6 Hz, 1H), 7.15 (t, J = 7.4 Hz, 1H), 7.10 (d, J = 1.8 Hz, 1H), 5.96 (s, 1H), 4.21-4.03 (m, 2H), 3.26 (t, J = 6.6 Hz, 2H). | $^{13}$C NMR (125 MHz, CDCl$_3$) δ 159.7, 158.9, 150.7, 150.4, 150.3, 136.6, 135.8, 134.6, 132.8, 128.9, 127.5, 125.9, 123.3, 122.5, 122.3, 120.6, 119.7, 118.8, 114.0, 113.2, 111.5, 41.7, 25.1 | ESI-MS m/z: 366 (M + H)$^+$ |

Table of Substituted Quinazoline Compounds

| No. | Structures | MW | IC$_{50}$ or AC$_{50}$ (μM) | 1H NMR | 13C NMR | Mass |
| --- | --- | --- | --- | --- | --- | --- |
| 73 | 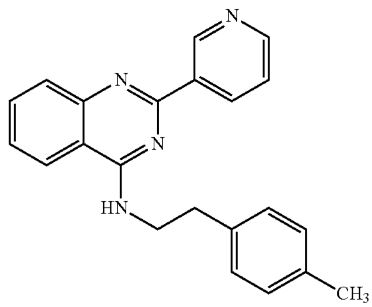 [SMILES: Cc1ccc(CCNc2nc(-c3cccnc3)nc3ccccc23)cc1] | 340 | 1.78 (inh) | $^1$H NMR (500 MHz, CDCl$_3$) δ 9.78 (s, 1H), 8.84 (d, J = 7.9 Hz, 1H), 8.69 (d, J = 3.8 Hz, 1H), 7.93 (d, J = 8.3 Hz, 1H), 7.80-7.68 (m, 1H), 7.59 (d, J = 8.1 Hz, 1H), 7.48-7.37 (m, 2H), 7.22-7.11 (m, 4H), 5.91 (s, 1H), 4.09-3.95 (m, 2H), 3.06 (t, J = 6.9 Hz, 2H), 2.35 (s, 3H). | $^{13}$C NMR (125 MHz, CDCl$_3$) δ 159.6, 158.7, 150.8, 150.3, 150.2, 136.3, 135.9, 135.8, 134.5, 132.8, 129.6, 128.9, 128.8, 126.0, 123.3, 120.5, 114.0, 42.7, 35.0, 21.1 | ESI-MS m/z: 341 (M + H)$^+$ |
| 74 | 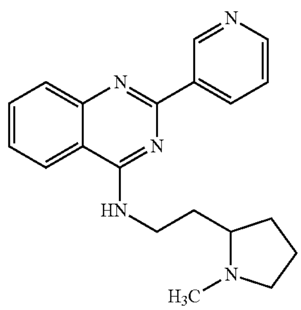 [SMILES: CN1CCCC1CCNc1nc(-c2cccnc2)nc2ccccc12] | 333 | NA | $^1$H NMR (500 MHz, CDCl$_3$) δ 9.74 (d, J = 1.7 Hz, 1H), 8.80 (dt, J = 7.9, 1.9 Hz, 2H), 8.67 (dd, J = 4.8, 1.6 Hz, 1H), 7.88 (d, J = 8.2 Hz, 1H), 7.76-7.65 (m, 1H), 7.61 (d, J = 8.0 Hz, 1H), 7.47-7.33 (m, 2H), 4.18-4.02 (m, 1H), 3.78-3.63 (m, 1H), 3.30-3.13 (m, 1H), 2.63 (s, 1H), 2.48 (s, 3H), 2.37-2.27 (m, 1H), 2.17-2.04 (m, 1H), 2.04-1.68 (m, 6H). | $^{13}$C NMR (125 MHz, CDCl$_3$) δ 159.8, 159.1, 150.6, 150.3, 150.3, 135.7, 134.8, 132.4, 128.7, 125.7, 123.2, 121.1, 114.6, 65.5, 57.2, 40.8, 38.5, 27.9, 27.8, 22.9 | ESI-MS m/z: 334 (M + H)$^+$ |
| 75 | 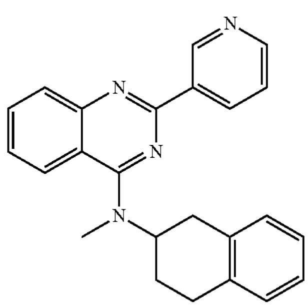 [SMILES: CN(c1nc(-c2cccnc2)nc2ccccc12)C1CCc2ccccc2C1] | 366 | 1.58 (inh) | $^1$H NMR (500 MHz, CDCl$_3$) δ 9.71 (d, J = 1.1 Hz, 1H), 8.80 (d, J = 1.9 Hz, 1H), 8.67 (dd, J = 4.8, 1.6 Hz, 1H), 8.07-7.92 (m, 2H), 7.79-7.66 (m, 1H), 7.45-7.34 (m, 2H), 7.17 (s, 4H), 5.09-4.95 (m, 1H), 3.38 (s, 3H), 3.24 (d, J = 8.5 Hz, 2H), 3.13-2.99 (m, 2H), 2.30-2.21 (m, 1H), 2.21-2.08 (m, 1H). | $^{13}$C NMR (125 MHz, CDCl$_3$) δ 164.3, 157.3, 150.7, 150.2, 135.9, 135.7, 135.2, 134.2, 132.5, 129.5, 128.9, 128.7, 126.3, 126.1, 125.4, 124.8, 123.3, 115.4, 56.6, 34.3, 32.2, 29.7, 27.2 | ESI-MS m/z: 367 (M + H)$^+$ |
| 76 | 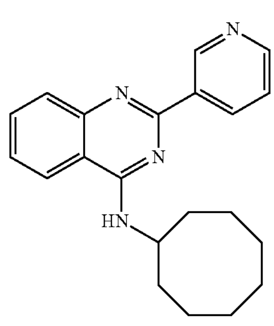 [SMILES: c1cncc(-c2nc(NC3CCCCCCC3)c3ccccc3n2)c1] | 332 | 0.028 (inh) | $^1$H NMR (500 MHz, CDCl$_3$) δ 9.75 (d, J = 1.4 Hz, 1H), 8.82 (d, J = 7.9 Hz, 1H), 8.69 (dd, J = 4.7, 1.4 Hz, 1H), 7.92 (d, J = 8.3 Hz, 1H), 7.76-7.72 (m, 1H), 7.70 (d, J = 8.1 Hz, 1H), 7.51-7.35 (m, 2H), 5.73 (d, J = 6.2 Hz, 1H), 4.73-4.56 (m, 1H), 2.18-2.00 (m, 2H), 2.00-1.43 (m, 12H). | $^{13}$C NMR (125 MHz, CDCl$_3$) δ 158.8, 158.6, 150.7, 150.3, 150.2, 135.8, 134.5, 132.7, 128.9, 125.8, 123.3, 120.5, 114.0, 51.0, 32.7, 27.2, 26.1, 24.2 | ESI-MS m/z: 333 (M + H)$^+$ |

-continued

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 77 | (Trans- structure with 4-methylcyclohexyl) | 318 | 0.020 (inh) | $^1$H NMR (500 MHz, CDCl$_3$) δ 9.75 (s, 1H), 8.80 (d, J = 7.8 Hz, 1H), 8.69 (s, 1H), 7.92 (d, J = 8.3 Hz, 1H), 7.77-7.71 (m, 1H), 7.70 (d, J = 8.2 Hz, 1H), 7.53-7.33 (m, 2H), 5.63 (d, J = 5.3 Hz, 1H), 4.38-4.26 (m, 1H), 2.28 (d, J = 9.9 Hz, 2H), 1.84 (d, J = 12.6 Hz, 2H), 1.54-1.40 (m, 1H), 1.40-1.30 (m, 2H), 1.30-1.14 (m, 3H), 0.98 (d, J = 6.5 Hz, 3H). | $^{13}$C NMR (125 MHz, CDCl$_3$) δ 159.0, 158.8, 150.8, 150.5, 150.4, 135.7, 134.6, 132.7, 129.0, 125.7, 123.2, 120.5, 113.9, 50.4, 34.1, 33.1, 32.3, 22.3 | ESI-MS m/z: 319 (M + H)$^+$ |
| 78 | (norbornyl structure) | 316 | 0.355 (inh) | $^1$H NMR (500 MHz, CDCl$_3$) δ 9.75 (s, 1H), 8.82 (dt, J = 7.9, 1.8 Hz, 1H), 8.68 (d, J = 3.9 Hz, 1H), 7.91 (d, J = 8.3 Hz, 1H), 7.75-7.71 (m, 1H), 7.69 (d, J = 8.2 Hz, 1H), 7.49-7.35 (m, 2H), 5.64 (d, J = 5.5 Hz, 1H), 4.27-4.16 (m, 1H), 2.51 (d, J = 4.1 Hz, 1H), 2.39 (s, 1H), 2.05 (ddd, J = 13.2, 7.9, 2.2 Hz, 1H), 1.73-1.61 (m, 1H), 1.61-1.53 (m, 1H), 1.51 (d, J = 10.1 Hz, 1H), 1.48-1.36 (m, 2H), 1.34-1.20 (m, 2H). | $^{13}$C NMR (125 MHz, CDCl$_3$) δ 158.9, 158.7, 150.7, 150.3, 150.2, 135.8, 134.5, 132.7, 128.9, 125.8, 123.3, 120.5, 113.9, 55.1, 42.1, 41.0, 36.0, 35.9, 28.3, 26.7 | ESI-MS m/z: 317 (M + H)$^+$ |
| 79 | (adamantyl structure) | 356 | 1.12 (inh) | $^1$H NMR (500 MHz, CDCl$_3$) δ 9.73 (d, J = 1.6 Hz, 1H), 8.83 (d, J = 7.8 Hz, 1H), 8.69 (dd, J = 4.7, 1.5 Hz, 1H), 7.92 (d, J = 8.1 Hz, 1H), 7.80-7.69 (m, 1H), 7.66 (d, J = 8.1 Hz, 1H), 7.51-7.32 (m, 2H), 5.58 (s, 1H), 2.38 (d, J = 2.3 Hz, 6H), 2.25-2.18 (m, 3H), 1.88-1.74 (m, 6H). | $^{13}$C NMR (125 MHz, CDCl$_3$) δ 159.0, 158.1, 150.7, 150.3, 135.8, 134.5, 132.6, 128.9, 125.9, 123.3, 120.6, 114.2, 53.6, 41.7, 36.7, 29.7 | ESI-MS m/z: 357 (M + H)$^+$ |
| 80 | (S)-tetrahydronaphthyl structure | 352 | 0.006 (inh) | $^1$H NMR (500 MHz, CDCl$_3$) δ 9.75 (s, 1H), 8.82 (d, J = 7.9 Hz, 1H), 8.68 (d, J = 3.7 Hz, 1H), 7.95 (d, J = 8.3 Hz, 1H), 7.75 (t, J = 7.7 Hz, 1H), 7.70 (d, J = 8.1 Hz, 1H), 7.47-7.42 (m, 1H), 7.41 (dd, J = 7.9, 4.8 Hz, 1H), 7.24-7.11 (m, 4H), 5.87 (d, J = 5.2 Hz, 1H), 5.00-4.87 (m, 1H), 3.43 (dd, J = 16.2, 5.0 Hz, 1H), 3.12-2.88 (m, 3H), 2.40-2.30 (m, 1H), 2.13-2.01 (m, 1H). | $^{13}$C NMR (125 MHz, CDCl$_3$) δ 159.2, 158.7, 150.8, 150.2, 135.8, 135.7, 134.3, 134.1, 132.9, 129.7, 129.1, 128.9, 126.4, 126.2, 126.0, 123.3, 120.7, 113.9, 47.1, 35.8, 28.5, 27.5 | ESI-MS m/z: 353 (M + H)$^+$ |

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 81 | 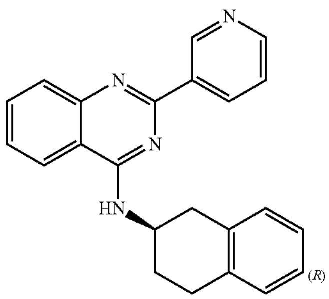 | 352 | 0.010 (inh) | $^{1}$H NMR (500 MHz, CDCl$_3$) δ 9.75 (s, 1H), 8.82 (d, J = 7.9 Hz, 1H), 8.68 (d, J = 3.7 Hz, 1H), 7.95 (d, J = 8.3 Hz, 1H), 7.75 (t, J = 7.7 Hz, 1H), 7.70 (d, J = 8.1 Hz, 1H), 7.47-7.42 (m, 1H), 7.41 (dd, J = 7.9, 4.8 Hz, 0H), 7.24-7.11 (m, 4H), 5.87 (d, J = 5.2 Hz, 1H), 5.00-4.87 (m, 1H), 3.43 (dd, J = 16.2, 5.0 Hz, 1H), 3.12-2.88 (m, 3H), 2.40-2.30 (m, 1H), 2.13-2.01 (m, 1H). | $^{13}$C NMR (125 MHz, CDCl$_3$) δ 159.2, 158.7, 150.8, 150.2, 135.8, 135.7, 134.3, 134.1, 132.9, 129.7, 129.1, 128.9, 126.4, 126.2, 126.0, 123.3, 120.7, 113.9, 47.1, 35.8, 28.5, 27.5 | ESI-MS m/z: 353 (M + H)$^+$ |
| 82 | 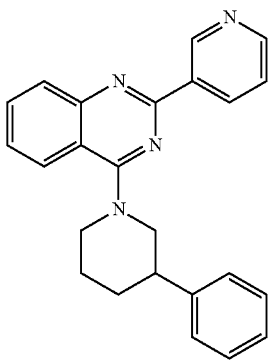 [SMILES: c1ccc(C2CCCN(c3nc(-c4cccnc4)nc4ccccc34)C2)cc1] | 366 | Weak (act) | $^{1}$H NMR (500 MHz, CDCl$_3$) δ 9.68 (s, 1H), 8.73 (d, J = 7.9 Hz, 1H), 8.61 (d, J = 3.9 Hz, 1H), 7.87 (dd, J = 17.0, 8.3 Hz, 2H), 7.66 (t, J = 7.6 Hz, 1H), 7.38-7.27 (m, 4H), 7.26-7.18 (m, 3H), 4.58-4.45 (m, 2H), 3.24-3.13 (m, 2H), 3.08-2.98 (m, 1H), 2.12 (d, J = 12.3 Hz, 1H), 1.96-1.73 (m, 3H). | $^{13}$C NMR (125 MHz, CDCl$_3$) δ 165.0, 157.7, 152.8, 150.8, 150.3, 143.5, 135.7, 134.3, 132.6, 129.0, 128.8, 127.2, 126.9, 125.3, 125.2, 123.2, 115.8, 56.6, 50.8, 42.8, 32.2, 25.9 | ESI-MS m/z: 367 (M + H)$^+$ |
| 83 | 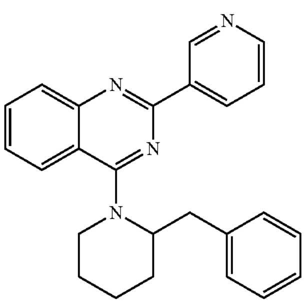 [SMILES: c1ccc(CC2CCCCN2c2nc(-c3cccnc3)nc3ccccc23)cc1] | 380 | 2.24 (act) | $^{1}$H NMR (500 MHz, CDCl$_3$) δ 9.72 (s, 1H), 8.76 (d, J = 7.9 Hz, 1H), 8.69 (d, J = 4.6 Hz, 1H), 7.90 (d, J = 8.4 Hz, 1H), 7.73 (d, J = 8.3 Hz, 1H), 7.70 (d, J = 7.0 Hz, 1H), 7.40 (dd, J = 7.8, 4.9 Hz, 1H), 7.36 (d, J = 7.1 Hz, 1H), 7.22-7.08 (m, 5H), 5.03 (d, J = 5.1 Hz, 1H), 4.30 (d, J = 13.2 Hz, 1H), 3.68-3.55 (m, 1H), 3.26 (dd, J = 13.5, 6.6 Hz, 1H), 3.09 (dd, J = 13.5, 8.8 Hz, 1H), 2.05-1.54 (m, 6H). | $^{13}$C NMR (125 MHz, CDCl$_3$) δ 165.2, 157.7, 152.9, 150.7, 150.4, 139.0, 135.7, 134.5, 132.4, 129.2, 128.8, 128.5, 126.4, 125.1, 124.7, 123.2, 115.6, 58.0, 45.4, 35.8, 27.3, 25.9, 19.5 | ESI-MS m/z: 381 (M + H)$^+$ |
| 84 | 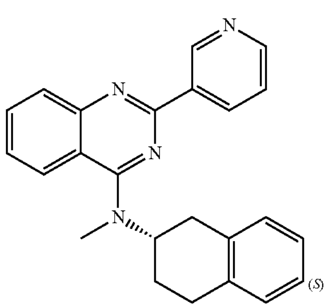 | 366 | 0.50 Inhibitor | $^{1}$H NMR (500 MHz, CDCl$_3$) δ 9.71 (d, J = 1.1 Hz, 1H), 8.80 (d, J = 1.9 Hz, 1H), 8.67 (dd, J = 4.8, 1.6 Hz, 1H), 8.07-7.92 (m, 2H), 7.79-7.66 (m, 1H), 7.45-7.34 (m, 2H), 7.17 (s, 4H), 5.09-4.95 (m, 1H), 3.38 (s, 3H), 3.24 (d, J = 8.5 Hz, 2H), 3.13-2.99 (m, 2H), 2.30-2.21 (m, 1H), 2.21-2.08 (m, 1H). | $^{13}$C NMR (125 MHz, CDCl$_3$) δ 164.3, 157.3, 150.7, 150.2, 135.9, 135.7, 135.2, 134.2, 132.5, 129.5, 128.9, 128.7, 126.3, 126.1, 125.4, 124.8, 123.3, 115.4, 56.6, 34.3, 32.2, 29.7, 27.2 | ESI-MS m/z: 367 (M + H)$^+$ |

-continued

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 85 | 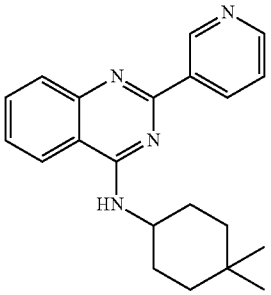 [SMILES: CC1(C)CCC(Nc2nc(-c3cccnc3)nc3ccccc23)CC1] | 332 | 0.46 (inh) | $^1$H NMR (500 MHz, CDCl$_3$) δ 9.74 (s, 1H), 8.80 (d, J = 7.9 Hz, 1H), 8.69 (d, J = 3.7 Hz, 1H), 7.90 (s, 1H), 7.79-7.63 (m, 2H), 7.45 (s, 1H), 7.41 (d, J = 3.1 Hz, 1H), 5.66 (d, J = 5.5 Hz, 1H), 4.43-4.25 (m, 1H), 2.16-2.00 (m, 2H), 1.64-1.38 (m, 6H), 1.01 (d, J = 3.0 Hz, 6H). | $^{13}$C NMR (125 MHz, CDCl$_3$) δ 159.0, 158.8, 150.8, 150.4, 135.7, 134.5, 132.7, 129.0, 125.8, 123.2, 120.6, 113.9, 50.3, 37.9, 31.8, 29.9, 28.7, 25.2 | ESI-MS m/z: 366 (M + H)$^+$ |
| 86 | 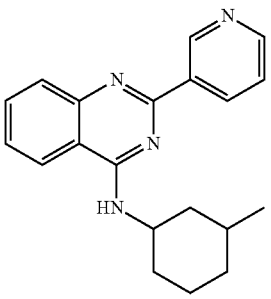 [SMILES: CC1CCCC(Nc2nc(-c3cccnc3)nc3ccccc23)C1] | 318 | 0.079 (inh) | 1:1 mixture | | ESI-MS m/z: 319 (M + H)$^+$ |
| 87 | 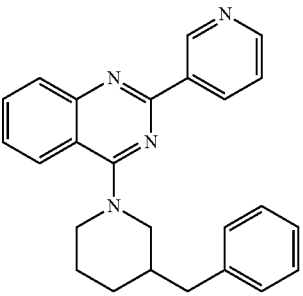 [SMILES: c1ccc(CC2CCCN(c3nc(-c4cccnc4)nc4ccccc34)C2)cc1] | 380 | 2.51 (act) | $^1$H NMR (500 MHz, CDCl$_3$) δ 9.70 (s, 1H), 8.68 (d, J = 7.6 Hz, 2H), 7.92 (d, J = 8.2 Hz, 1H), 7.71-7.59 (m, 2H), 7.38 (d, J = 4.8 Hz, 1H), 7.36-7.29 (m, 2H), 7.24 (t, J = 8.2 Hz, 2H), 7.21 (d, J = 7.1 Hz, 2H), 4.43 (dd, J = 30.6, 13.0 Hz, 2H), 3.30-3.14 (m, 1H), 2.91 (dd, J = 13.0, 10.7 Hz, 1H), 2.69 (dd, J = 13.5, 6.5 Hz, 1H), 2.60 (dd, J = 13.5, 8.1 Hz, 1H), 2.24-2.08 (m, 1H), 2.06-1.95 (m, 1H), 1.95-1.84 (m, 1H), 1.84-1.67 (m, 1H), 1.48-1.30 (m, 1H). | $^{13}$C NMR (125 MHz, CDCl$_3$) δ 164.6, 157.6, 152.7, 150.7, 150.3, 139.8, 135.7, 132.5, 129.1, 128.8, 128.6, 126.3, 125.1, 125.0, 123.3, 115.5, 55.6, 50.6, 40.7, 38.6, 31.7, 25.7 | ESI-MS m/z: 381 (M + H)$^+$ |
| 88 | 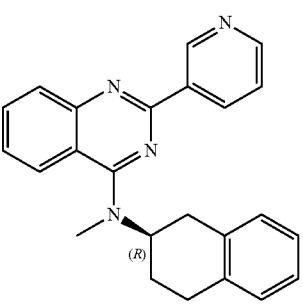 | 366 | Weak (inh) | $^1$H NMR (500 MHz, CDCl$_3$) δ 9.71 (d, J = 1.1 Hz, 1H), 8.80 (d, J = 7.9 Hz, 1H), 8.67 (dd, J = 4.8, 1.6 Hz, 1H), 8.07-7.92 (m, 2H), 7.79-7.66 (m, 1H), 7.45-7.34 (m, 2H), 7.17 (s, 4H), 5.09-4.95 (m, 1H), 3.38 (s, 3H), 3.24 (d, J = 8.5 Hz, 2H), 3.13-2.99 (m, 2H), 2.30-2.21 (m, 1H), 2.21-2.08 (m, 1H). | $^{13}$C NMR (125 MHz, CDCl$_3$) δ 164.3, 157.3, 150.7, 150.2, 135.9, 135.7, 135.2, 134.2, 132.5, 129.5, 128.9, 128.7, 126.3, 126.1, 125.4, 124.8, 123.3, 115.4, 56.6, 34.3, 32.2, 29.7, 27.2 | ESI-MS m/z: 367 (M + H)$^+$ |

-continued

Table of Substituted Quinazoline Compounds

| No. | Structures | MW | IC$_{50}$ or AC$_{50}$ (μM) | 1H NMR | 13C NMR | Mass |
|---|---|---|---|---|---|---|
| 89 | 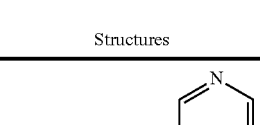 | 464 | 0.168 (inh) | $^1$H NMR (500 MHz, CDCl$_3$) δ 9.77 (d, J = 1.7 Hz, 1H), 8.80 (dt, J = 7.9, 1.8 Hz, 1H), 8.68 (dd, J = 4.8, 1.5 Hz, 1H), 7.92 (d, J = 8.3 Hz, 1H), 7.78-7.71 (m, 1H), 7.69 (d, J = 8.1 Hz, 1H), 7.62 (s, 1H), 7.53 (d, J = 7.9 Hz, 1H), 7.45-7.37 (m, 2H), 7.03 (d, J = 7.9 Hz, 1H), 6.03 (d, J = 6.7 Hz, 1H), 5.32-5.25 (m, 1H), 3.54 (td, J = 16.4, 7.1 Hz, 2H), 3.04 (td, J = 15.9, 4.7 Hz, 2H). | $^{13}$C NMR (125 MHz, CDCl$_3$) δ 159.3, 158.6, 150.9, 150.4, 150.3, 143.9, 140.9, 136.0, 135.7, 134.4, 134.1, 132.9, 129.0, 126.9, 126.0, 123.3, 120.7, 113.9, 92.0, 52.5, 39.9, 39.9 | ESI-MS m/z: 465 (M + H)$^+$ |

Example 7—Design and Synthesis of Potent Quinazolines as Selective β-Glucocerebrosidase Modulators Abstract Gaucher's disease is a common genetic disease caused by mutations in the β-glucocerebrosidase (GBA1) gene that have been also linked to increased risk of Parkinson's disease and Lewy Body Dementia. Stabilization of misfolded mutant fl-glucocerebrosidase (GCase) represents an important therapeutic strategy in synucleinopathies. Here we report a novel class of GCase quinazoline inhibitors, obtained in a high throughput screening, with moderate potency against wild-type GCase. Rational design and a SAR study of this class of compounds led to a new series of quinazoline derivatives with single digit nanomolar potency. These compounds were shown to selectively stabilize GCase when compared to other lysosomal enzymes and to increase N370S mutant GCase protein concentration and activity in cell assays. To the best of our knowledge, these molecules are the most potent non-iminosugar GCase inhibitors to date that may prove useful for future mechanistic and preclinical studies in Gaucher's and Parkinson's diseases.

Introduction

Gaucher's disease (GD), the most common lysosomal storage disease, is caused by a recessively inherited deficiency in β-glucocerebrosidase (GCase) and subsequent accumulation of glucoceramides, toxic lipid substrates[1,2]. Substrate accumulation leads to hepatosplenomegaly, bone marrow suppression, and bone lesions[1-3]. Many of the GCase mutations are missense mutations[4] that result in single amino acid substitutions of the enzyme. Most of these mutations, including the prevalent N370S mutation, are still functional, although with very low residual GCase activity[5] due to enzyme misfolding, and proteasome-mediated breakdown[5]. Current treatments for GD include enzyme replacement therapy (ERT) and substrate reduction therapy (SRT)[2,6]. In recent years, mutations in GBA1 were also found to be a major risk factor for Parkinson's disease (PD) and dementia with Lewy bodies (DLB)[7-11]. Accumulation of β-glucosylceramide, the substrate of GCase, in neurons promotes the formation of α-synuclein oligomers, which are considered toxic in PD[12]. Enhancement of GCase activity is thought to be a potential therapeutic strategy for GCase-associated synucleinopathies, including PD[13,14].

An emerging therapeutic approach involves the restoration of proper folding and lysosome delivery of degradation-prone mutant enzymes using small molecules as pharmacological chaperones (PCs)[5]. Previous studies have shown that iminosugars increase the cellular activity of the N370S mutant form of GCase[15,16], as well as of the wild-type enzyme[5,17]. Isofagomine (IFG, 1) attracted the most attention in the iminosugar class of compounds (FIG. 1)[18]. However, iminosugars tend to have poor selectivity and relatively short half-lives in cells[19]. Several different scaffolds of non-iminosugar inhibitors (2 and 3 are examples in FIG. 1) have been reported as GCase PCs since 2007[20-24]; however, the mechanism of these non-iminosugar PCs remains unknown.

In our high throughput screening effort to discover potent GCase modulators, compound 4 (FIG. 1) was identified as a potent GCase inhibitor (IC$_{50}$ 0.177 μM) in a 4-methylumbelliferyl β-D-glucopyranoside (4MU-β-Glc) enzyme activity based high throughput screen. The activity was confirmed with additional synthesized compounds. To further develop potent GCase inhibitors and use them for in vitro mechanistic studies, we carried out a structure activity relationship (SAR) study of a series of quinazoline derivatives, leading to the discovery of single digit nanomolar potency GCase inhibitory modulators.

Chemistry

The synthesis of compound 4 and its analogues for SAR exploration is straightforward and is detailed in Schemes 1 and 2 below. As showed in Scheme 1, 5 was prepared from 2-amino-benzonitrile and nicotinoyl chloride according to a known method[25]. The reaction of 5 and appropriate amines in the presence of potassium carbonate as a base afforded 4, 6a-6i, 7a-7i, 8a-8g, and 9a-9f.

Scheme 1. Synthesis of 4, 6a-6i, 7a-7i, 8a-8g, and 9a-9f with substituents on the secondary amine

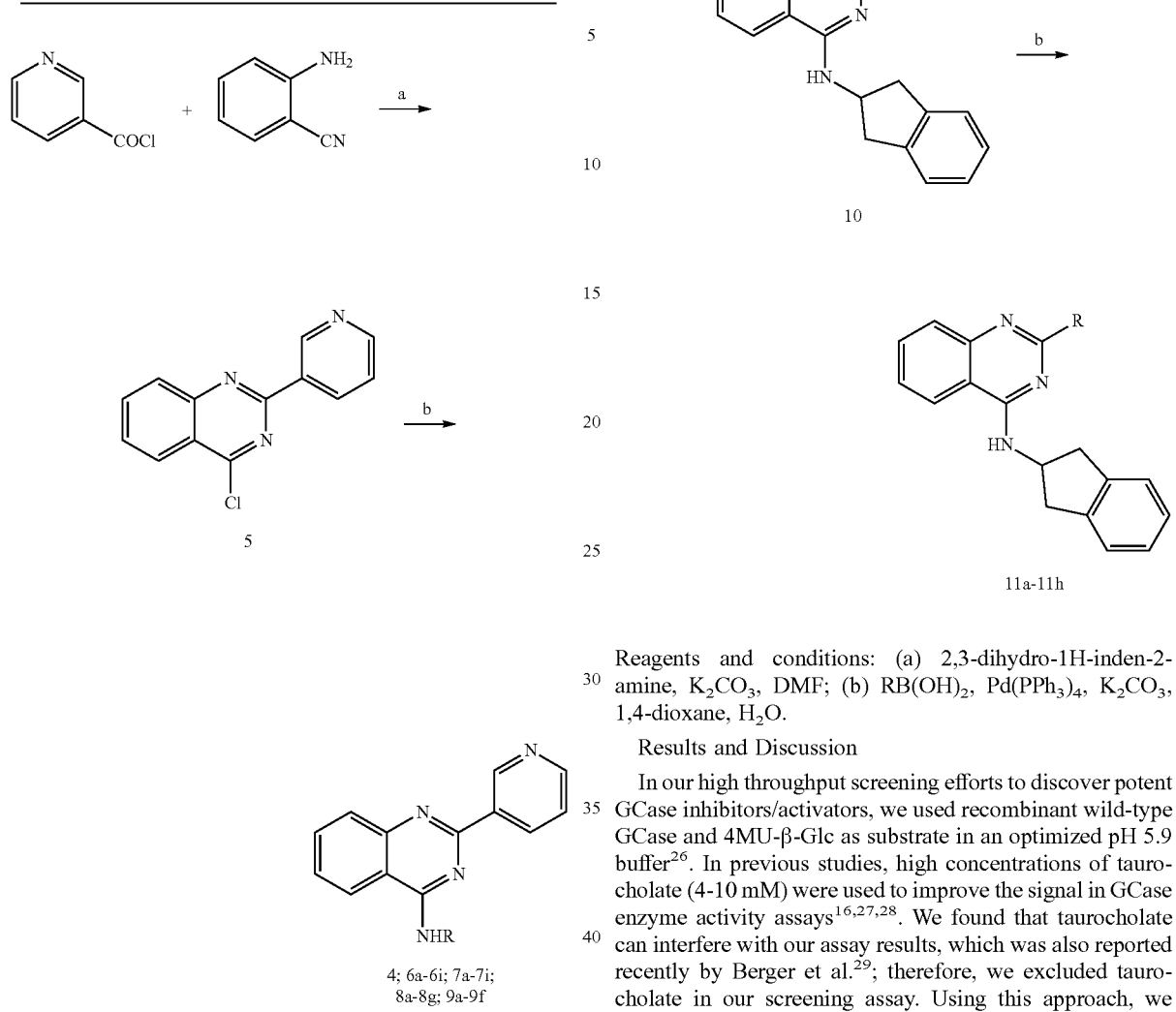

Reagents and conditions: (a) (i) sulfolane (ii) PCl$_5$; (b) RNH$_2$, K$_2$CO$_3$, DMF Additional analogues having modifications at position 2 of the quinazoline ring were synthesized, employing alkylation of 2,3-dihydro-1H-inden-2-amine with 2,4-dichloroquinazoline, followed by Suzuki coupling with appropriate boronic acids to afford 11a-11h (Scheme 2). The structure and purity of all the prepared compounds were confirmed by spectroscopic and analytical techniques.

Scheme 2. Synthesis of 11a-11b with modifications at the 2-position of the quinazoline ring

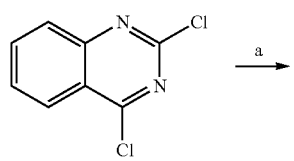

Reagents and conditions: (a) 2,3-dihydro-1H-inden-2-amine, K$_2$CO$_3$, DMF; (b) RB(OH)$_2$, Pd(PPh$_3$)$_4$, K$_2$CO$_3$, 1,4-dioxane, H$_2$O.

Results and Discussion

In our high throughput screening efforts to discover potent GCase inhibitors/activators, we used recombinant wild-type GCase and 4MU-β-Glc as substrate in an optimized pH 5.9 buffer[26]. In previous studies, high concentrations of taurocholate (4-10 mM) were used to improve the signal in GCase enzyme activity assays[16,27,28]. We found that taurocholate can interfere with our assay results, which was also reported recently by Berger et al.[29]; therefore, we excluded taurocholate in our screening assay. Using this approach, we discovered several different scaffolds of GCase inhibitors and activators with moderate activity. Among these, we identified a quinazoline compound (4, FIG. 1) as a potent GCase inhibitor. The quinazoline ring had previously been found as the best scaffold for GCase inhibitors among several ring systems assayed[21]. Here we describe our modifications of the substituents on the quinazoline ring.

To examine the SAR at the amino group, a series of substituents was introduced at the 4-position of the N-cyclohexyl ring of 4 (Table 1). A 4-methyl substituent (6a, cis/trans=3/2 mixture) resulted in 3-fold higher activity (IC$_{50}$ 56 nM), while 4-ethyl substitution (6b, cis/trans=3/2 mixture) did not show a significant change of activity, suggesting that a smaller hydrophobic group at this position may be beneficial. Then, a trans-4-methyl compound (6c) was synthesized, which exhibited great improvement of inhibitory activity (IC$_{50}$ 20 nM). Further modification by installation of 4-methoxyl (6d), 4,4-dimethyl (6e), or 4,4-difluoro (60 groups at the same position decreased the potency; amino substituents were detrimental to activity. Replacement of the cyclohexyl group by tetrahydro-2H-pyran-3-yl (6h), or N-substituted piperidine (6i-6k) afforded weak or inactive compounds, supporting the importance of the lipophilic cyclohexyl ring.

TABLE 1

Structure and inhibitory activity of 2-(pyridin-3-yl)quinazoline derivatives with substituted cyclohexyl and related rings[a]

| Comp. | R | IC$_{50}$ (µM) |
|---|---|---|
| 4 | cyclohexyl | 0.177 ± 0.012 |
| 6a | 4-methylcyclohexyl (Cis/Trans: 3/2) | 0.056 ± 0.005 |
| 6b | 4-ethylcyclohexyl (Cis/Trans: 3/2) | 0.126 ± 0.007 |
| 6c | 4-methylcyclohexyl (trans) | 0.020 ± 0.002 |
| 6d | 4-methoxycyclohexyl | 0.251 ± 0.018 |
| 6e | 4,4-dimethylcyclohexyl | 0.431 ± 0.042 |
| 6f | 4,4-difluorocyclohexyl | 0.234 ± 0.017 |
| 6g | 4-(dimethylamino)cyclohexyl | Inactive |
| 6h | tetrahydropyran-3-yl | 0.891 ± 0.023 |
| 6i | 1-methylpiperidin-4-yl | Inactive |
| 6j | 1-isopropylpiperidin-4-yl | 33.21 ± 9.71 |
| 6k | 1-(pyridin-2-ylmethyl)piperidin-4-yl | 36.07 ± 8.72 |

[a]Experiments were performed in triplicate, and the mean ± SD is shown.

Results and Discussion

To further expand the SAR of the amino group, the cyclohexyl ring of 4 was replaced by a series of saturated carbon rings of different sizes. A dramatic SAR was observed with different carbon rings (7a-7e). As shown in Table 2, the larger cycloalkyl rings were more potent; the compound with a cyclooctyl group (7a, IC$_{50}$ 27 nM) was the most potent. However, when bulk was introduced to the cycloalkyl ring, the potency of the compounds (7f and 7g) decreased, suggesting that the hydrophobic binding pocket may be compact. Introduction of one or two carbons between the cyclohexyl and NH groups (7h and 7i) in 4 decreased the inhibitory activity, again indicating a hydrophobic pocket with limited volume.

TABLE 2

Structure and inhibitory activity of 2-(pyridin-3-yl)quinazoline derivatives with saturated alkyl rings[a]

[2-(pyridin-3-yl)quinazoline core with 4-HN-R substituent]

| Comp. | R | IC$_{50}$ (µM) |
|---|---|---|
| 7a | cyclooctyl | 0.027 ± 0.002 |
| 7b | cycloheptyl | 0.042 ± 0.003 |
| 7c | cyclopentyl | 0.72 ± 0.05 |
| 7d | cyclobutyl | 2.84 ± 0.34 |
| 7e | cyclopropyl | 28.07 ± 3.21 |
| 7f | 1-adamantyl | 0.926 ± 0.08 |
| 7g | 2-norbornyl | 0.282 ± 0.043 |
| 7h | cyclohexylmethyl | 0.405 ± 0.040 |
| 7i | 2-cyclohexylethyl | 0.857 ± 0.033 |

[a]Experiments were performed in triplicate, and the mean ± SD is shown.

To understand the nature of the binding site, a phenyl ring with different length linkers was introduced into the molecules (8a-e, Table 3). Compound 8a, by replacement of the cyclohexyl ring in 4 with a phenyl ring, lost activity. Insertion of a 1-4 carbon linker between the phenyl and quinazoline rings gave 8b-8e. Interestingly, 8c, with a phenylethyl group, was slightly more potent than 4. Extension of the linker did not benefit activity, suggesting that a two carbon length linker between the phenyl ring and secondary amino group of 8c may allow optimal binding of the phenyl group. Substitution of the phenyl group in 8 with a 2- or 3-pyridine ring (8f or 8g) sharply diminished potency, indicating a repulsive effect of the pyridine nitrogen atom.

TABLE 3

Structure and inhibitory activity of 2-(pyridin-3-yl)quinazoline derivatives with aromatic rings[a]

[2-(pyridin-3-yl)quinazoline core with 4-HN-R substituent]

| Comp. | R | IC$_{50}$ (µM) |
|---|---|---|
| 8a | phenyl | inactive |
| 8b | benzyl | 5.77 ± 0.82 |

TABLE 3-continued

Structure and inhibitory activity of 2-(pyridin-3-yl)quinazoline derivatives with aromatic rings[a]

| Comp. | R | IC$_{50}$ (µM) |
|---|---|---|
| 8c | –CH$_2$CH$_2$–Ph | 0.097 ± 0.009 |
| 8d | –CH$_2$CH$_2$CH$_2$–Ph | 1.53 ± 0.22 |
| 8e | –CH$_2$CH$_2$CH$_2$CH$_2$–Ph | 1.28 ± 0.13 |
| 8f | –CH$_2$CH$_2$–(2-pyridyl) | 1.40 ± 0.12 |
| 8g | –CH$_2$CH$_2$–(3-pyridyl) | 4.29 ± 0.57 |

[a]Experiments were performed in triplicate, and the mean ± SD is shown.

Figure 2:
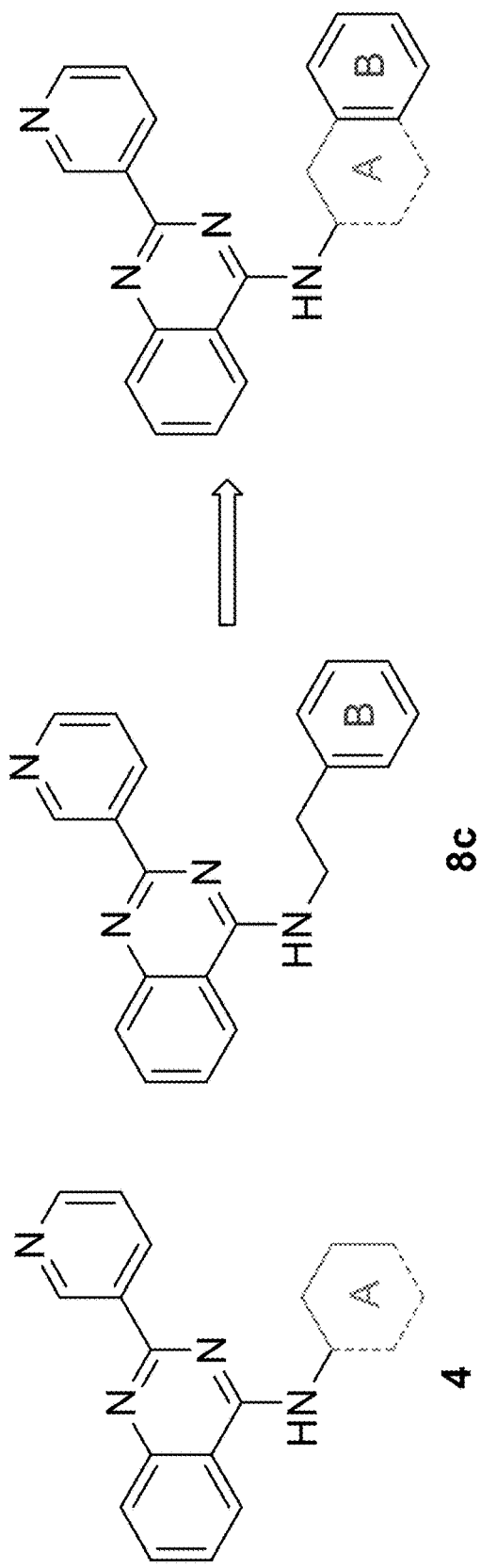
FIG. 2. Rational design of a new series of potent quinazoline inhibitors.

To enhance the binding affinity of the compounds with GCase, a new series of compounds was designed to integrate both the hydrophobic interaction of the A ring and the π-π interaction of the B ring by fusing the cyclohexyl ring (4) with a phenyl ring (FIG. 2 and Table 4). These derivatives (9a-c) exhibited single digit nanomolar inhibitory activity against GCase. Stereochemistry did not seem to be important (9a and 9b). The compound with an indane ring (9c) gave comparable activity to that of the tetralin ring (9a). Attachment of the quinazoline ring to the tetralin ring (9d) and indane ring (9e) at position 1 instead of position 2 (9a and 9c) dramatically increased the IC$_{50}$ values to the low micromolar range, indicating the importance of the orientation of this substituent for binding activity of these inhibitors. The introduction of an oxygen atom to give a chromane (9f) did not significantly affect the potency. These results suggest important hydrophobic and π-π interactions in the binding of this series of compounds to GCase.

TABLE 4

Structure and inhibitory activity of 2-(pyridin-3-yl)quinazoline derivatives with fused rings[a]

| Comp. | R | IC$_{50}$ (nM) |
|---|---|---|
| 9a | (S)-tetralin-2-yl | 8.7 ± 1.1 |
| 9b | (R)-tetralin-2-yl | 9.9 ± 1.3 |
| 9c | indan-2-yl | 8.3 ± 1.0 |
| 9d | tetralin-1-yl | 872 ± 71 |
| 9e | indan-1-yl | 821 ± 73 |

[a]Experiments were performed in triplicate, and the mean ± SD is shown.

Finally, we examined the substituent effect on the pyridine ring. A methyl group was introduced at different positions of the 3-pyridinyl ring of 9c to give 11a-c (Table 5). Methylation of the pyridine ring decreased the potency. Whereas the compound with a methyl group at position 4 of the pyridinyl ring (11a) showed only moderate potency, the other two compounds (11b and 11c) with a methyl group at positions 5- and 6 were much more potent, comparable to that when a 2-furanyl group replaced the pyridine ring, but still not as potent as 9c. The replacement of the 3-pyridinyl ring in 9c with either phenyl or 3-thienyl groups, however, gave compounds that retained the same potency as 9c, suggesting that more groups could be introduced at position 2 of the quinazoline ring.

TABLE 5

Structure and inhibitory activity of 4-(2,3-dihydro-1H-2-indenamino)quinazoline derivatives with aromatic rings[a]

| Comp. | R | IC$_{50}$ (nM) |
|---|---|---|
| 11a | 4-methyl-3-pyridinyl | 122 ± 12 |
| 11b | 5-methyl-3-pyridinyl | 12.5 ± 1.7 |
| 11c | 6-methyl-3-pyridinyl | 29.4 ± 3.6 |
| 11d | phenyl | 6.5 ± 0.7 |
| 11e | 4-pyridinyl | 168 ± 18 |
| 11f | 3-thienyl (2-thienyl) | 8.2 ± 1.0 |
| 11g | 3-thienyl | 5.2 ± 0.6 |
| 11h | 2-furyl | 21.1 ± 2.4 |

[a]Experiments were performed in triplicate, and the mean ± SD is shown.

We also evaluated the activity of these selected compounds at various pH conditions (Table 6). Interestingly, compared to the inhibitory activity at pH 5.9, the activity of 9a, 9b and 9c with a 3-pyridinyl ring decreased by 3 fold at pH 5.0, suggesting the pyridine ring was protonated at pH 5.0 and interfered with the binding affinity to GCase, while the activity of 11d, 11f, and 11g only dropped slightly at both pH conditions. This result may be applied to the design of a pH sensitive compound with a protonatable group to differentiate the inhibitory activity at acidic and neutral pH conditions.

TABLE 6

GCase inhibitory activity of 9a, 9b, 9c, 11d, 11g and 11f at pH 5.0, pH 5.9, and pH 7.0[a]

| Comp | Structure | IC$_{50}$ (nM) | | |
|---|---|---|---|---|
| | | pH 5.0 | pH 5.9 | pH 7.0 |
| 9a | 2-(3-pyridinyl)-4-(tetrahydronaphthalenyl)amino quinazoline | 22.4 ± 3.4 | 8.7 ± 1.1 | 16.9 ± 2.7 |
| 9b | 2-(3-pyridinyl)-4-(tetrahydronaphthalenyl)amino quinazoline | 30.1 ± 4.5 | 9.9 ± 1.3 | 18.8 ± 2.5 |
| 9c | 2-(3-pyridinyl)-4-(indanyl)amino quinazoline | 25.9 ± 3.9 | 8.3 ± 1.0 | 12.7 ± 1.4 |
| 11d | 2-phenyl-4-(indanyl)amino quinazoline | 10.5 ± 1.5 | 6.5 ± 0.7 | 9.4 ± 1.4 |
| 11f | 2-(2-thienyl)-4-(indanyl)amino quinazoline | 13.9 ± 1.9 | 8.2 ± 1.0 | 12.9 ± 2.0 |

TABLE 6-continued

GCase inhibitory activity of 9a, 9b, 9c, 11d, 11g and 11f at pH 5.0, pH 5.9, and pH 7.0[a]

| Comp | Structure | IC$_{50}$ (nM) | | |
|---|---|---|---|---|
| | | pH 5.0 | pH 5.9 | pH 7.0 |
| 11g | (structure) | 8.9 ± 1.3 | 5.2 ± 0.6 | 6.6 ± 1.0 |

[a]Experiments were performed in triplicate, and the mean ± SD is shown.

Figure 3:
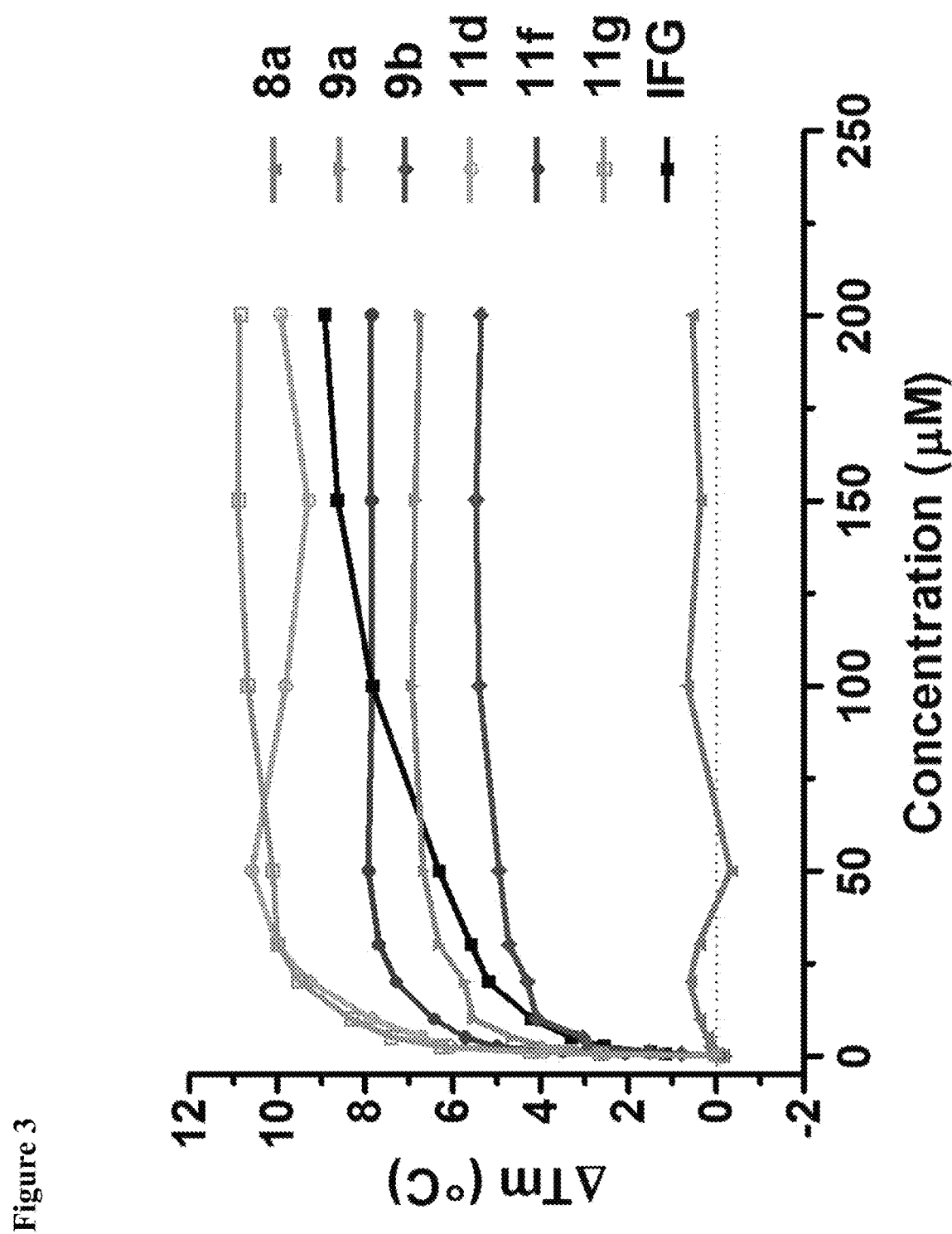
FIG. 3. Fluorescent thermal shift analysis of selected compounds. Compound 9a, 9b, 11d, 11f, 11g, and IFG showed their ability to stabilize wild-type GCase in a dose-dependent manner. Data represent the results of three independent experiments performed with three replicates per sample.

Compounds shown to act as pharmacological chaperones for GCase (or other lysosomal enzymes) also stabilize the enzyme against thermal denaturation. A fluorescent thermal shift assay was developed to evaluate the binding affinity of ligands with protein[30]. To evaluate their abilities to stabilize GCase, the most potent compounds, 9a, 9b, 11d, 11g and 11f were accessed in a wild-type GCase fluorescent thermal shift assay with a negative control (8a) and a positive control (IFG) at pH 5.0. The selected compounds increased the GCase melting point in a dose-dependent manner (FIG. 3), while inactive compound 8a did not change the melting points significantly. Most compounds exhibited greater ability to stabilize GCase than IFG at lower concentrations, and 11g showed the maximum thermal shift up to around 11° C. The maximum thermal shift of these compounds corresponded to their inhibitory activity at pH 5.0.

Figure 4:
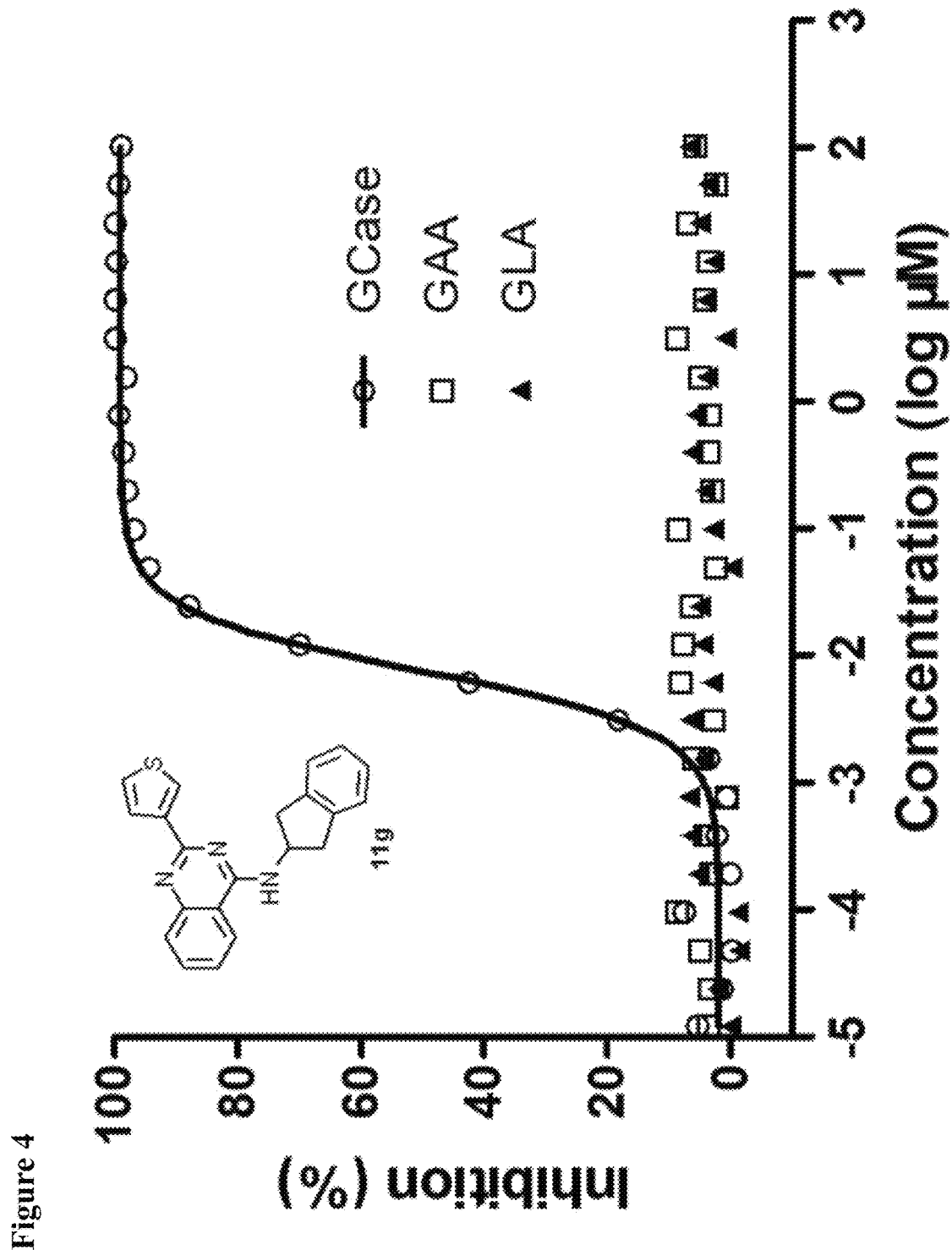
FIG. 4. Selectivity of inhibitor 11g with related hydrolases. 11g was tested on GCase, acid α-glucosidase (GAA), and α-galactosidase A (GLA). Data represent the results of three independent experiments performed with three replicates per sample.

The selected compounds (9a, 9b, 11d, 11g, and 11f) were further evaluated against two other lysosomal hydrolases, acid α-glucosidase (GAA) and α-galactosidase A (GLA). The activities of tested enzymes were not significantly changed by compound treatments up to 100 μM (representative results shown for 11g in FIG. 4).

Figure 5:
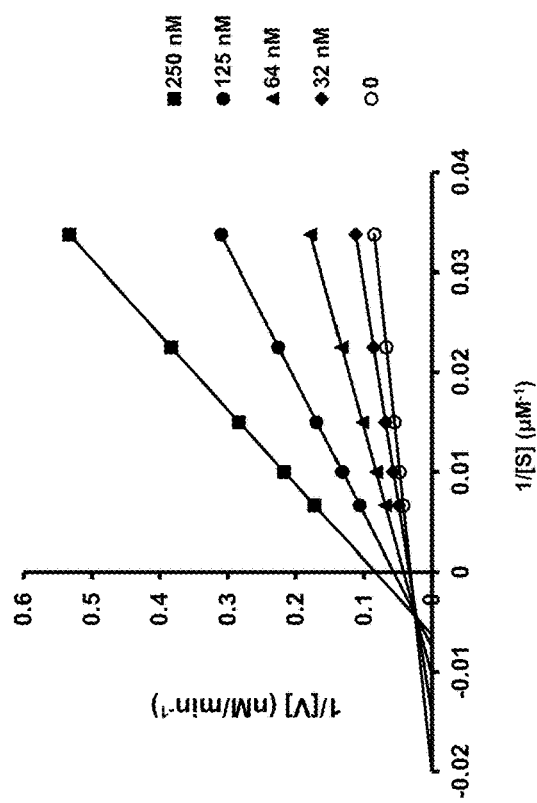
FIG. 5. Lineweaver-Burk plots of the enzyme kinetics of GCase inhibitors (A) 4 and (B) 11g. Each inhibitor was tested in triplicate in two independent assays at the concentrations shown in the legend box of each graph, with (∘) indicating the absence of inhibitor. (A) Compounds 4 and (B) Compound 11g showed an increase in $K_m$ and a decrease in $V_{max}$, indicating linear mixed inhibition.
Figure 5:
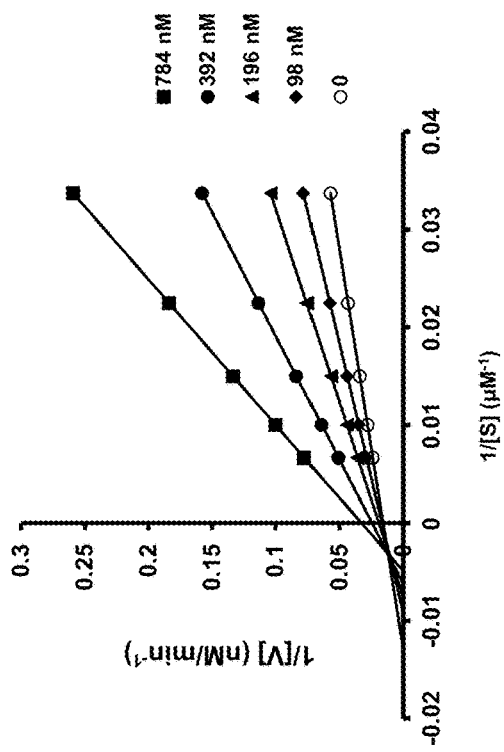

We further tested compounds 4 and 11g by measuring GCase activity at various substrate concentrations (30-150 μM) and in the absence or presence of increasing concentrations of GCase inhibitors. Similarly to reported non-iminosugar inhibitors[20], both of our inhibitors exhibited linear mixed inhibition, with an increase in $K_m$ and decrease in $V_{max}$ values upon increasing inhibitor concentrations (FIGS. 5A and 5B).

Figure 6:
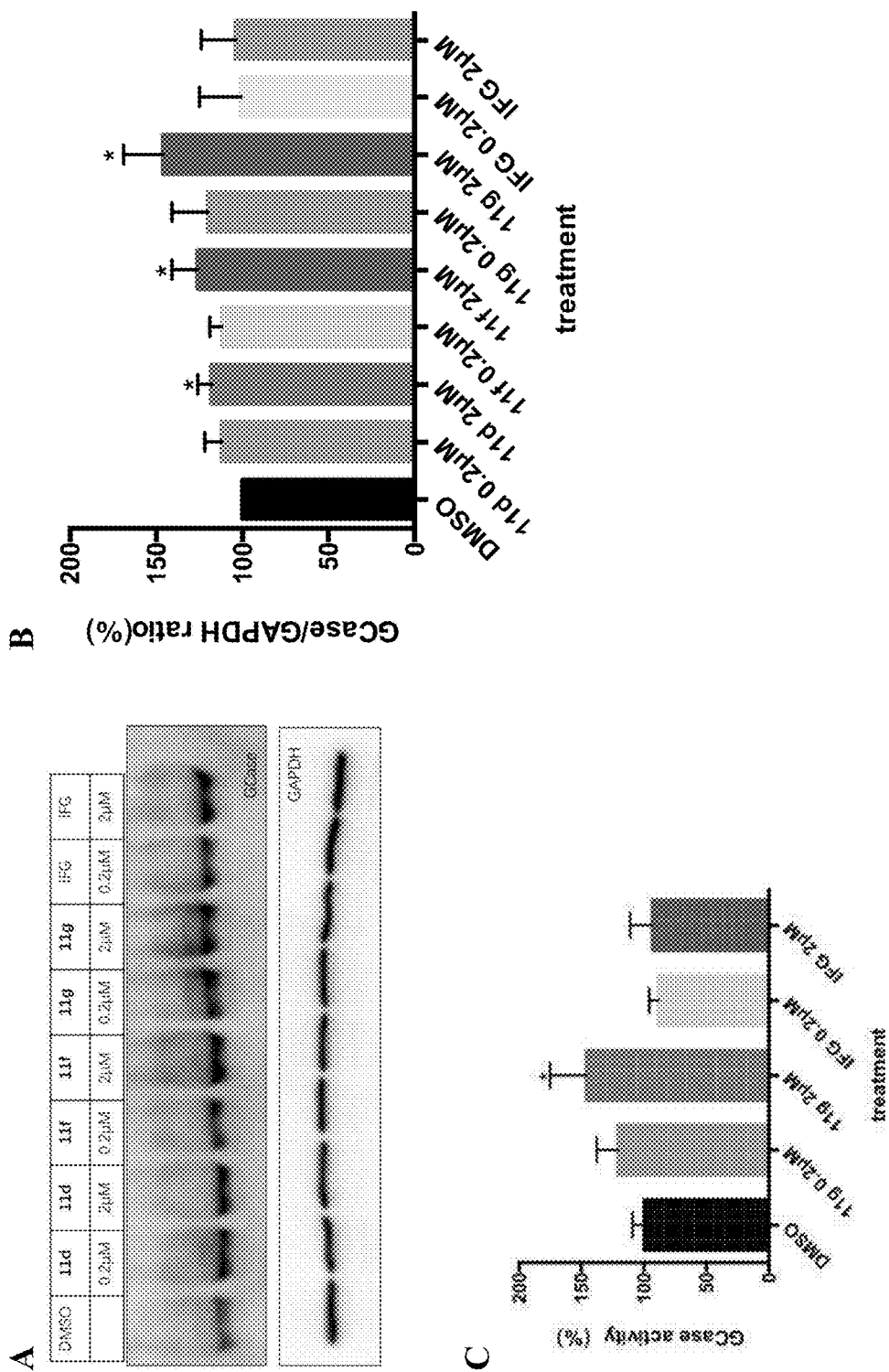
FIG. 6. Inhibitors of GCase increase GCase protein levels and activity in Gaucher's disease patient fibroblasts. (A) Western blot of N370S fibroblast treated with GCase inhibitors 11d, 11f, 11g or IFG for 3 days. (B) Statistical analysis for Western blot of N370S fibroblast after inhibitors and IFG treatment. We used the GAPDH signal to normalize the GCase signal, and a DMSO treated sample as control (100%). (C) GCase activity assay for N370S fibroblast after 11g and IFG 3-day treatment. N=3 independent experiments. One-tail T-test * means p<0.05.

Finally, we tested inhibitors 11d, 11f, and 11g in patient N370S fibroblasts. The fibroblasts were treated with the compounds for 3 days and levels of GCase protein determined by Western blot. We found 11d, 11f, and 11g significantly increased the concentration of GCase, while IFG at the same concentration did not have an effect (FIGS. 6A and 6B). Consistent with this finding, compound 11g increased GCase activity in patient cells whereas IFG had no effect (FIG. 6C), suggesting that 11g increased both GCase levels and activity in patient N370S fibroblasts.

Conclusions

In this paper, we describe the design and SAR of a series of quinazoline GCase inhibitors having single digit nanomolar potency. The SAR suggested that a hydrophobic interaction and a π-π interaction may be involved in compound binding to GCase. These quinazoline derivatives also stabilized GCase, as indicated by thermal shift assays, and exhibited high selectivity against other lysosomal hydrolases. Furthermore, the most potent compounds increased the GCase concentration and activity in patient N370S fibroblasts, while IFC did not. It will be of interest to further test these compounds in more biological assays and models of Gaucher's and Parkinson's disease.

Experimental Section

Materials and Methods

Chemistry

Commercially available reagents and solvents were used without further purification. Compounds were synthesized and analyzed as indicated in this example and the foregoing examples. All reactions were monitored by thin-layer chromatography (TLC) using 0.25 mm Silicycle extra hard 250 μM TLC plates (60 F254). Purification of reaction products was carried out by flash chromatography using an Agilent 971-FP flash purification system with Silicycle silica gel columns. The yields are not optimized. The purity of all compounds was over 95% as analyzed with an Agilent 1260 Infinity HPLC system and an Agilent Poroshell 120 EC-C18 (4.6×50 mm, 2.7 μm) reverse phase column, detecting with UV absorbance (254 nm). $^1$H NMR and $^{13}$C NMR spectra were obtained using a Bruker Avance III 500 MHz system (500 MHz for $^1$H NMR and 125 MHz for $^{13}$C NMR) spectrometer. Chemical shifts are reported relative to chloroform (δ=7.26 for $^1$H NMR and δ=77.16 for $^{13}$C NMR spectra) or dimethyl sulfoxide (δ=2.50 for $^1$H and δ=39.52 for $^{13}$C NMR spectra). Data are reported as br=broad, s=singlet, d=doublet, t=triplet, q=quartet, m=multiplet. Mass spectra were obtained using a Bruker AmaZon SL system. High resolution mass spectra (HRMS) were performed using an Agilent 6210A LC-TOF instrument with a dual spray ESI source, with a high resolution Time of Flight (TOF) Mass analyzer and collecting in a 2 GigHz detector mode, coupled with an Agilent 1200 HPLC. Analytical data are provided in this example and the foregoing examples.

Preparation of 4-chloro-2-(pyridin-3-yl)quinazoline (5)[25]

To a solution of 2-aminobenzonitrile (5.90 g, 50 mmol) in sulfolane (20 mL) was added nicotinoyl chloride hydrochloride (12.0 g, 67.4 mmol), and the mixture was stirred at 100° C. for 16 h. PCl$_5$ (18.2 g, 87.5 mmol) was added in one portion and stirred at 100° C. for 10 h. The mixture was cooled to room temperature, and carefully poured into 400 mL of saturated sodium bicarbonate solution cooling in an ice bath. The solid was filtered, washed with water, dried, and purified by flash chromatography to give 5 as a pale-yellow solid (5.50 g, 46%); mp 160-163° C. $^1$H NMR (400 MHz, CDCl$_3$) δ 9.76 (d, J=1.3 Hz, 1H), 8.82 (dt, J=8.0, 1.9 Hz, 1H), 8.73 (dd, J=4.7, 1.4 Hz, 1H), 8.26 (dd, J=8.4, 0.8 Hz, 1H), 8.10 (d, J=8.4 Hz, 1H), 7.95 (ddd, J=8.4, 7.0, 1.4 Hz, 1H), 7.69 (ddd, J=8.2, 7.0, 1.1 Hz, 1H), 7.44 (dd, J=7.5, 4.8 Hz, 1H). $^{13}$C NMR: (100 MHz, CDCl$_3$) δ 162.9, 158.3, 151.8, 151.7, 150.3, 136.1, 135.2, 132.4, 129.1, 128.9, 126.0, 123.5, 122.8. ESI-MS m/z: 242 (M+H)$^+$.

General Procedure for Compound 4, 6a-6i, 7a-7i, 8a-8g and 9a-9f

A mixture of 4-chloro-2-(pyridin-3-yl)quinazoline 5 (72 mg, 0.3 mmol), amine (0.3 mmol), and potassium carbonate (69 mg, 0.3 mmol) in DMF (3 mL) was stirred at room temperature or 60° C. overnight. Water (20 mL) was added, and the formed solid was filtered, washed with water, and dried in vacuo to give product. The products were usually pure (>95% purity). Those products without sufficient purity were purified by flash chromatography.

Preparation of 2-chloro-N-(2,3-dihydro-1H-inden-2-yl)quinazolin-4-amine (10)

A mixture of 2,4-dichloroquinazoline (398 mg, 2.0 mmol), 2,3-dihydro-1H-inden-2-amine (266 mg, 2.0 mmol), and potassium carbonate (276 mg, 2.0 mmol) in DMF (5 mL) was stirred at room temperature for 5 h. Water (20 mL) was added, and the formed solid was filtered, washed with water, and solid was dried to give 10 as an off-white solid (390 mg, 66%); mp 239-240° C.
$^1$H NMR (500 MHz, CDCl$_3$) δ 7.76 (d, J=8.2 Hz, 1H), 7.74-7.69 (m, 1H), 7.60 (d, J=8.2 Hz, 1H), 7.41 (t, J=7.4 Hz, 1H), 7.30-7.26 (m, 2H), 7.24-7.19 (m, 2H), 6.08 (d, J=6.7 Hz, 1H), 5.27-5.15 (m, 1H), 3.53 (dd, J=16.2, 7.0 Hz, 2H), 3.00 (dd, J=16.2, 4.0 Hz, 2H). $^{13}$C NMR (125 MHz, CDCl$_3$) δ 160.6, 157.8, 151.0, 140.7, 133.6, 128.0, 127.1, 126.2, 125.1, 120.8, 113.3, 52.6, 40.2. MS (ESI) m/z [M+H]+: calcd, 296.09. found, 296.13.

General Procedure for Synthesis of 11a-11h

A mixture of 2-chloro-N-(2,3-dihydro-1H-inden-2-yl)quinazolin-4-amine 10 (148 mg, 0.5 mmol), boronic acid (0.5 mmol), Pd(PPh$_3$)$_4$ (58 mg, 0.05 mmol), potassium carbonate (276 mg, 2.0 mmol) in dioxane (10 mL) and water (1.5 mL) was heated at 85° C. under an argon atmosphere for 16 h. Water (5 mL) was added, and the mixture was extracted with EtOAc (25 mL×3). The combined organic phase was washed with brine (15 mL), dried (Na$_2$SO$_4$), filtered, evaporated, and purified by flash chromatography to give product.

Analytical Data for Compounds 11a-11h

N-(2,3-dihydro-1H-inden-2-yl)-2-(4-methylpyridin-3-yl)quinazolin-4-amine (11a)

White solid (125 mg, 71%); mp 170-172° C. $^1$H NMR (500 MHz, CDCl$_3$) δ 9.16 (s, 1H), 8.50 (d, J=5.0 Hz, 1H), 7.91 (d, J=7.9 Hz, 1H), 7.75 (ddd, J=8.3, 7.0, 1.2 Hz, 1H), 7.67 (d, J=7.8 Hz, 1H), 7.49-7.42 (m, 1H), 7.29 (dd, J=5.3, 3.4 Hz, 2H), 7.25-7.19 (m, 3H), 5.94 (d, J=7.0 Hz, 1H), 5.26 (tdd, J=7.1, 4.4, 2.6 Hz, 1H), 3.54 (dd, J=16.2, 7.1 Hz, 2H), 3.04 (dd, J=16.2, 4.4 Hz, 2H), 2.72 (s, 3H). $^{13}$C NMR (125 MHz, CDCl$_3$) δ 161.1, 159.1, 151.3, 150.1, 149.2, 146.6, 140.9, 135.4, 132.7, 128.8, 126.8, 125.9, 124.9, 120.7, 113.2, 52.3, 40.2, 21.0. HRMS (ESI): calcd for C$_{23}$H$_{21}$N$_4$ [M+H]+, 353.1761. found, 353.1765.

N-(2,3-dihydro-1H-inden-2-yl)-2-(5-methylpyridin-3-yl)quinazolin-4-amine (11b)

Yellow solid (134 mg, 76%); mp 200-201° C. $^1$H NMR (500 MHz, CDCl$_3$) δ 9.59 (d, J=1.6 Hz, 1H), 8.63 (s, 1H), 8.53 (d, J=1.6 Hz, 1H), 7.92 (d, J=8.0 Hz, 1H), 7.77-7.71 (m, 1H), 7.66 (d, J=7.8 Hz, 1H), 7.45-7.38 (m, 1H), 7.30 (dd, J=5.3, 3.4 Hz, 2H), 7.23 (dd, J=5.5, 3.2 Hz, 2H), 5.95 (d, J=6.8 Hz, 1H), 5.40-5.29 (m, 1H), 3.61 (dd, J=16.2, 7.2 Hz, 2H), 3.08 (dd, J=16.2, 4.8 Hz, 2H), 2.45 (s, 3H). $^{13}$C NMR (125 MHz, CDCl$_3$) δ 159.3, 158.8, 151.2, 150.3, 147.6, 141.1, 136.0, 134.0, 132.7, 132.6, 128.7, 126.8, 125.7, 124.9, 120.8, 113.9, 52.4, 40.1, 18.5. HRMS (ESI): calcd for C$_{23}$H$_{21}$N$_4$ [M+H]+, 353.1761. found, 353.1757.

N-(2,3-dihydro-1H-inden-2-yl)-2-(6-methylpyridin-3-yl)quinazolin-4-amine (11c)

Yellow solid (129 mg, 73%); mp 175-176° C. $^1$H NMR (500 MHz, CDCl$_3$) δ 9.66 (d, J=1.9 Hz, 1H), 8.69 (dd, J=8.1, 2.2 Hz, 1H), 7.89 (d, J=8.0 Hz, 1H), 7.73-7.68 (m, 1H), 7.63 (d, J=7.9 Hz, 1H), 7.41-7.36 (m, 1H), 7.29-7.25 (m, 2H), 7.23-7.19 (m, 3H), 5.91 (d, J=6.6 Hz, 1H), 5.33-5.23 (m, 1H), 3.58 (dd, J=16.2, 7.2 Hz, 2H), 3.06 (dd, J=16.1, 4.8 Hz, 2H), 2.62 (s, 3H). $^{13}$C NMR (125 MHz, CDCl$_3$) δ 159.8, 159.2, 158.8, 150.4, 149.7, 141.0, 136.0, 132.6, 131.6, 128.8, 126.9, 125.6, 124.9, 122.7, 120.5, 113.7, 52.5, 40.2, 24.5. HRMS (ESI): calcd for C$_{23}$H$_{21}$N$_4$ [M+H]+, 353.1761. found, 353.1767.

N-(2,3-dihydro-1H-inden-2-yl)-2-phenylquinazolin-4-amine (11d)

White solid (84 mg, 50%); mp 221-223° C. $^1$H NMR (500 MHz, CDCl$_3$) δ 8.64-8.56 (m, 2H), 7.93 (d, J=8.3 Hz, 1H), 7.72 (ddd, J=8.3, 7.0, 1.3 Hz, 1H), 7.64 (d, J=7.8 Hz, 1H), 7.53-7.46 (m, 3H), 7.39 (ddd, J=8.1, 7.0, 1.1 Hz, 1H), 7.31 (dd, J=5.3, 3.3 Hz, 2H), 7.24 (dd, J=5.5, 3.2 Hz, 2H), 5.86 (d, J=6.6 Hz, 1H), 5.38 (tdd, J=7.1, 5.1, 2.1 Hz, 1H), 3.61 (dd, J=16.1, 7.2 Hz, 2H), 3.08 (dd, J=16.1, 5.0 Hz, 2H). $^{13}$C NMR (125 MHz, CDCl$_3$) δ 160.4, 159.2, 150.5, 141.1, 138.9, 132.5, 130.1, 128.9, 128.4, 128.2, 126.8, 125.3, 125.0, 120.4, 113.6, 52.4, 40.2. HRMS (ESI): calcd for C$_{23}$H$_{20}$N$_3$ [M+H]+, 338.1652. found, 338.1647.

N-(2,3-dihydro-1H-inden-2-yl)-2-(pyridin-4-yl)quinazolin-4-amine (11e)

Brown solid (59 mg, 35%); mp 246-247° C. $^1$H NMR (500 MHz, CDCl$_3$) δ 8.74 (d, J=5.5 Hz, 2H), 8.40 (d, J=5.9 Hz, 2H), 7.93 (d, J=8.2 Hz, 1H), 7.78-7.70 (m, 1H), 7.67 (d, J=8.1 Hz, 1H), 7.48-7.39 (m, 1H), 7.29 (dd, J=5.2, 3.4 Hz, 2H), 7.22 (dd, J=5.4, 3.3 Hz, 2H), 5.99 (d, J=6.7 Hz, 1H), 5.37-5.29 (m, 1H), 3.59 (dd, J=16.2, 7.2 Hz, 2H), 3.07 (dd, J=16.1, 4.8 Hz, 2H). $^{13}$C NMR (125 MHz, CDCl$_3$) δ 159.4, 158.4, 150.2, 150.2, 146.4, 141.0, 132.8, 129.2, 126.9, 126.3, 125.0, 122.3, 120.6, 114.1, 77.2, 77.0, 76.7, 52.5, 40.1. HRMS (ESI): calcd for C$_{22}$H$_{19}$N$_4$ [M+H]+, 339.1604. found, 339.1608.

N-(2,3-dihydro-1H-inden-2-yl)-2-(thiophen-2-yl)quinazolin-4-amine (11f)

Off-white solid (68 mg, 40%); mp 243-246° C. $^1$H NMR (500 MHz, CDCl$_3$) δ 8.08 (d, J=3.1 Hz, 1H), 7.85 (d, J=8.4 Hz, 1H), 7.69 (t, J=7.6 Hz, 1H), 7.61 (d, J=8.1 Hz, 1H), 7.45 (d, J=4.9 Hz, 1H), 7.38-7.33 (m, 1H), 7.32-7.27 (m, 2H), 7.23 (dd, J=5.3, 3.3 Hz, 2H), 7.18-7.13 (m, 1H), 5.88 (d, J=6.3 Hz, 1H), 5.31-5.24 (m, 1H), 3.60 (dd, J=16.2, 7.2 Hz, 2H), 3.06 (dd, J=16.2, 5.0 Hz, 2H). $^{13}$C NMR (125 MHz, CDCl$_3$) δ 159.0, 157.3, 150.4, 145.2, 141.1, 132.6, 129.0, 128.5, 128.2, 127.9, 126.8, 125.1, 124.9, 120.5, 113.5, 52.5, 40.1. HRMS (ESI): calcd for C$_{21}$H$_{18}$N$_3$S [M+H]+, 344.1216. found, 344.1218.

N-(2,3-dihydro-1H-inden-2-yl)-2-(thiophen-3-yl)quinazolin-4-amine (112)

Yellow solid (75 mg, 44%); mp 232-233° C. $^1$H NMR (500 MHz, CDCl$_3$) δ 8.34 (d, J=3.0 Hz, 1H), 8.02 (dd, J=5.0, 0.9 Hz, 1H), 7.87 (d, J=8.3 Hz, 1H), 7.74-7.65 (m, 1H), 7.62 (d, J=8.0 Hz, 1H), 7.42-7.34 (m, 2H), 7.30 (dd, J=5.2, 3.4 Hz, 2H), 7.25-7.21 (m, 2H), 5.85 (d, J=6.5 Hz, 1H), 5.36-5.25 (m, 1H), 3.58 (dd, J=16.2, 7.2 Hz, 2H), 3.07 (dd, J=16.1, 5.0 Hz, 2H). $^{13}$C NMR (125 MHz, CDCl$_3$) δ 159.1, 157.8, 150.5, 143.1, 141.1, 132.5, 128.6, 127.9, 127.4, 126.8, 125.4, 125.1, 124.9, 120.5, 113.5, 52.3, 40.2. HRMS (ESI): calcd for $C_{21}H_{18}N_3S$ [M+H]$^+$, 344.1216. found, 344.1215.

N-(2,3-dihydro-1H-inden-2-yl)-2-(furan-2-yl)quinazolin-4-amine (11h)

Pale-yellow solid (80 mg, 49%); mp 231-232° C. $^1$H NMR (500 MHz, CDCl$_3$) δ 7.96 (d, J=8.4 Hz, 1H), 7.73-7.67 (m, 1H), 7.67-7.61 (m, 2H), 7.41-7.32 (m, 2H), 7.32-7.26 (m, 2H), 7.25-7.21 (m, 2H), 6.57 (dd, J=3.3, 1.7 Hz, 1H), 5.98 (d, J=6.8 Hz, 1H), 5.34-5.20 (m, 1H), 3.57 (dd, J=16.1, 7.2 Hz, 2H), 3.05 (dd, J=16.1, 5.0 Hz, 2H). $^{13}$C NMR (125 MHz, CDCl$_3$) δ 159.1, 153.7, 153.4, 150.1, 144.6, 141.0, 132.7, 128.8, 126.8, 125.3, 124.9, 120.5, 113.7, 113.1, 111.8, 52.3, 40.1. HRMS (ESI): calcd for $C_{21}H_{18}N_3O$ [M+H]$^+$, 328.1444. found, 328.1448.

Enzymatic Assays

4-Methylumbelliferyl β-D-glucopyranoside (4MU-β-Glc), 4-methylumbelliferyl α-D-glucopyranoside, 4-methylumbelliferyl α-D-galactopyranoside, and buffer components were purchased from Sigma-Aldrich (St. Louis, Mo.). The recombinant wild-type GCase enzyme velaglucerase alfa (Vpriv®, Shire Human Genetic Therapies, Inc.), acid α-glucosidase enzyme alglucosidase alfa (Lumizyme®, Genzyme Corporation), α-galactosidase A enzyme agalsidase beta (Fabrazyme®, Genzyme Corporation) were used in activity assays. The GCase activity assay buffer was composed of 50 mM citric acid, 176 mM K$_2$HPO$_4$, and 0.01% Tween-20 at pH5.0, pH 5.9 and pH7.0. A solution of 1 M sodium hydroxide and 1 M glycine (pH 10) was used as the stop solution for all three enzyme activity assays.

GCase Enzyme Activity Assay.

The compounds in DMSO solution (0.5 μL/well) were transferred to a black 96-well plate (the final titration started from 100 μM, a 12 or 24-point 2-fold dilution series). Enzyme solution (33.5 μL, 7.5 nM final concentration, in pH 5.9 buffer) was transferred to the wells. After 5 min of incubation at room temperature, the enzyme reaction was initiated by the addition of blue substrate (4MU-13-Glc) (33 μL/well). The final concentration of the blue substrate was 1.5 mM. The blue substrate reaction was terminated by the addition of 33 μL/well stop solution (1 M NaOH and 1 M glycine mixture, pH 10) after 30 min of incubation at 37° C. The fluorescence was then measured in a Biotek Synergy H1 multi-mode plate reader with Ex=365 nm and Em=440 nm. The selected compounds were further assayed under pH 5.0 and pH 7.0 to evaluate their selectivity under various pH conditions.

Enzyme Kinetic Assay.

The substrate resorufin β-D-glucopyranoside was diluted to five concentrations, ranging from 30 to 150 μM. Seven concentrations of inhibitors (between 0.5- and 5-fold of IC$_{50}$ value) and a DMSO control were added to the enzyme solution. The final enzyme concentration was 10 nM to give a linear reaction over 10 min. Enzyme kinetics were measured by the addition of 66 μL of substrate to a 96-well assay plate, followed by 33 μL of enzyme solution (with or without inhibitor) using a dispense module on a Biotek Synergy H1 multi-mode plate reader. The increase in product fluorescence was measured at 1 min intervals for 10 min in the plate reader. The rate of product formation was calculated by converting the fluorescence units to nanomoles of product per minute using a standard curve of the free fluorophore, resorufin.

Enzyme Selectivity Assays.

The acid α-glucosidase and α-galactosidase A enzyme activity assay methods were similar to the GCase enzyme activity assay above with slight modifications. The buffer for the two enzyme assays consisted of 50 mM citric acid, 176 mM K$_2$HPO$_4$, and 0.01% Tween-20 at pH 4.8. The final enzyme concentrations for acid α-glucosidase and α-galactosidase A were 8 and 1 nM, respectively. The substrate concentrations for these related enzymes were at 0.16 and 0.4 mM, respectively.

Fluorescence Thermal Shift Analysis[31].

A robotic pipeline in the High Throughput Analysis Laboratory (HTAL) was used for protein ligand screening by fluorescence thermal shift (FTS) analysis. The pipeline used a Mosquito robot (TTP Labtech) for protein dispensing and an Echo 550 (Labcyte) to add compounds. Thermal scanning coupled with fluorescence detection was performed on a real-time PCR machine CFX384 (Bio-Rad Laboratories). The assay was run in 384-well PCR plates, using 10 μL citric acid/K$_2$HPO$_4$ buffer (50 mM citric acid, 150 mM K$_2$HPO$_4$, pH 5.0) per well. The assay concentration for protein was 1 μM and that for Sypro Orange (Invitrogen) was 5×. Protein was premixed with Sypro Orange and dispensed to a plate first, and compounds were added. Final concentrations of compounds ranged from 0.5 to 200 μM. Then the plate was sealed with an optical seal, shaken, and centrifuged. The thermal scan was from 10 to 95° C. with a temperature ramp rate of 1.5° C./min. The fluorescence was recorded every 10 sec. Data analysis and report generation were performed using the in-house software excelFTS. The $T_m$ of wild-type GCase was found to follow a logarithmic dose-dependent trend when denaturation was performed in the presence of isofagomine or selected compounds.

N370S Cell Culture and Compound Treatment.

The N370S fibroblast cell line was obtained from Coriell, GM00372, cultured in DMEM medium (Life Tech) including 1% v/v L-glutamine 200 mM (Life Tech), 1% v/v pen strep (Life Tech), 10% FBS (Life Tech) at 37° C. and 5% CO$_2$ and treated with different compounds at 0.2 μM and 2 μM. After a 3-day treatment, cells were washed with inhibitor free media 3 times and fed with inhibitor free media for 1 day, followed by 1% Triton X-100 lysis buffer to lyse cells. Protein concentrations were measured with a Bradford kit (Thermo), and the GCase activity was determined at pH 5.5.

Western Blot.

Proteins were denatured in 20% SDS sample buffer at 100° C. for 10 min; 10% Bis-Tris gel (Life Tech) was used for gels; Trans-Blot Turbo PVDF kit (Bio-Rad) was used for membrane transfer, and Chemidoc MP system (Bio-Rad) was used to analyze the blots.

REFERENCES (1) Grabowski, G. A. Phenotype, diagnosis, and treatment of Gaucher's disease. Lancet 2008, 372, 1263-1271.
(2) Bennett, L. L.; Mohan, D. Gaucher disease and its treatment options. Ann. Pharmacother. 2013, 47, 1182-1193.
(3) Grabowski, G. A.; Zimran, A.; Ida, H. Gaucher disease types 1 and 3: Phenotypic characterization of large populations from the ICGG Gaucher Registry. Am. J. Hematol. 2015, 90 Suppl 1, S12-18.

(4) Hruska, K. S.; LaMarca, M. E.; Scott, C. R.; Sidransky, E. Gaucher disease: mutation and polymorphism spectrum in the glucocerebrosidase gene (GBA). Hum. Mutat. 2008, 29, 567-583.

(5) Sawkar, A. R.; Cheng, W. C.; Beutler, E.; Wong, C. H.; Balch, W. E.; Kelly, J. W. Chemical chaperones increase the cellular activity of N370S beta-glucosidase: a therapeutic strategy for Gaucher disease. Proc. Natl. Acad. Sci. U.S.A. 2002, 99, 15428-15433.

(6) Tekoah, Y.; Tzaban, S.; Kizhner, T.; Hainrichson, M.; Gantman, A.; Golembo, M.; Aviezer, D.; Shaaltiel, Y. Glycosylation and functionality of recombinant beta-glucocerebrosidase from various production systems. Biosci. Rep. 2013, 33, 771-U272.

(7) Aharon-Peretz, J.; Rosenbaum, H.; Gershoni-Baruch, R. Mutations in the glucocerebrosidase gene and Parkinson's disease in Ashkenazi Jews. N. Engl. J. Med. 2004, 351, 1972-1977.

(8) Sidransky, E.; Nalls, M. A.; Aasly, J. O.; Aharon-Peretz, J.; Annesi, G.; Barbosa, E. R.; Bar-Shira, A.; Berg, D.; Bras, J.; Brice, A.; Chen, C. M.; Clark, L. N.; Condroyer, C.; De Marco, E. V.; Dun, A.; Eblan, M. J.; Fahn, S.; Farrer, M. J.; Fung, H. C.; Gan-Or, Z.; Gasser, T.; Gershoni-Baruch, R.; Giladi, N.; Griffith, A.; Gurevich, T.; Januario, C. Kropp, P.; Lang, A. E.; Lee-Chen, G. J.; Lesage, S.; Marder, K.; Mata, I. F.; Mirelman, A. Mitsui, J.; Mizuta, I.; Nicoletti, G.; Oliveira, C.; Oilman, R.; Orr-Urtreger, A.; Pereira, L. V. Quattrone, A.; Rogaeva, E.; Rolfs, A.; Rosenbaum, H.; Rozenberg, R.; Samii, A.; Samaddar, T. Schulte, C.; Sharma, M.; Singleton, A.; Spitz, M.; Tan, E. K.; Tayebi, N.; Toda, T.; Troiano, A. R.; Tsuji, S.; Wittstock, M.; Wolfsberg, T. G.; Wu, Y. R.; Zabetian, C. P.; Zhao, Y.; Ziegler, S. G. Multicenter analysis of glucocerebrosidase mutations in Parkinson's disease. N. Engl. J. Med. 2009, 361, 1651-1661.

(9) Schapira, A. H. V.; Olanow, C. W.; Greenamyre, J. T.; Bezard, E. Slowing of neurodegeneration in Parkinson's disease and Huntington's disease: future therapeutic perspectives. Lancet 2014, 384, 545-555.

(10) Sidransky, E.; Lopez, G. The link between the GBA gene and parkinsonism. Lancet Neurol. 2012, 11, 986-998.

(11) Lin, M. K.; Farrer, M. J. Genetics and genomics of Parkinson's disease. Genome Med. 2014, 6, 48.

(12) Mazzulli, J. R.; Xu, Y. H.; Sun, Y.; Knight, A. L.; McLean, P. J.; Caldwell, G. A.; Sidransky, E.; Grabowski, G. A.; Krainc, D. Gaucher disease glucocerebrosidase and alpha-synuclein form a bidirectional pathogenic loop in synucleinopathies. Cell 2011, 146, 37-52.

(13) Sardi, S. P.; Clarke, J.; Viel, C.; Chan, M.; Tamsett, T. J.; Treleaven, C. M.; Bu, J.; Sweet, L.; Passini, M. A.; Dodge, J. C.; Yu, W. H.; Sidman, R. L.; Cheng, S. H.; Shihabuddin, L. S. Augmenting CNS glucocerebrosidase activity as a therapeutic strategy for parkinsonism and other Gaucher-related synucleinopathies. Proc. Natl. Acad. Sci. U.S.A. 2013, 110, 3537-3542.

(14) Sybertz, E.; Krainc, D. Development of targeted therapies for Parkinson's disease and related synucleinopathies. J. Lipid Res. 2014, 55, 1996-2003.

(15) Wang, G. N.; Reinkensmeier, G.; Zhang, S. W.; Thou, J.; Zhang, L. R.; Zhang, L. H.; Butters, T. D.; Ye, X. S. Rational design and synthesis of highly potent pharmacological chaperones for treatment of N370S mutant Gaucher disease. J. Med. Chem. 2009, 52, 3146-3149.

(16) Trapero, A.; Gonzalez-Bulnes, P.; Butters, T. D.; Llebaria, A. Potent aminocyclitol glucocerebrosidase inhibitors are subnanomolar pharmacological chaperones for treating gaucher disease. J. Med. Chem. 2012, 55, 4479-4488.

(17) Sawkar, A. R.; Schmitz, M.; Zimmer, K. P.; Reczek, D.; Edmunds, T.; Balch, W. E.; Kelly, J. W. Chemical chaperones and permissive temperatures alter localization of Gaucher disease associated glucocerebrosidase variants. ACS Chem. Biol. 2006, 1, 235-251.

(18) Steet, R. A.; Chung, S.; Wustman, B.; Powe, A.; Do, H.; Kornfeld, S. A. The iminosugar isofagomine increases the activity of N370S mutant acid beta-glucosidase in Gaucher fibroblasts by several mechanisms. Proc. Natl. Acad. Sci. U.S.A. 2006, 103, 13813-13818.

(19) Butters, T. D.; Dwek, R. A.; Platt, F. M Imino sugar inhibitors for treating the lysosomal glycosphingolipidoses. Glycobiology 2005, 15, 43R-52R.

(20) Zheng, W.; Padia, J; Urban, D. J.; Jadhav, A.; Goker-Alpan, O.; Simeonov, A.; Goldin, E.; Auld, D.; LaMarca, M. E.; Inglese, J.; Austin, C. P.; Sidransky, E. Three classes of glucocerebrosidase inhibitors identified by quantitative high-throughput screening are chaperone leads for Gaucher disease. Proc. Natl. Acad. Sci. U.S.A. 2007, 104, 13192-13197.

(21) Marugan, J. J.; Zheng, W.; Motabar, O.; Southall, N.; Goldin, E.; Westbroek, W.; Stubblefield, B. K.; Sidransky, E.; Aungst, R. A.; Lea, W. A.; Simeonov, A.; Leister, W.; Austin, C. P. Evaluation of quinazoline analogues as glucocerebrosidase inhibitors with chaperone activity. J. Med. Chem. 2011, 54, 1033-1058.

(22) Marugan, J. J.; Huang, W.; Motabar, O.; Zheng, W.; Xiao, J.; Patnaik, S.; Southall, N.; Westbroek, W.; Lea, W. A.; Simeonov, A.; Goldin, E.; Debernardi, M. A.; Sidransky, E. Non-iminosugar glucocerebrosidase small molecule chaperones. Medchemcomm. 2012, 3, 56-60.

(23) Tropak, M. B.; Kornhaber, G. J.; Rigat, B. A.; Maegawa, G. H.; Buttner, J. D.; Blanchard, J. E.; Murphy, C.; Tuske, S. J.; Coales, S. J.; Hamuro, Y.; Brown, E. D.; Mahuran, D. J. Identification of pharmacological chaperones for Gaucher disease and characterization of their effects on beta-glucocerebrosidase by hydrogen/deuterium exchange mass spectrometry. Chembiochem 2008, 9, 2650-2662.

(24) Huang, W.; Zheng, W.; Urban, D. J.; Inglese, J.; Sidransky, E.; Austin, C. P.; Thomas, C. J. N4-phenyl modifications of N2-(2-hydroxyl)ethyl-6-(pyrrolidin-1-yl)-1,3,5-triazine-2,4-diamines enhance glucocerebrosidase inhibition by small molecules with potential as chemical chaperones for Gaucher disease. Bioorg. Med. Chem. Lett. 2007, 17, 5783-5789.

(25) Storz, T.; Heid, R.; Zeldis, J.; Hoagland, S. M.; Rapisardi, V.; Hollywood, S.; Morton, G. Convenient and Practical One-Pot Synthesis of 4-Chloropyrimidines via a Novel Chloroimidate Annulation. Org. Process Res. Dev. 2011, 15, 918-924.

(26) Urban, D. J.; Zheng, W.; Goker-Alpan, O.; Jadhav, A.; Lamarca, M. E.; Inglese, J.; Sidransky, E.; Austin, C. P. Optimization and validation of two miniaturized glucocerebrosidase enzyme assays for high throughput screening. Comb. Chem. High Throughput Screen. 2008, 11, 817-824.

(27) Aguilar-Moncayo, M.; Garcia-Moreno, M. I.; Trapero, A.; Egido-Gabas, M.; Llebaria, A.; Fernandez, J. M. G.; Mellet, C. O. Bicyclic (galacto)nojirimycin analogues as glycosidase inhibitors: Effect of structural modifications in their pharmacological chaperone potential towards beta-glucocerebrosidase. Org. Biomol. Chem. 2011, 9, 3698-3713.

(28) Trapero, A.; Alfonso, I.; Butters, T. D.; Llebaria, A. Polyhydroxylated bicyclic isoureas and guanidines are potent glucocerebrosidase inhibitors and nanomolar enzyme activity enhancers in Gaucher cells. J. Am. Chem. Soc. 2011, 133, 5474-5484.
(29) Berger, Z.; Perkins, S.; Ambroise, C.; Oborski, C.; Calabrese, M.; Noell, S.; Riddell, D.; Hirst, W. D. Tool compounds robustly increase turnover of an artificial substrate by glucocerebrosidase in human brain lysates. PLoS One 2015, 10, e0119141.
(30) Lo, M. C.; Aulabaugh, A.; Jin, G.; Cowling, R.; Bard, J.; Malamas, M.; Ellestad, G. Evaluation of fluorescence-based thermal shift assays for hit identification in drug discovery. Anal. Biochem. 2004, 332, 153-159.
(31) Filippova, E. V.; Luan, C. H.; Dunne, S. F.; Kiryukhina, O.; Minasov, G.; Shuvalova, L.; Anderson, W. F. Structural characterization of a hypothetical protein: a potential agent involved in trimethylamine metabolism in Catenulispora acidiphila. J. Struct. Funct. Genomics 2014, 15, 33-40.

Example 8—Synthesis and Testing of Additional Substituted Quinazoline Compounds

Additional substituted quinazoline compounds were prepared and tested according to the procedures provided in the examples above. Results are shown in the following table.

Table of Additional Substituted Quinazoline Compounds.

| No. | Structure | MW | Activity $AC_{50}$ or $IC_{50}$ (μM unless nM indicated) |
| --- | --- | --- | --- |
| 90 | 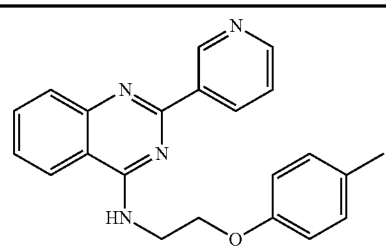 | 356 | 0.62 weak activator |
| 91 | 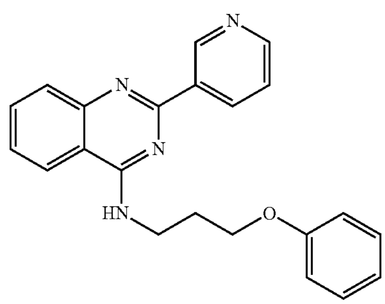 [SMILES: c1ccc(OCCCNc2nc(-c3cccnc3)nc3ccccc23)cc1] | 356 | 2.82 inhibitor |
| 92 | 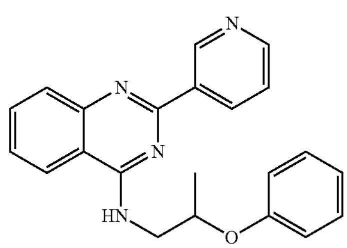 | 356 | 5.01 partial inhibitor |
| 93 | 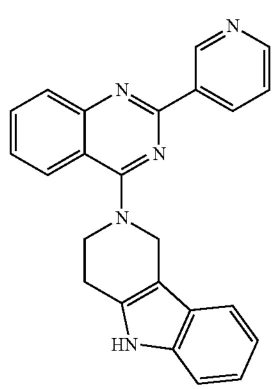 [SMILES: c1cncc(-c2nc(N3CCc4[nH]c5ccccc5c4C3)c3ccccc3n2)c1] | 377 | 6.31 activator |

-continued

Table of Additional Substituted Quinazoline Compounds.

| No. | Structure | MW | Activity AC$_{50}$ or IC$_{50}$ (μM unless nM indicated) |
|---|---|---|---|
| 94 | 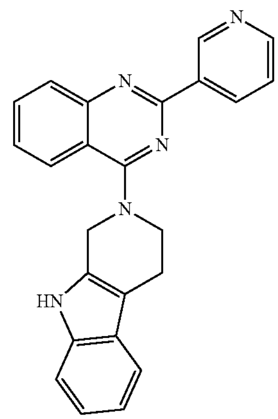 [SMILES: c1cncc(-c2nc(N3CCc4c([nH]c5ccccc45)C3)c3ccccc3n2)c1] | 377 | 2.82 activator |
| 95 | 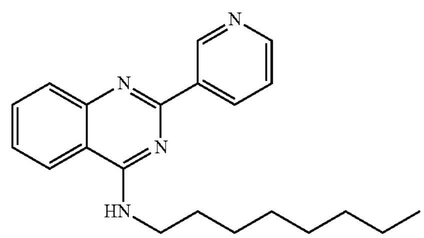 [SMILES: CCCCCCCCNc1nc(-c2cccnc2)nc2ccccc12] | 334 | 2.24 partial inhibitor |
| 96 | 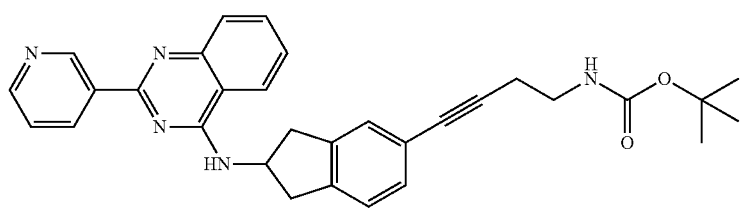 [SMILES: CC(C)(C)OC(=O)NCCC#Cc1ccc2c(c1)CC(Nc1nc(-c3cccnc3)nc3ccccc13)C2] | 505 | 0.56 inhibitor |
| 97 | 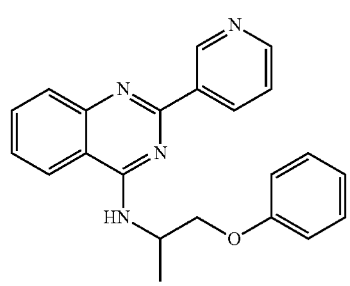 [SMILES: CC(COc1ccccc1)Nc1nc(-c2cccnc2)nc2ccccc12] | 356 | 2.51 inhibitor |
| 98 | 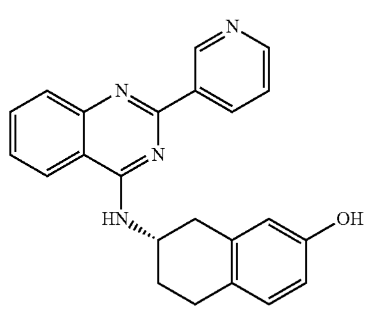 [SMILES: Oc1ccc2c(c1)C[C@@H](Nc1nc(-c3cccnc3)nc3ccccc13)CC2] | 368 | 0.079 inhibitor |

-continued

Table of Additional Substituted Quinazoline Compounds.

| No. | Structure | MW | Activity AC$_{50}$ or IC$_{50}$ (μM unless nM indicated) |
|---|---|---|---|
| 99 | 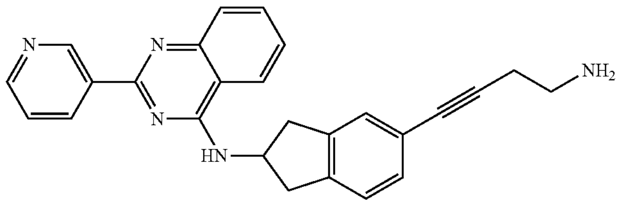 [SMILES: NCCC#Cc1ccc2c(c1)CC(Nc1nc(-c3cccnc3)nc3ccccc13)C2] | 405 | 0.891 inhibitor |
| 100 | 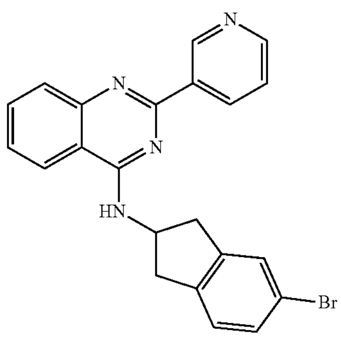 [SMILES: Brc1ccc2c(c1)CC(Nc1nc(-c3cccnc3)nc3ccccc13)C2] | 416 | 0.178 inhibitor |
| 101 | 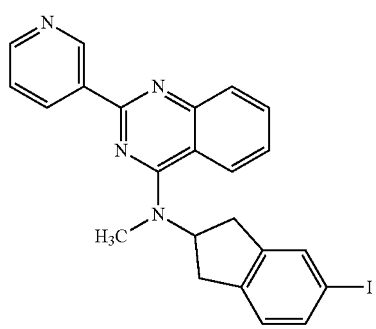 [SMILES: CN(c1nc(-c2cccnc2)nc2ccccc12)C1Cc2ccc(I)cc2C1] | 478 | NA |
| 102 | 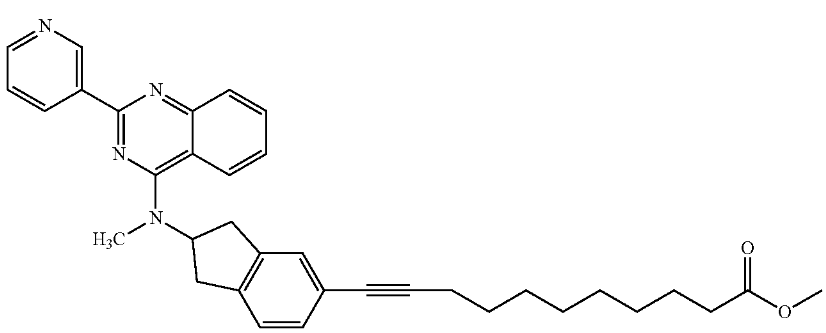 [SMILES: COC(=O)CCCCCCCCC#Cc1ccc2c(c1)CC(N(C)c1nc(-c3cccnc3)nc3ccccc13)C2] | 546 | NA |

-continued

Table of Additional Substituted Quinazoline Compounds.

| No. | Structure | MW | Activity AC$_{50}$ or IC$_{50}$ (μM unless nM indicated) |
|---|---|---|---|
| 103 | 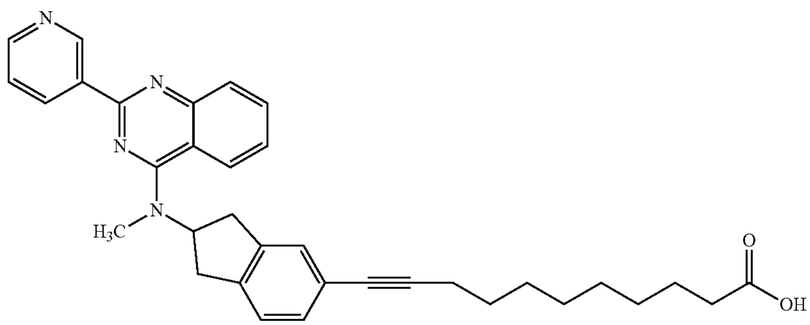 [SMILES: CN(c1nc(-c2cccnc2)nc2ccccc12)C1Cc2ccc(C#CCCCCCCCCC(=O)O)cc2C1] | 532 | NA |
| 104 | 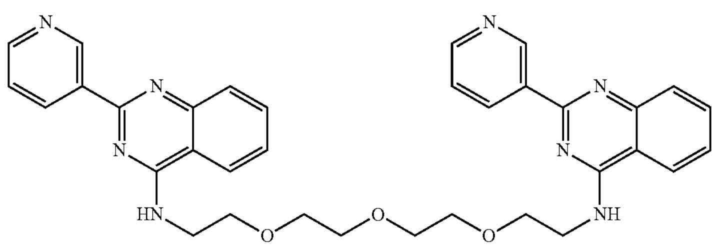 [SMILES: c1cncc(-c2nc(NCCOCCOCCOCCNc3nc(-c4cccnc4)nc4ccccc34)c3ccccc3n2)c1] | 602 | NA |
| 105 | 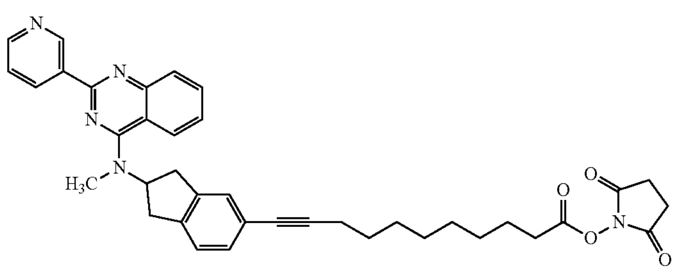 [SMILES: CN(c1nc(-c2cccnc2)nc2ccccc12)C1Cc2ccc(C#CCCCCCCCCC(=O)ON3C(=O)CCC3=O)cc2C1] | 629 | Weak activator |
| 106 | 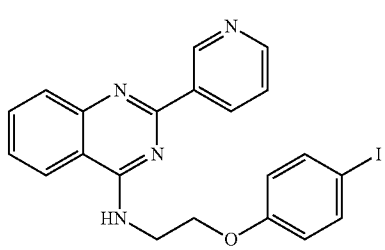 [SMILES: Ic1ccc(OCCNc2nc(-c3cccnc3)nc3ccccc23)cc1] | 468 | NA |
| 107 | 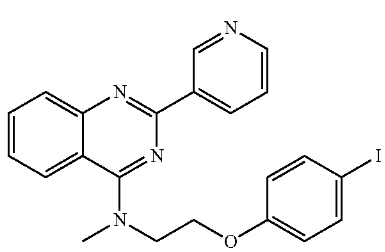 [SMILES: CN(CCOc1ccc(I)cc1)c1nc(-c2cccnc2)nc2ccccc12] | 482 | 6.25 |

-continued

Table of Additional Substituted Quinazoline Compounds.

| No. | Structure | MW | Activity AC$_{50}$ or IC$_{50}$ (µM unless nM indicated) |
|---|---|---|---|
| 108 | 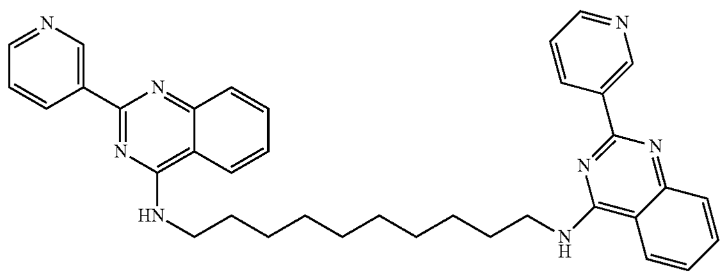 [SMILES: c1cncc(-c2nc(NCCCCCCCCCCNc3nc(-c4cccnc4)nc4ccccc34)c3ccccc3n2)c1] | 582 | 0.141 inhibitor |
| 109 | 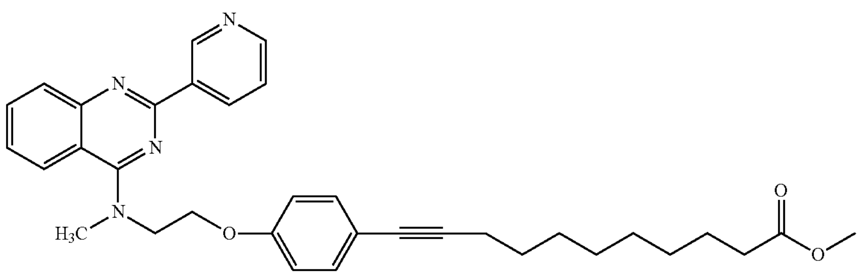 [SMILES: COC(=O)CCCCCCCCC#Cc1ccc(OCCN(C)c2nc(-c3cccnc3)nc3ccccc23)cc1] | 550 | Weak activator |
| 110 | 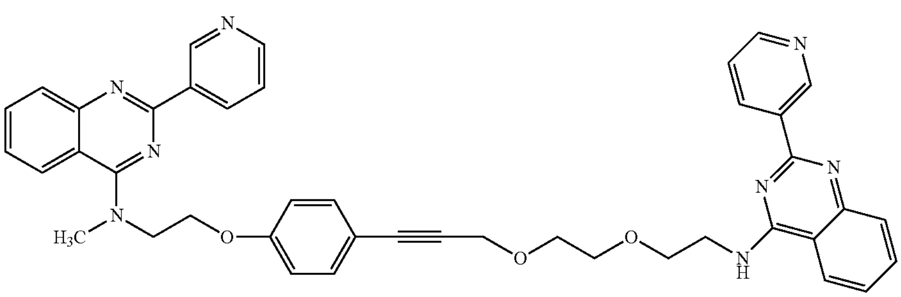 [SMILES: CN(CCOc1ccc(C#CCOCCOCCNc2nc(-c3cccnc3)nc3ccccc23)cc1)c1nc(-c2cccnc2)nc2ccccc12] | 702 | Weak activator |
| 111 | 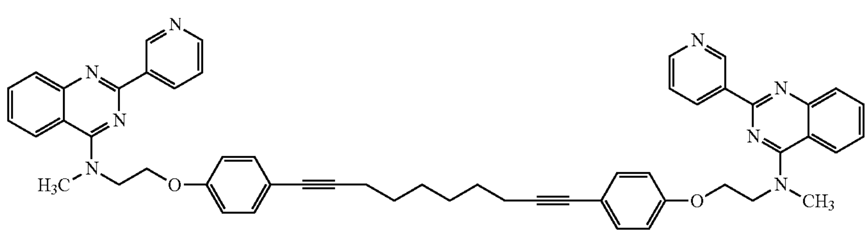 [SMILES: CN(CCOc1ccc(C#CCCCCCCC#Cc2ccc(OCCN(C)c3nc(-c4cccnc4)nc4ccccc34)cc2)cc1)c1nc(-c2cccnc2)nc2ccccc12] | 842 | 35 activator |
| 112 | 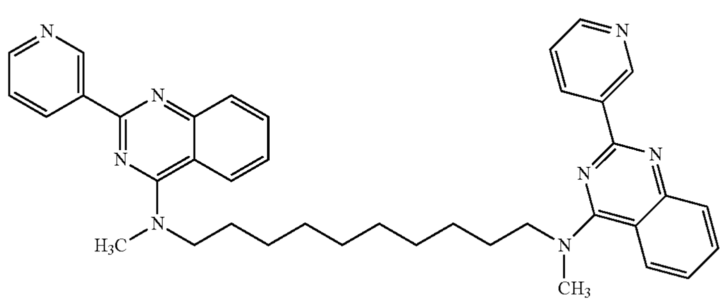 [SMILES: CN(CCCCCCCCCCN(C)c1nc(-c2cccnc2)nc2ccccc12)c1nc(-c2cccnc2)nc2ccccc12] | 610 | Weak activator |

-continued

Table of Additional Substituted Quinazoline Compounds.

| No. | Structure | MW | Activity $AC_{50}$ or $IC_{50}$ (μM unless nM indicated) |
|---|---|---|---|
| 113 | 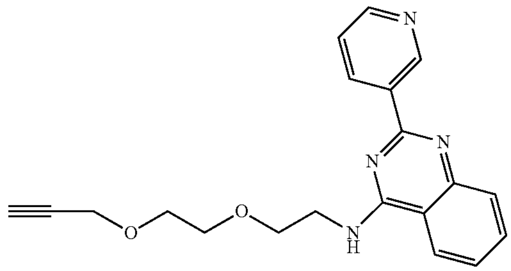 [SMILES: C#CCOCCOCCNc1nc(-c2cccnc2)nc2ccccc12] | 348 | 12.58 activator |
| 114 | 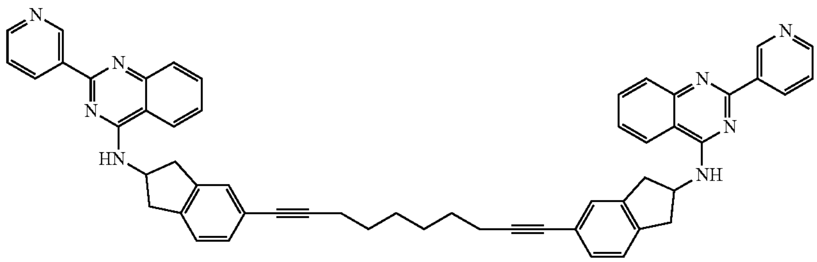 [SMILES: C(#Cc1ccc2c(c1)CC(Nc1nc(-c3cccnc3)nc3ccccc13)C2)CCCCCCC#Cc1ccc2c(c1)CC(Nc1nc(-c3cccnc3)nc3ccccc13)C2] | 806 | NA |
| 115 | 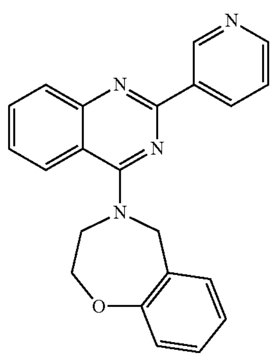 [SMILES: c1cncc(-c2nc(N3CCOc4ccccc4C3)c3ccccc3n2)c1] | 354 | 7.94 activator |
| 116 | 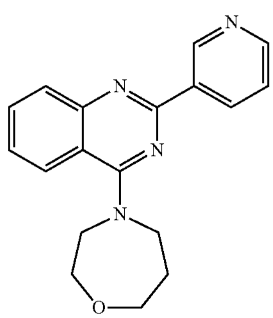 [SMILES: c1cncc(-c2nc(N3CCCOCC3)c3ccccc3n2)c1] | 306 | Weak activator |
| 117 | 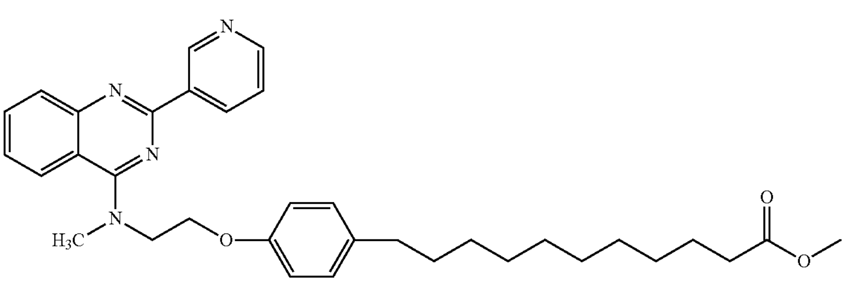 [SMILES: COC(=O)CCCCCCCCCCc1ccc(OCCN(C)c2nc(-c3cccnc3)nc3ccccc23)cc1] | 554 | 7.08 activator |

-continued

Table of Additional Substituted Quinazoline Compounds.

| No. | Structure | MW | Activity AC$_{50}$ or IC$_{50}$ (μM unless nM indicated) |
|---|---|---|---|
| 118 | 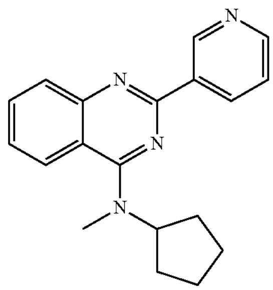 [SMILES: CN(c1nc(-c2cccnc2)nc2ccccc12)C1CCCC1] | 304 | 22.38 activator |
| 119 | 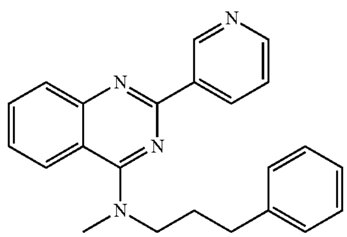 [SMILES: CN(CCCc1ccccc1)c1nc(-c2cccnc2)nc2ccccc12] | 354 | 5.01 activator |
| 120 | 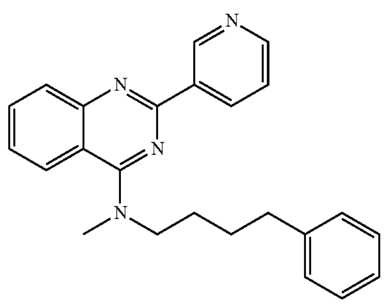 | 368 | 3.16 activator |
| 121 | 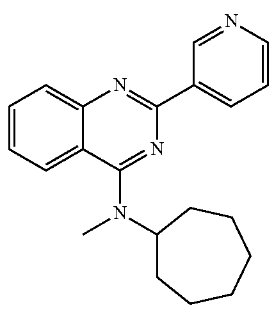 [SMILES: CN(c1nc(-c2cccnc2)nc2ccccc12)C1CCCCCC1] | 332 | 8.91 activator |
| 122 | 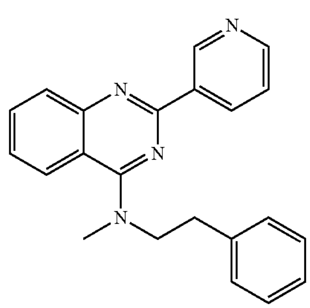 [SMILES: CN(CCc1ccccc1)c1nc(-c2cccnc2)nc2ccccc12] | 340 | 5.01 activator |

-continued

Table of Additional Substituted Quinazoline Compounds.

| No. | Structure | MW | Activity AC$_{50}$ or IC$_{50}$ (μM unless nM indicated) |
|---|---|---|---|
| 123 | 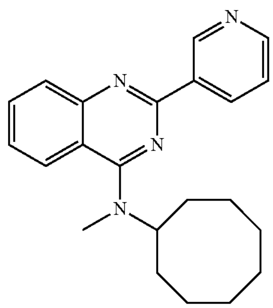 [SMILES: CN(c1nc(-c2cccnc2)nc2ccccc12)C1CCCCCCC1] | 346 | Weak activator |
| 124 | 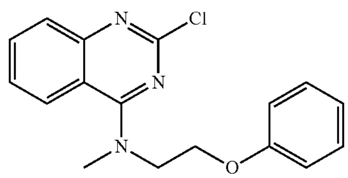 [SMILES: CN(CCOc1ccccc1)c1nc(Cl)nc2ccccc12] | 314 | 10 activator |
| 125 | 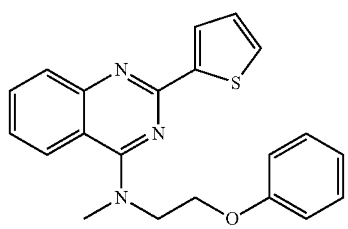 [SMILES: CN(CCOc1ccccc1)c1nc(-c2cccs2)nc2ccccc12] | 361 | Inactive |
| 126 | 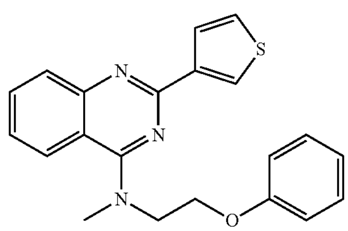 [SMILES: CN(CCOc1ccccc1)c1nc(-c2ccsc2)nc2ccccc12] | 361 | Inactive |
| 127 | 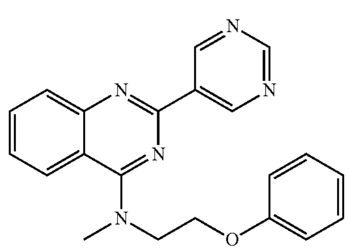 [SMILES: CN(CCOc1ccccc1)c1nc(-c2cncnc2)nc2ccccc12] | 357 | 1.25 activator |
| 128 | 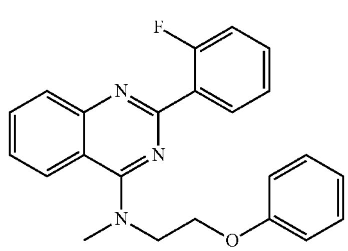 [SMILES: CN(CCOc1ccccc1)c1nc(-c2ccccc2F)nc2ccccc12] | 373 | 1.25 activator |

-continued

Table of Additional Substituted Quinazoline Compounds.

| No. | Structure | MW | Activity AC$_{50}$ or IC$_{50}$ (μM unless nM indicated) |
|---|---|---|---|
| 129 | 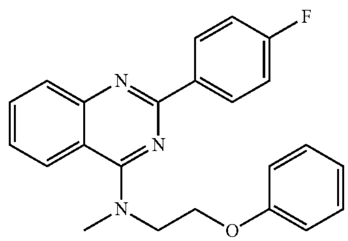 [SMILES: CN(CCOc1ccccc1)c1nc(-c2ccc(F)cc2)nc2ccccc12] | 373 | Inactive |
| 130 | 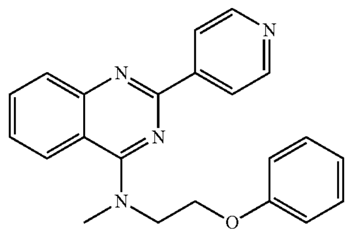 [SMILES: CN(CCOc1ccccc1)c1nc(-c2ccncc2)nc2ccccc12] | 356 | 3.98 activator |
| 131 | 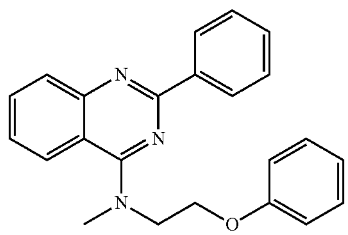 [SMILES: CN(CCOc1ccccc1)c1nc(-c2ccccc2)nc2ccccc12] | 355 | Inactive |
| 132 | 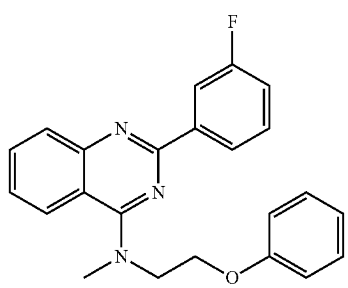 [SMILES: CN(CCOc1ccccc1)c1nc(-c2cccc(F)c2)nc2ccccc12] | 373 | Inactive |
| 133 | 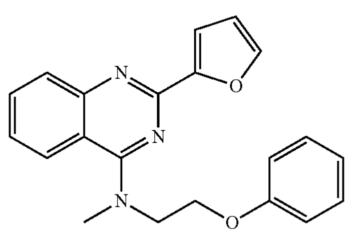 [SMILES: CN(CCOc1ccccc1)c1nc(-c2ccco2)nc2ccccc12] | 345 | 31.62 activator |
| 134 | 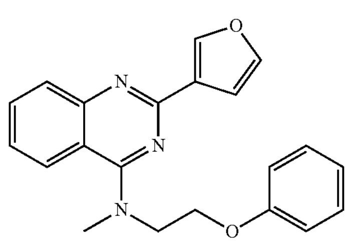 [SMILES: CN(CCOc1ccccc1)c1nc(-c2ccoc2)nc2ccccc12] | 345 | 0.65 activator |

-continued

Table of Additional Substituted Quinazoline Compounds.

| No. | Structure | MW | Activity AC$_{50}$ or IC$_{50}$ (μM unless nM indicated) |
|---|---|---|---|
| 135 | 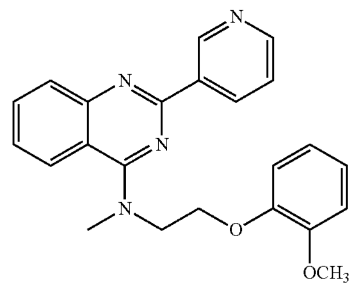 [SMILES: COc1ccccc1OCCN(C)c1nc(-c2cccnc2)nc2ccccc12] | 386 | 2.39 activator |
| 136 | 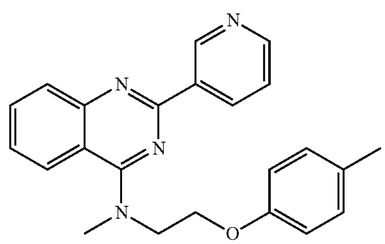 [SMILES: Cc1ccc(OCCN(C)c2nc(-c3cccnc3)nc3ccccc23)cc1] | 370 | 3.55 activator |
| 137 | 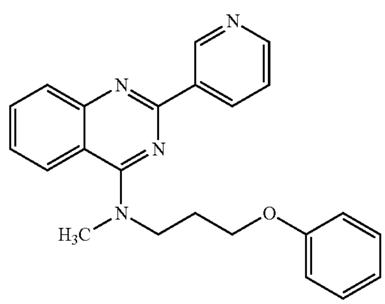 [SMILES: CN(CCCOc1ccccc1)c1nc(-c2cccnc2)nc2ccccc12] | 370 | 5.01 activator |
| 138 | 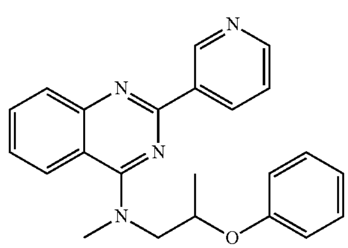 [SMILES: CC(CN(C)c1nc(-c2cccnc2)nc2ccccc12)Oc1ccccc1] | 370 | 5.62 activator |
| 139 | 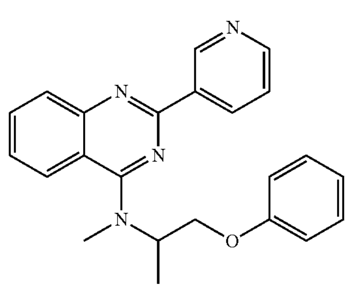 [SMILES: CC(COc1ccccc1)N(C)c1nc(-c2cccnc2)nc2ccccc12] | 370 | 5.62 activator |

-continued
Table of Additional Substituted Quinazoline Compounds.
| No. | Structure | MW | Activity $AC_{50}$ or $IC_{50}$ (μM unless nM indicated) |
|---|---|---|---|
| 140 | 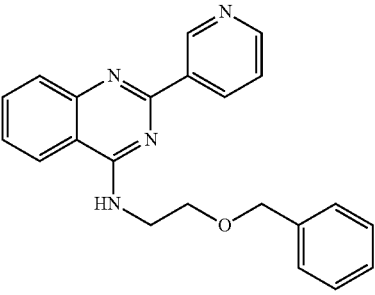 [SMILES: c1ccc(COCCNc2nc(-c3cccnc3)nc3ccccc23)cc1] | 356 | 11.22 inhibitor |
| 141 | 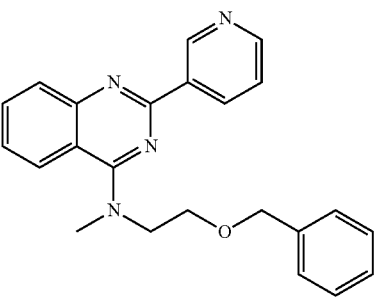 [SMILES: CN(CCOCc1ccccc1)c1nc(-c2cccnc2)nc2ccccc12] | 370 | 11.22 inhibitor |
| 142 | 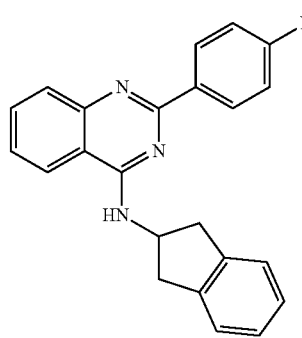 | 352 | 0.0071 inhibitor |
| 143 | 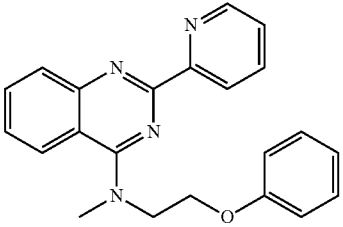 [SMILES: CN(CCOc1ccccc1)c1nc(-c2ccccn2)nc2ccccc12] | 356 | Weak activator |
| 144 | 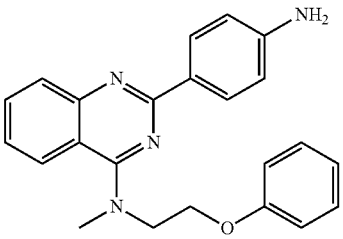 [SMILES: CN(CCOc1ccccc1)c1nc(-c2ccc(N)cc2)nc2ccccc12] | 370 | Weak inhibitor |

-continued

Table of Additional Substituted Quinazoline Compounds.

| No. | Structure | MW | Activity AC$_{50}$ or IC$_{50}$ (µM unless nM indicated) |
|---|---|---|---|
| 145 | 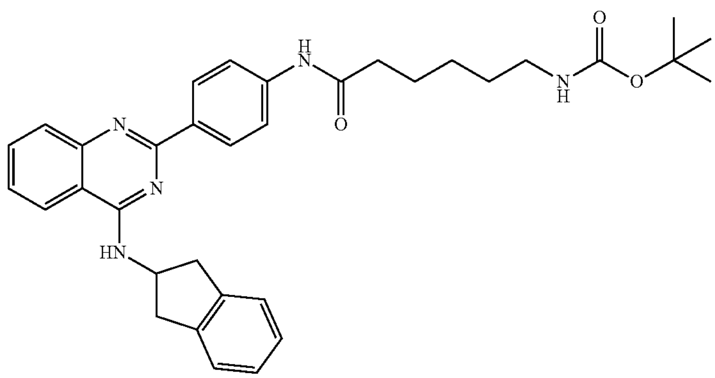 [SMILES: CC(C)(C)OC(=O)NCCCCCC(=O)Nc1ccc(-c2nc(NC3Cc4ccccc4C3)c3ccccc3n2)cc1] | 565 | 5.6 nM inhibitor |
| 146 | 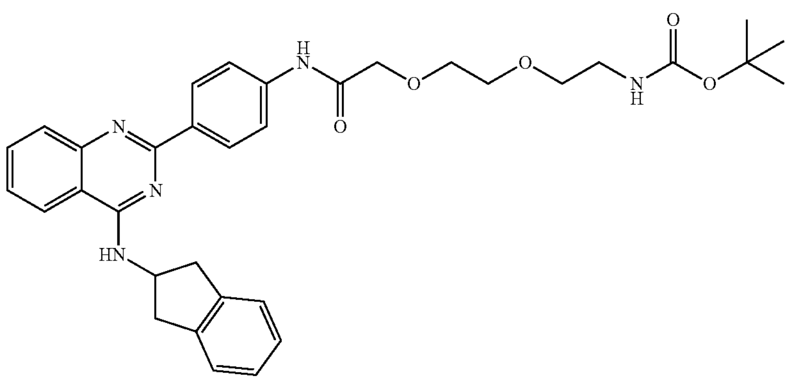 [SMILES: CC(C)(C)OC(=O)NCCOCCOCC(=O)Nc1ccc(-c2nc(NC3Cc4ccccc4C3)c3ccccc3n2)cc1] | 597 | 39.8 nM inhibitor |
| 147 | 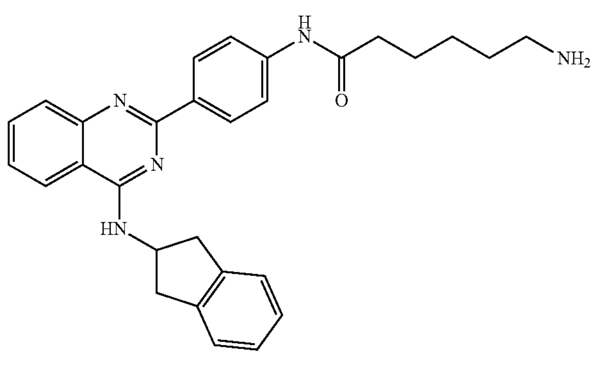 [SMILES: NCCCCCC(=O)Nc1ccc(-c2nc(NC3Cc4ccccc4C3)c3ccccc3n2)cc1] | 465 | 7.5 nM inhibitor |
| 148 | 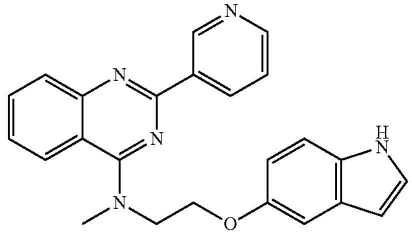 [SMILES: CN(CCOc1ccc2[nH]ccc2c1)c1nc(-c2cccnc2)nc2ccccc12] | 395 | |

-continued
Table of Additional Substituted Quinazoline Compounds.
| No. | Structure | MW | Activity AC$_{50}$ or IC$_{50}$ (μM unless nM indicated) |
|---|---|---|---|
| 149 | 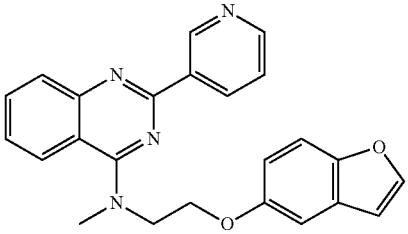 [SMILES: CN(CCOc1ccc2occc2c1)c1nc(-c2cccnc2)nc2ccccc12] | 396 | |
| 150 | 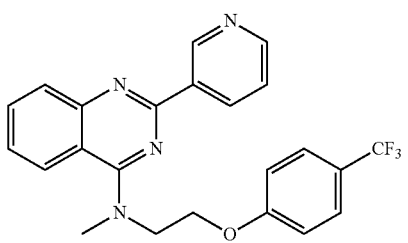 [SMILES: CN(CCOc1ccc(C(F)(F)F)cc1)c1nc(-c2cccnc2)nc2ccccc12] | 424 | NA |
| 151 | 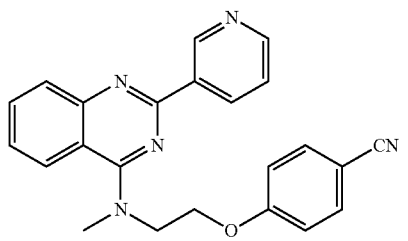 [SMILES: CN(CCOc1ccc(C#N)cc1)c1nc(-c2cccnc2)nc2ccccc12] | 381 | 7.08 |
| 152 | 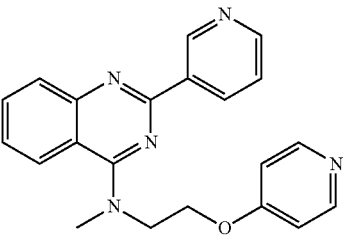 [SMILES: CN(CCOc1ccncc1)c1nc(-c2cccnc2)nc2ccccc12] | 357 | |
| 153 | 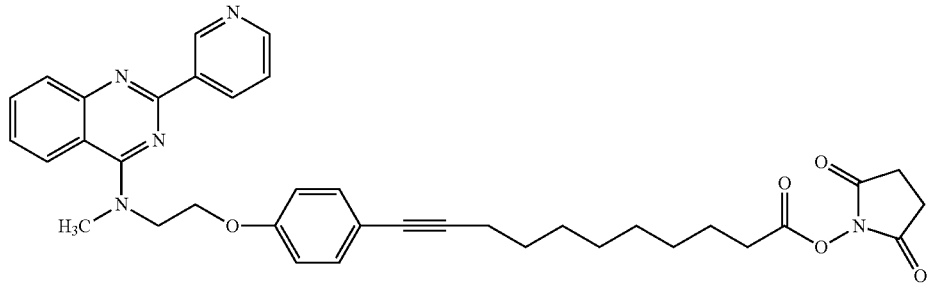 [SMILES: CN(CCOc1ccc(C#CCCCCCCCCC(=O)ON2C(=O)CCC2=O)cc1)c1nc(-c2cccnc2)nc2ccccc12] | 633 | activator |

-continued
Table of Additional Substituted Quinazoline Compounds.
| No. | Structure | MW | Activity AC$_{50}$ or IC$_{50}$ (µM unless nM indicated) |
|---|---|---|---|
| 154 | 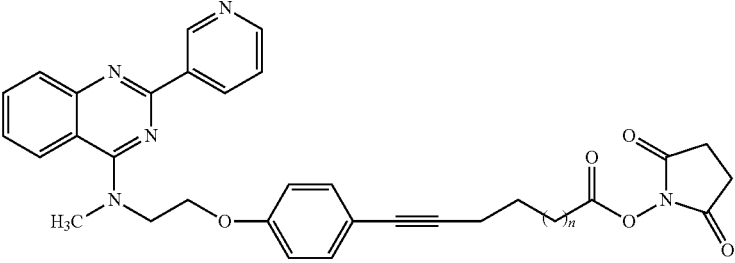 n = 1-6 | | |
| 155 | 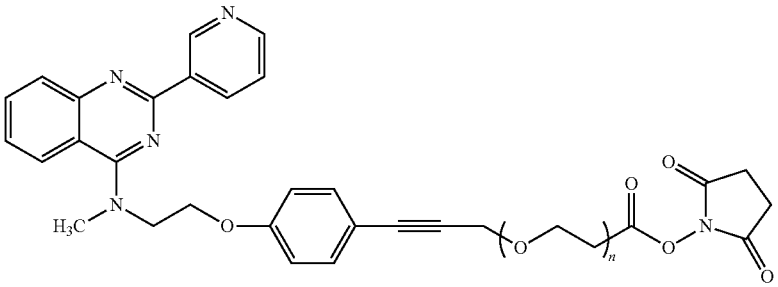 n = 1-4 | | |
| 156 | 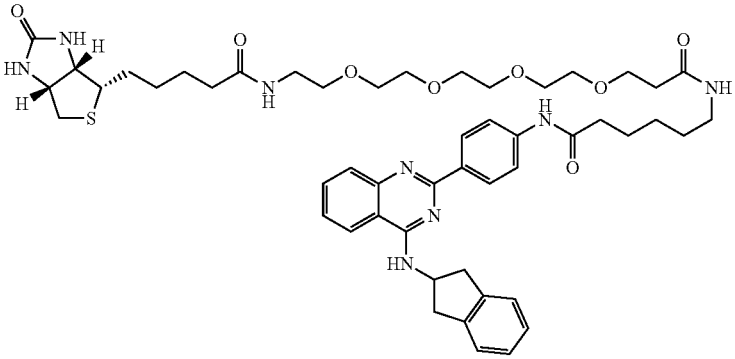 [SMILES: O=C(CCCC[C@@H]1SC[C@@H]2NC(=O)N[C@@H]21)NCCOCCOCCOCCOCCC(=O)NCCCCCC(=O)Nc1ccc(-c2nc(NC3Cc4ccccc4C3)c3ccccc3n2)cc1] | 938 | 1.95 nM inhibitor |
| 157 | 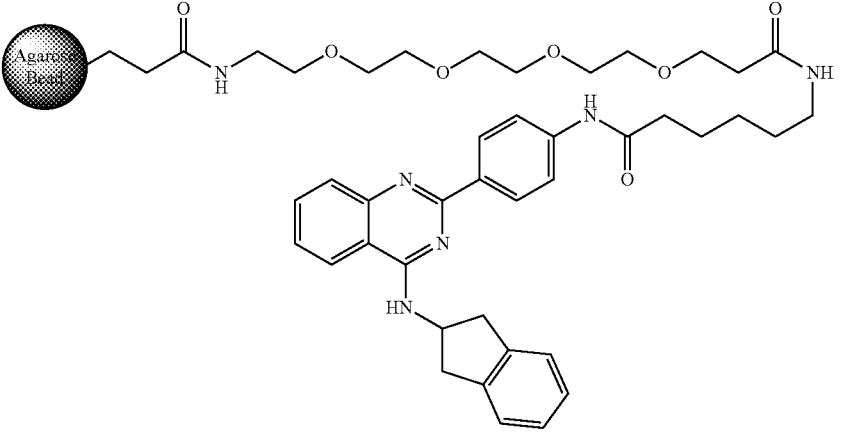 [SMILES: CCCC(=O)NCCOCCOCCOCCOCCC(=O)NCCCCCC(=O)Nc1ccc(-c2nc(NC3Cc4ccccc4C3)c3ccccc3n2)cc1] | | |

-continued

Table of Additional Substituted Quinazoline Compounds.

| No. | Structure | MW | Activity AC$_{50}$ or IC$_{50}$ (μM unless nM indicated) |
|---|---|---|---|
| | | | Kd value |
| 158 | 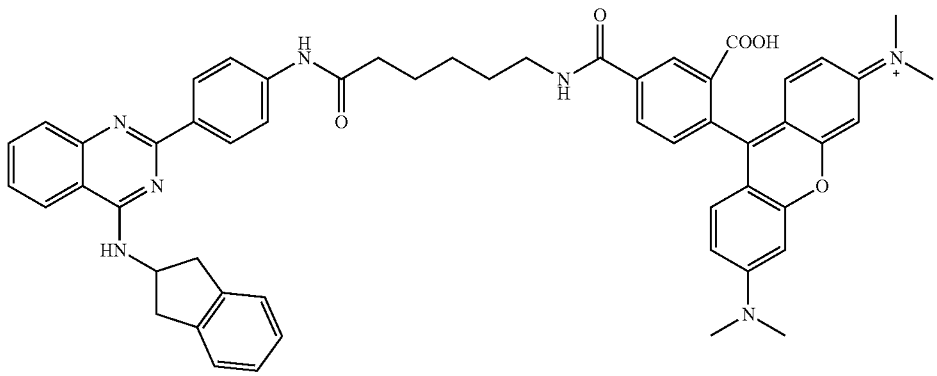 [SMILES: CN(C)c1ccc2c(-c3ccc(C(=O)NCCCCCC(=O)Nc4ccc(-c5nc(NC6Cc7ccccc7C6)c6ccccc6n5)cc4)cc3C(=O)O)c3ccc(=[N+](C)C)cc-3oc2c1] | 878 | 79 nM |
| 159 | 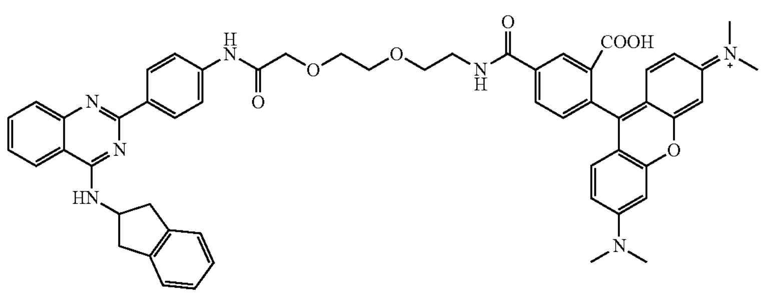 [SMILES: CN(C)c1ccc2c(-c3ccc(C(=O)NCCOCCOCC(=O)Nc4ccc(-c5nc(NC6Cc7ccccc7C6)c6ccccc6n5)cc4)cc3C(=O)O)c3ccc(=[N+](C)C)cc-3oc2c1] | 910 | 126 nM |
| 160 | 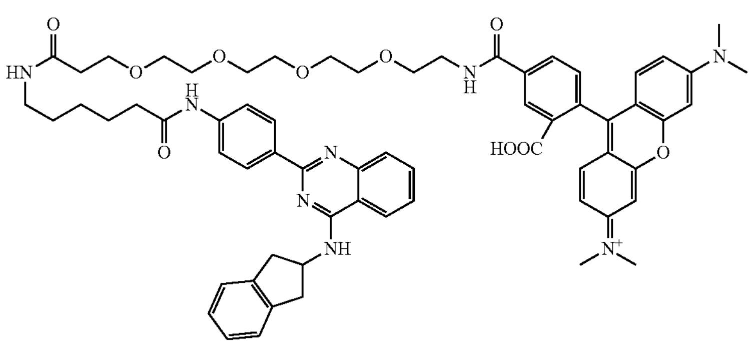 [SMILES: CN(C)c1ccc2c(-c3ccc(C(=O)NCCOCCOCCOCCOCCC(=O)NCCCCCC(=O)Nc4ccc(-c5nc(NC6Cc7ccccc7C6)c6ccccc6n5)cc4)cc3C(=O)O)c3ccc(=[N+](C)C)cc-3oc2c1] | 1125.5 | 7.1 nM |

Table of Additional Substituted Quinazoline Compounds.

| No. | Structure | MW | Activity AC$_{50}$ or IC$_{50}$ (μM unless nM indicated) |
|---|---|---|---|
| 161 | 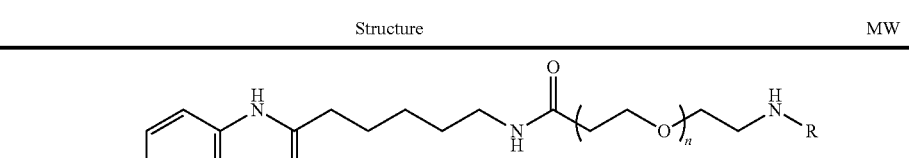 n = 1-10 R: fluorophore, for example: TAMRA, Fluorescein, etc or Biotin, or agarose bead | | |

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound or a salt or solvate thereof having a formula:

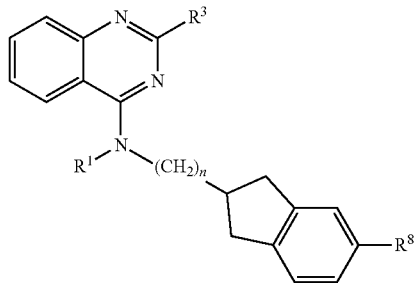

wherein:

$R^1$ is hydrogen or C1-C10 alkyl;

n is 0, 1, 2, 3, or 4;

$R^8$ is hydrogen, C1-C8 alkyoxy, C1-C8 alkyl, halo, or $R^8$ has a formula selected from

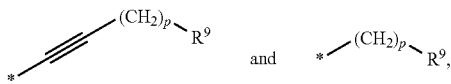

p is 1-10 and $R^9$ is amino or $R^9$ has a formula selected from

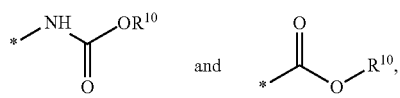

wherein $R^{10}$ is H, C1-C6 straight chain or branched alkyl, or a succinimidyl group;

$R^3$ is pyridinyl, phenyl, thiophenyl, halo, furanyl, or pyrimidinyl, and $R^3$ optionally is substituted at one or more positions with C1-C8 alkyl, halo, or amino, or $R^3$ has a formula,

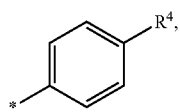

wherein R⁴ is amino, or R⁴ has a formula

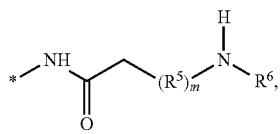

wherein R⁵ is CH₂— or O—CH₂—CH₂—, and m is 0-4, R⁶ is H or R⁶ has a formula

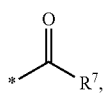

wherein R⁷ is H, —OH, C1-C8 alkyl, or C1-C8 alkoxy.

2. The compound of claim 1, wherein R³ is selected from the group consisting of

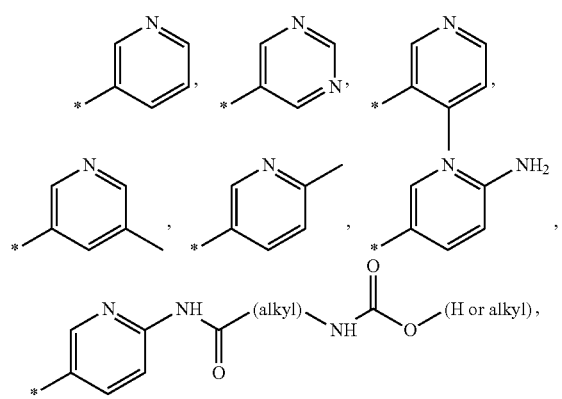

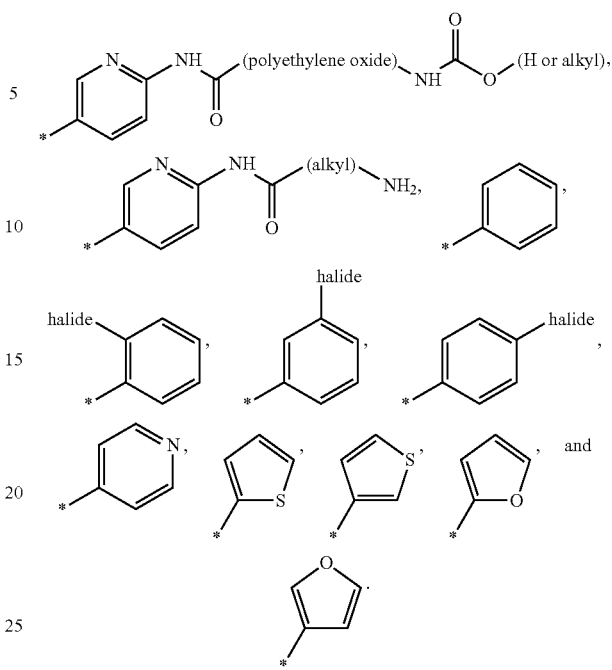

3. The compound of claim 1, wherein R¹ is H and n is 0.

4. The compound of claim 1, wherein R¹ is methyl and n is 0.

5. The compound of claim 1, wherein R¹ is H and n is 1.

6. The compound of claim 1, wherein R¹ is methyl and n is 1.

7. The compound of claim 1, wherein R³ is pyridinyl, optionally pyridine-3-yl, and R³ optionally is substituted at one or more positions with C1-C8 alkyl, halo, or amino.

8. The compound of claim 1 conjugated to biotin, a solid support, or a fluorophore.

9. A pharmaceutical composition comprising the compound of claim 1 and a pharmaceutical carrier.

10. A compound having a formula:

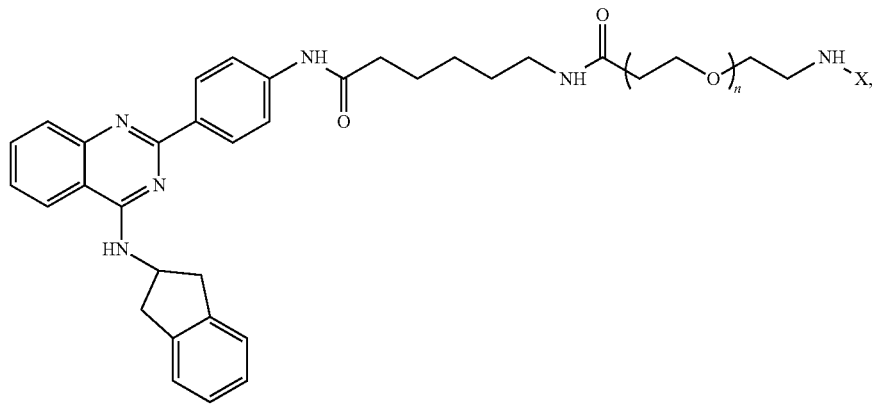

wherein n=1-10, and X is a fluorophore, biotin, or a solid support.

* * * * *